US006995188B2

(12) United States Patent
Zingaro et al.

(10) Patent No.: US 6,995,188 B2
(45) Date of Patent: *Feb. 7, 2006

(54) S-DIMETHYLARSINO-THIOSUCCINIC ACID S-DIMETHYLARSINO-2-THIOBENZOIC ACID S-(DIMETHYLARSINO) GLUTATHIONE AS TREATMENTS FOR CANCER

(75) Inventors: Ralph A. Zingaro, College Station, TX (US); Emil J. Freireich, Houston, TX (US); Hatice Duzkale, Houston, TX (US); Hagop Kantarjian, Bellaire, TX (US); Srdan Verstovsek, Houston, TX (US); Merida Sotelo-Lerma, Hermosillo (MX)

(73) Assignees: Board of Regents, The University of Texas System, Austin, TX (US); The Texas A&M University System, College Station, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/035,178

(22) Filed: Jan. 13, 2005

(65) Prior Publication Data

US 2005/0131062 A1      Jun. 16, 2005

Related U.S. Application Data

(63) Continuation of application No. 10/337,969, filed on Jan. 7, 2003.

(60) Provisional application No. 60/346,492, filed on Jan. 7, 2002.

(51) Int. Cl.
  *A61K 31/285*  (2006.01)
  *A61K 33/36*   (2006.01)
  *C07F 9/70*    (2006.01)

(52) U.S. Cl. .......................... 514/504; 556/71; 556/77; 556/78; 556/80; 424/629

(58) Field of Classification Search ................ 424/629; 514/504; 556/71, 77, 78, 80
See application file for complete search history.

(56) References Cited

U.S. PATENT DOCUMENTS 6,191,123 B1    2/2001  Uckun et al. ................ 514/150
  2004/0028750 A1  2/2004  Lu .............................. 424/629

FOREIGN PATENT DOCUMENTS

EP       1002537      10/1998
  WO    WO 99/24029     11/1998

OTHER PUBLICATIONS

American Conference of Governmental Industrial Hygienists, Inc. (ACGIH). Arsenic and soluble compounds, including arsine. Documentation of the Threshold Limit Values and Biological Exposure Indices, sixth edition, 1991.

Bachleitner-Hofmann et al., "Arsenic trioxide and ascorbic acid: synergy with potential implications for the treatment of acute myeloid leukaemia," *Br. J. Haematol.*, 112(3):783-786, 2001.

Banks et al., "Biomolecules bearing the S- or SeAsMe2 function: amino acid and steroid derivatives," *J. Medicinal Chem.* 22:572-575, 1979.

Beliles, "The Metals," In *Patty's Industrial Hygiene and Toxicology, fourth edition* G.D. Clayton and F.E. Clayton, eds. John Wiley & Sons, Inc.: New York. pp. 1913-1925, 1994.

Calleja and Warrell, "Differentiating agents in pediatric malignancies: all-trans-retinoic acid and arsenic in acute promyelocytic leukemia," *Curr. Oncol. Rep.*, 2:519-523, 2000.

Chen et al., "6-thio- and —seleno-alpha-D-glucose esters of dimethylarsinous acid," *Carb. Res.* 50:53-62, 1976.

Chen et al., "Synthesis of 1-and 6-S-and 1-and 6-Se-derivatives of 2-amino-2-deoxy-alpha/beta-D-glucopyranose," *J. Chemical Soc, Perkin Trans.* 1:2287-2293, 1980.

Cuzick et al., "Medicinal arsenic and internal malignancies," *Br. J. Cancer*, 45:904-911, 1982.

Daniel and Zingaro "Dimethylarsinous acid esters of 1-thio- and -seleno- galactose. A new class of potential carcinostatic agents," *Phosphorus and Sulfur* 4:179-185, 1978.

Forkner and McNair-Scott, "Arsenic as a therapeutic agent in chronic myeloid leukemia," *JAMA* 97(1):3-6, 1931.

Geissler et al., "In vivo effects of arsenic trioxide in refractory acute myeloid leukemia other than acute promyelocytic leukemia," *Blood* 94:4230a. 1999.

Goyer, "Toxic effects of metals" In *Casarett and Doull's Toxicology: The Basic Science of Poisons*, 5th edition. C.D. Klassen, ed, McGraw-Hill: New York. pp. 691-698, 1996.

(Continued)

*Primary Examiner*—Porfirio Nazario-Gonzalez
(74) *Attorney, Agent, or Firm*—Fish & Neave IP Group Ropes & Gray LLP

(57) ABSTRACT

Arsenic trioxide, an inorganic compound, is commercially available anti-cancer agent but it carries significant toxicity. Organic arsenicals, on the other hand, are much less toxic, to the extent that the methylation of inorganic arsenic in vivo into organic arsenicals has been considered a detoxification reaction. New organic arsenic derivatives have been synthesized, including S-dimethylarsino-glutathione, S-dimethylarsino-thiosuccinic acid and S-dimethylarsino-thiobenzoic acid, and established its potent in vitro cytotoxic activity against numerous human tumor cell lines, both of solid and hematological origin, as well as against malignant blood cells from patients with leukemia. Results form a basis for the development of S-dimethylarsino-glutathione, S-dimethylarsino-thiosuccinic acid, S-dimethylarsino-thiobenzoic acid, and other organic arsenicals as an anti-cancer therapy, combining high efficacy with very low, if any, toxicity.

30 Claims, 32 Drawing Sheets

OTHER PUBLICATIONS

Grignani et al., "The acute promyelocytic leukemia-specific PML-RAR alpha fusion protein inhibits differentiation and promotes survival of myeloid precursor cells," *Cell*, 74:423-431, 1993.

Hughes and Kenyon, "Dose-dependent effects on the disposition of monomethylarsonic acid and dimethylarsinic acid in the mouse after intravenous administration," *J. Toxicol. Environ. Health*, 53(2):95-112, 1998.

IARC. Some metals and metallic compounds. IARC Monographs on the Evaluation of the Carcinogenic Risk of Chemicals to Man. vol. 23:39-141, 1980.

Kitamura et al., "New retinoids and arsenic compounds for the treatment of refractory acute promyelocytic leukemia: clinical and basic studies for the next generation," *Cancer Chemother Pharmacol.*, 40 (Suppl):S36-S41, 1997.

Knock et al., "The use of selected sulfhydryl inhibitors in a preferential drug attack on cancer," *Surg. Gynecol. Obstet.* 133:458-466, 1971.

König, A. et al., "Comparative activity of melarsoprol and arsenic trioxide in chronic B-cell leukemia lines," *Blood* 90:562-570, 1997.

Lallemand-Breitenbach et al., "Retinoic acid and arsenic synergize to eradicate leukemic cells in a mouse model of acute promyelocytic leukemia," *J. Exp. Med.*, 189:1043-1052, 1999.

Mountain et al., "Chemotherapy studies in an animal tumor spectrum: II. Sensitivity of tumors to fourteen antitumor chemicals," *Cancer Res.* 26:181-206, 1966.

Rivi et al., "Organic arsenical melarsoprol shows growth suppressive activity via programmed cell death on myeloid and lymphoid leukemia derived cell lines," *Blood* (Suppl.) 88:68a, 1996.

Rosenthal and Zingaro, "The synthesis and characterization of thio sugar esters of diorganylarsinous acids," *Phosphorus and Sulfor* 9:107-116, 1980.

Rousselot et al., "Use of arsenic trioxide ($As_2O_3$) in the treatment of chronic myelogenous leukemia: In vito and in vivo studies," *Blood* 94:4457a, 1999.

Soignet et al., "Clinical study of an organic arsenic melarsoprol, in patients with advanced leukemia," *Cancer Chemother. Pharmacol.* 44:471-421, 1999.

Soignet et al., "Dose-ranging and clinical pharmacologic study of arsenic trioxide in patients with advanced hematologic cancers," *Blood* 94:1247a, 1999.

Tallman, "Therapy of acute promyelocytic leukemia: all-tans retinoic acid and beyond," *Leukemia*, 12 (Suppl 1):S37-S40, 1998.

Wiernik et al., "Phase II trial of arsenic trioxide ($As_2O_3$) in patients with relapsed/refractory acute myeloid leukemia, blast crisis of CML or myelodysplasia," *Blood* 94:2283a, 1999.

Zhang et al., "Arsenic trioxide treated 72 cases of acute promyelocytic leukemia," *Chin. J. Hematol.* 17:58-62, 1996.

Aslanidis et al., "Methylarsino-substituted hydroxy carboxylate esters," *Chemiker-Zeitung*, 112(4):125-127, 1988.

Beckermann and Bernhard, "Determination of monovethylarsonic acid and dimethylarsinic acid by derivatization with thioglycolic acid methyl ester and gas-liquid chromatographic separation," *Analytica Chimica Acta*, 135(1):77-84, 1982.

Cullen et al., "The metabolism of methylarsine oxide and sulfide," *Applied Organometallic Chemistry*, 3(1):71-78, 1989.

Cullen et al., "The reaction of methylarsincals with thiols: some biological implications," *J. Inorganic Biochemistry*, 21(3):179-194, 1984.

Emran et al., "Synthesis and biodistribution of radioarsenic labeled dimethylarsinothiols: derivatives of pennicillamine and mercaptoethanol," *International Journal of Nuclear Medicine and Biology*, 11(3-4):259-261, 1984.

Hosain et al., "Synthesis of radioarsenic labeled dimethylchloroarsine for derivation of a new group of radiopharmceuticals," *International Journal of Applied Radiation and Isotopes*, 33(12):1477-1478, 1982.

Ionov et al., "Reaction of tertiary arsine sulfides with alkyl chlorocarbonates," *Zhurnal Obshchei Khimii*, 46(11):2555-2558, 1976.

Kala et al., "The MRP2/cMOAT transporter and arsenic-glutathione complex formation are required for bilary excretion of arsenic," *J. Biol. Chem.*, 275(43):33404-33408, 2000.

King and Ludford, "Relation between the constitution of arsenicals and their action on cell division," *Journal of the Chemical Society Abstracts*, 2086-2088, 1950.

Lam et al., "Spectroscopic studies of arsenic (III) binding to *Escherichia coli* RI methyltransferase and to two mutants, C223S and W183F," *Biochemistry*, 31(43):10438-10442, 1992.

Lin et al., "Methylarsenicals and arsinothiols are potent inhibitors of mouse liver thioredoxin reductase," *Chemical Research in Toxicology*, 12(10):924-930, 1999.

Mester et al., "Specification of dimethylarsinic acid and monomethylarsonic acid by gas chromatography-mass spectrometry," *Journal of Chromatography*, 832(1+2):183-190, 1999.

Schoene et al., "Speciation of arsenic-containing chemical warfare agents by gas chromatographic analysis after derivatization with thioglcolic acid methyl ester," *Journal of Chromatography*, 605(2):257-262, 1992.

Scott et al., "Reactions of arsenic (III) and arsenic (V) species with glutathione," *Chemical Research in Toxicology*, 6(1):102-106, 1993.

Styblo et al., "Comparative inhibition of yeast glutathione reductase by arsenicals and arsenothiols," *Chemical Research in Toxicology*, 10(1):27-33, 1997.

Tsalev et al., "Flow-injection hydride generation atomic absorption spectrometric sutdy of the automated on-line pre-reduction of arsenate, methylarsonate and dimethylarsinate and high-performance liquid chromatographic separation of their I-cysteine complexes," *Talanta*, 51(6):1059-1068, 2000.

Tsao et al., Optically detected magnetic resonance study of the interaction of an arsenic (III) derivative of cacodylic acid with EcoRI methyltransferase, *Biochemistry*, 30(18):4565-4572, 1991.

Vega et al., "Differential effects of trivalent and pentavalent arsenicals on cell proliferation and cytokine secretion in normal human epidermal keratinocytes," *Toxicology and Applied Pharmacology*, 172(3):225-232, 2001.

FIG. 10 — 4 day trypan blue assay - AML patient

FIG. 11 - MER1: 5 day trypan blue assay - AML patient

FIG. 13 — MER1: 4 day trypan blue assay - ALL patient

FIG. 14 – MER1: 5 day trypan blue assay - normal donor

FIG. 15 – 8 day clonogenic assay - normal donor 5 day trypan blue assay - CLL patient

S-DIMETHYLARSINO-THIOSUCCINIC ACID S-DIMETHYLARSINO-2-THIOBENZOIC ACID S-(DIMETHYLARSINO) GLUTATHIONE AS TREATMENTS FOR CANCER

CROSS REFERENCE TO RELATED APPLICATIONS

This application is a continuation of U.S. application Ser. No. 10/337,969, filed Jan, 7, 2003, which claims the benefit of provisional U.S. Application Ser. No. 60/346,492, filed Jan. 7, 2002. The entire teachings of the above referenced applications are incorporated herein by reference and without disclaimer.

BACKGROUND OF THE INVENTION

I. Field of the Invention

The present invention relates generally to the field of anti-cancer therapy. More particularly, it provides organic arsenic compounds and methods for their use in treating cancers such as leukemia.

II. Description of Related Art

Despite progress in leukemia therapy, most adult patients with leukemia still die from disease progression and an estimated 31,500 new cases and 21,500 deaths are expected in the year 2001. Arsenic trioxide, an inorganic compound, has recently been approved for the treatment of patients with relapsed or refractory acute promyelocytic leukemia (APL) and is being evaluated as therapy for other leukemia types. However, its use is limited by its toxicity.

Arsenic was used as a medicinal agent more than 2400 years ago in Greece and Rome, and arsenic still comprises the active ingredient in certain folk remedies, particularly in Central and Southern Asia (Bainbridge et al., 1914). The history and folklore of arsenic prompted intensive studies by many early pharmacologists. The foundations of many modern concepts of chemotherapy derive from Ehrlich's early work with arsenicals (e.g. the "silver bullet" for syphilis), and such drugs were once a mainstay of cancer chemotherapy. For example, in the early 1930's, Fowler's solution (inorganic arsenic dissolved in water) was used for controlling elevated leukocyte counts in chronic myelogenous leukemia (Forkner et al., 1931). In fact, clinical improvement of the leukemia, including control of fever, reduction of white cell count and splenomegaly, and improvement in anemia could be observed. Various arsenicals were briefly examined in early preclinical cancer screening studies at the U.S. National Cancer Institute (Tarnowski et al., 1966). However, the clinical use of arsenicals in the treatment of cancer in the U.S. virtually ceased in the early 1970's with the advent of now traditional cytotoxic drugs and radiotherapy along with reports of arsenic poisoning from chronic low-dose ingestion (Knock et al., 1971; Cuzick et al., 1987). Still, there is large body of knowledge regarding effects of arsenicals on human subjects from both medicinal and toxicological standpoints. In current therapeutics, arsenicals are important only for the treatment of certain tropical diseases, such as the use of melarsoprol, an organic compound, against African trypanosomiasis (Investigational Drug Brochure, 1987). However, Chinese reports of the striking activity of arsenic trioxide ($As_2O_3$) (Zhang et al., 1996), an inorganic compound, against APL have engendered considerable interest. This resulted in the recent approval of arsenic trioxide for treatment of patients with relapsed or refractory APL. Preliminary data from China and the recent experience in the U.S., however, suggest a role for arsenic trioxide in the other hematologic cancers as well. Consequently, the activity of arsenic trioxide as an antileukemic agent is currently being investigated in many types of leukemia. Although the results look favorable in terms of the response rate of some of the leukemia types that are being investigated, systemic toxicity of arsenic trioxide is a problem (Soignet et al., 1999; Wierniket al., 1999; Geissler et al., 1999; Rousselot et al., 1999).

The only organic arsenical (OA) still manufactured for human use, melarsoprol, has been evaluated for its antileukemic (WO9924029, EP1002537) properties and showed significant activity. However, this compound is excessively toxic to patients with leukemia at drug concentration and schedule used previously for treatment of trypanosomiasis. Therefore, there is a need to identify arsenic derivatives that can be used for the treatment of hematologic malignancies and cancer in general, that have similar or greater activity and lower toxicity than arsenic trioxide. Organic arsenic derivatives may fulfill this promise as they should be less toxic than the inorganic arsenic trioxide.

SUMMARY OF THE INVENTION

The present invention overcomes these and other defects in the art and provides organic arsenical compounds with anti-cancer properties. In some embodiments, the present invention comprises compounds having anti-cancer activity comprising the structure:

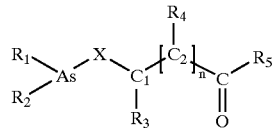

wherein $R_1$ and $R_2$ are independently alkyls with 1–10 carbon atoms; X is S or Se; $R_3$ is —H, —COOH, —$CH_2$—COOH, —$CH_2$—$CH_2$—COOH, —CH($CH_3$)—COOH, —CH($CH_2$—$CH_3$)—COOH, or —$CH_2$—$CH_2$—$CH_2$—COOH; n is 0 or 1; $R_4$ is —OH, —H, —$CH_3$, or a glutamine substituent; $R_3$, $R_4$, $C_1$ and $C_2$ all independently comprise part of an aromatic ring or substituted aromatic ring; and $R_5$ is a —OH, or glycine substituent; or a pharmaceutically acceptable salt or formulation thereof.

In particular embodiments, the compound can have the formula:

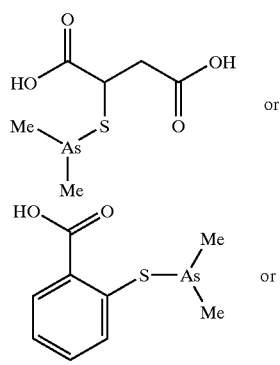

-continued

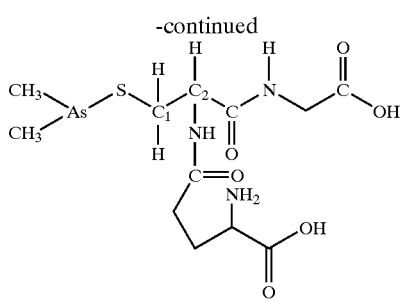

or is a pharmaceutically acceptable salt or formulation thereof.

Thus, the invention also comprises compositions and pharmaceutical compositions comprising the compounds described above.

In other embodiments, the invention comprises of a pharmaceutical composition having anti-cancer activity comprising a pharmaceutical carrier and an organic arsenical compound. In some embodiments, such a composition has the formula:

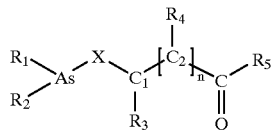

wherein $R_1$ and $R_2$ are independently alkyls with 1–10 carbon atoms; X is S or Se; $R_3$ is —H, —COOH, —CH$_2$—COOH, —CH$_2$—CH$_2$—COOH, —CH(CH$_3$)—COOH, —CH(CH$_2$—CH$_3$)—COOH, or —CH$_2$—CH$_2$—CH$_2$—COOH; n is 0 or 1; $R_4$ is —OH, —H, —CH$_3$, or a glutamine substituent; $R_3$, $R_4$, $C_1$ and $C_2$ all independently comprise part of an aromatic ring or substituted aromatic ring; and $R_5$ is a —OH, or glycine substituent; or a pharmaceutically acceptable salt thereof.

In yet other embodiments, the invention comprises a method of treating a patient with cancer comprising administering a composition comprising a therapeutically effective amount of a compound having the formula:

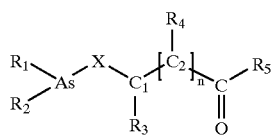

wherein $R_1$ and $R_2$ are independently alkyls with 1–10 carbon atoms; X is S or Se; $R_3$ is —H, —COOH, —CH$_2$—COOH, —CH$_2$—CH$_2$—COOH, —CH(CH$_3$)—COOH, —CH(CH$_2$—CH$_3$)—COOH, or —CH$_2$—CH$_2$—CH$_2$—COOH; n is 0 or 1; $R_4$ is —OH, —H, —CH$_3$, or a glutamine substituent; $R_3$, $R_4$, $C_1$ and $C_2$ all independently comprise part of an aromatic ring or substituted aromatic ring; and $R_5$ is a —OH, or a glycine substituent; or a pharmaceutically acceptable salt or formulation thereof to the patient. The therapeutically effective amount of a compound could be 0.1–1000 mg/kg or 1–500 mg/kg, or 10–100 mg/kg.

In particular embodiments, the method may comprise administering the composition daily. It is further contemplated that treatment methods may involve multiple administrations. On other embodiments, the method further comprises administering one or more additional agents to the patient. The additional agent may be all-trans-retinoic acid, 9-cis retinoic acid, Am-80 or ascorbic acid. The use of other adjunct cancer therapies, such as chemotherapy, radiotherapy, gene therapy, hormone therapy and other cancer therapies known in the art are also contemplated in conjunction with the methods of the present invention.

Various methods of administration are contemplated, including regional, systemic, direct administration and by perfusion. Such methods include administration by injection, oral routes, intravenous, intraarterial, intratumoral, administration to tumoral vasculature, intraperitoneal, intratracheal, intramuscular, endoscopical, intralesional, percutaneous, subcutaneous, topical, nasal, buccal, mucosal, anogenital, rectal and the like.

In particular embodiments, the method of treating a patient with a cancer comprises administering a therapeutically effective amount of a compound having the formula:

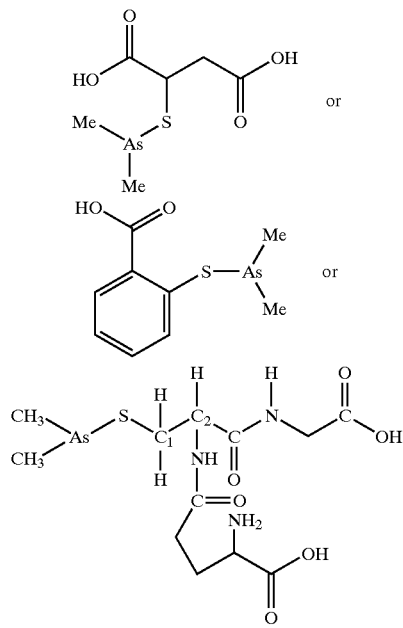

or a pharmaceutically acceptable salt or formulation thereof.

The methods of the invention may be used to treat any cancer, including but not limited, to a solid tumor, such as brain, lung, liver, spleen, kidney, lymph node, small intestine, pancreas, blood cells, bone, colon, stomach, breast, endometrium, prostate, testicle, ovary, central nervous system, skin, head and neck, esophagus, or bone marrow cancer. Furthermore, the cancer could be a hematological cancer, such as leukemia, acute promyelocytic leukemia, lymphoma, multiple myeloma, myelodysplasia, myeloproliferative disease, or refractory anemia.

The method can comprise of administering the compound daily such as by injection. Alternative routes and methods of administration described in the specification may also be used and the mode of administration will mainly depend on the type and location of the cancer. Furthermore, the method can comprise administering one or more additional agents to the patient. The additional agent may be all-trans-retinoic acid, 9-cis retinoic acid, Am-80 or ascorbic acid. However, the use of other agents that are normally used in the therapy of cancer are also contemplated. This includes the use of chemotherapeutic agents, radiation, surgery, gene-therapy, cytokines, hormonal therapy and a vast variety of other anti-cancer therapies known in the art.

As used herein the specification, "a" or "an" may mean one or more. As used herein in the claim(s), when used in conjunction with the word "comprising", the words "a" or "an" may mean one or more than one. As used herein "another" may mean at least a second or more.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 3A. Leukemia cell lines, FIG. 3B. CNS cell lines, FIG. 3C. Renal cancer cell lines, FIG. 3D. Non-small cell lung cancer cell lines, FIG. 3E. Melanoma cell lines, FIG. 3F. Prostate cancer cell lines, FIG. 3G. Colon cancer cell lines, FIG. 3H. Ovarian cancer cell lines, FIG. 3I. Breast cancer cell lines.

FIG. 5A. Leukemia cell lines, FIG. 5B. CNS cell lines, FIG. 5C. Renal cancer cell lines, FIG. 5D. Non-small cell lung cancer cell lines, FIG. 5E. Melanoma cell lines, FIG. 5F. Prostate cancer cell lines, FIG. 5G. Colon cancer cell lines, FIG. 5H. Ovarian cancer cell lines, FIG. 5I. Breast cancer cell lines.

FIG. 8A. Leukemia cell lines, FIG. 8B. CNS cell lines, FIG. 8C. Renal cancer cell lines, FIG. 8D. Non-small cell lung cancer cell lines, FIG. 8E. Melanoma cell lines, FIG. 8F. Prostate cancer cell lines, FIG. 8G. Colon cancer cell lines, FIG. 8H. Ovarian cancer cell lines, FIG. 8I. Breast cancer cell lines.

DESCRIPTION OF ILLUSTRATIVE EMBODIMENTS

I. The Present Invention

Figure 1:
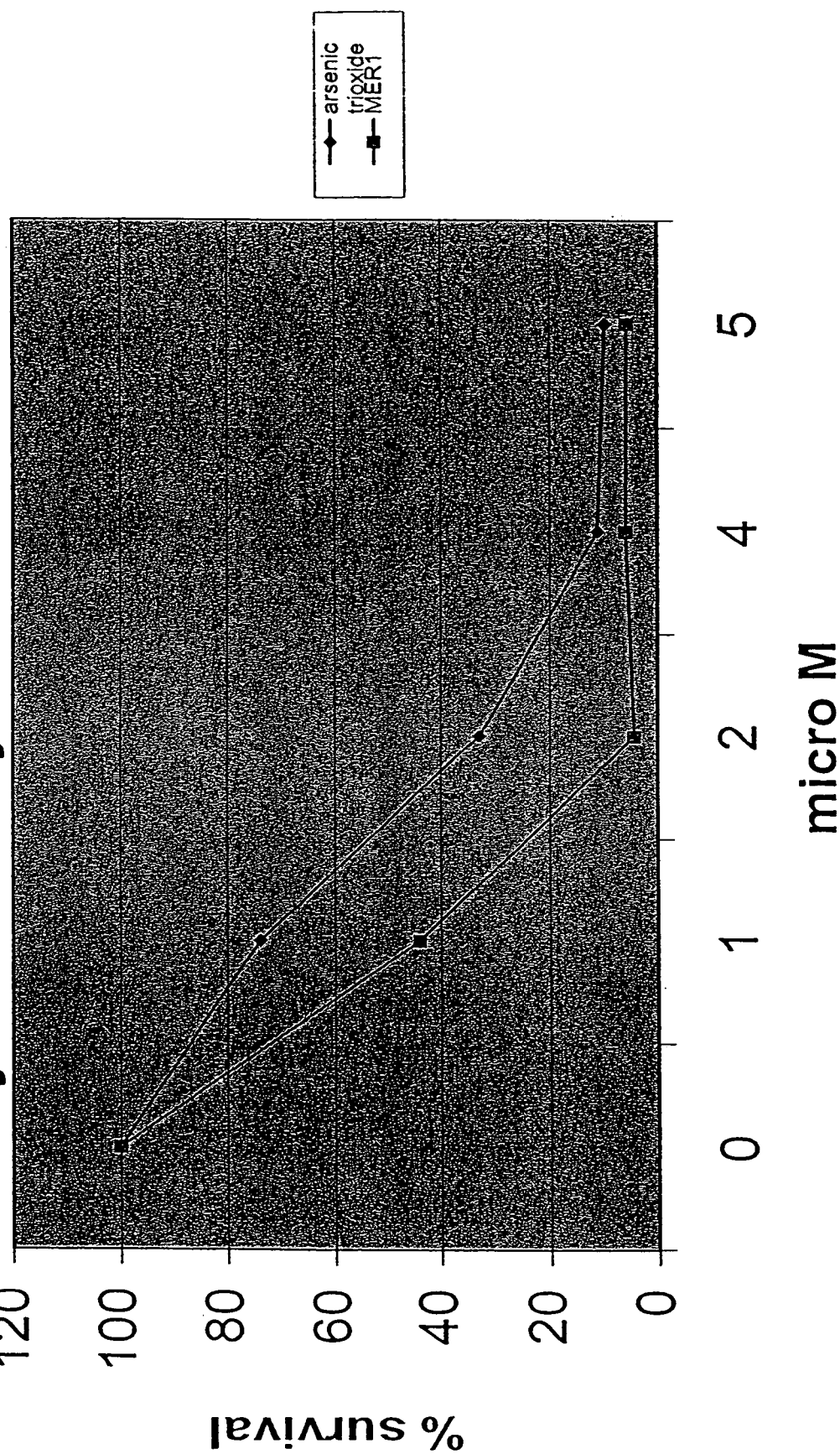
FIG. 1. The human leukemia cell line NB4 was incubated for 3 days with indicated concentrations of S-dimethylarsino-thiosuccinic acid (MER1) or arsenic trioxide. Cell survival was assessed by the MTT assay.

The present invention overcomes deficiencies in the art by providing a number of organic arsenic compounds for the treatment of cancer having similar or greater activity and lower toxicity than current treatment with arsenic trioxide. More particularly, the present invention provides S-dialkylarsino-thio carboxylic acids, including S-dimethylarsino-thiosuccinic acid and S-dimethylarsino-2-thiobenzoic acid, and methods for use in treating cancers. The present invention also provides S-dimethylarsino-glutathione and methods for its use in treating cancers.

II. Organic Arsenicals

Twenty years ago a large number of organic arsenicals (OA) derivatives were synthesized by Prof. Dr. Ralph A. Zingaro at Texas A&M University, a co-inventor in this application, and their physicochemical properties determined (Chen et al., 1976; Rosenthal et al., 1980; Chen et al., 1980; Daniel et al., 1978; Banks et al., 1979, the entire contents of all these references are incorporated herein by reference in their entirety). After it was shown that one of the compounds displayed in vitro activity against cancer cells, many of the newly synthesized OA were submitted to the National Institute of Health (NIH) for the evaluation of their anticancer activity. The compounds were tested in vivo in mice bearing P388 lymphocytic leukemia cells. The activity of these compounds was assessed by recording the survival time of groups of six mice treated with different drugs (intraperitoneally, daily for 5 days), as well as a control group, as shown in Table 1. The NIH criterion for significant activity is the percentage treatment/control (T/C)>125. This means that the group of animals receiving the drug survives at least 25% longer than the control group. A number of compounds displayed significant antileukemic activity, and some even reached % T/C of 180. Furthermore, the compounds were non-toxic as some were used at the dose of 200 mg/kg ($LD_{50}$ for arsenic trioxide is 10 mg/kg).

TABLE 1

In vivo activity of OA derivatives in mice bearing P388 lymphocytic leukemia cells, as reported by the NIH.

| Compound | Dose (mg/kg) | % T/C |
|---|---|---|
| 1. 2,3,4,6-tetra-O-acetyl-1-S-dibutylarsino-1-thio-β-D-glucopyranose | 100 | 117 |
| 2. 2,3,4,6-tetra-O-acetyl-1-S-dipropylarsino-1-thio-β-D-glucopyranose | 200 | 124 |
| 3. 2,3,4,6-tetra-O-acetyl-1-S-diethylarsino-1-thio-β-D-glucopyranose | 100 | 180 |
| 4. 2,3,4,6-tetra-O-acetyl-1-S-hydroxyethylmethyl-1-thio-β-D-glucopyranose | 100 | 116 |
| 5. 2,3,4,6-tetra-O-acetyl-1-S-dihexadecylarsino-1-thio-β-D-glucopyranose | 50 | 125 |
| 6. 2,3,4,6-tetra-O-acetyl-1-S-dicyclohexylarsino-1-thio-β-D-glucopyranose | 400 | Toxic |
| 7. 1,2,3,4,-tetra-O-acetyl-6-S-methyl-n-propylarsino-6-thio-β-D-glucopyranose | 200 | 118 |
| 8. 1,2,3,4,-tetra-O-acetyl-6-S-dihexadecylarsino-6-thio-β-D-glucopyranose | 100 | 125 |
| 9. 1,2,3,4,-tetra-O-acetyl-6-S-dicyclohexylarsino-6-thio-β-D-glucopyranose | 25 | 120 |

TABLE 1-continued

In vivo activity of OA derivatives in mice bearing P388 lymphocytic leukemia cells, as reported by the NIH.

| Compound | Dose (mg/kg) | % T/C |
|---|---|---|
| 10. S-dimethylarsino-DL-cysteine | 50 | 110 |
| 11. S-dimethylarsino-DL-penicillamine | 25 | 117 |
| 12. Bis [S-dimethylarsino-homocysteine] | 100 | 144 |
| 13. S-dimethylarsino-glutathione | 100 | 164 |
| 14. Bis [S-dimethylarsino-α-dihydrolipoic acid | 50 | 128 |
| 15. Se-dimethylarsino-selenocholesterol | 200 | 129 |
| 16. 2,3,4,6-tetra-O-acetyl-1-S-dimethylarsino-1-thio-β-D-galactopyranose | 100 | 129 |
| 17. 1-S-dimethylarsino-1-thio-β-D-galactopyranose | 50 | 125 |
| 18. 2-acetamido-3,4,6-tri-O-acetyl-2-deoxy-1-S-dimethylarsino-1-thio-β-D-glucopyranose | 50 | 136 |
| 19. 2-acetamido-2-deoxy-1-S-dimethylarsino-1-thio-β-D-glucopyranose | 100 | 125 |
| 20. 2-acetamido-1,3,4-tri-O-acetyl-2-deoxy-6-S-dimethylarsino-6-thio-α-D-glucopyranose | 100 | 136 |
| 21. 2-acetamido-2-deoxy-6-S-dimethylarsino-6-thio-α-D-glucopyranose | 100 | 125 |

Melarsoprol (Arsobal) is the only organic arsenical still manufactured for human use, and is not commercially available in the United States. Melarsoprol is accepted for use for trypanosomiasis, or African sleeping sickness, and has been evaluated for its antileukemic properties (WO9924029, EP1002537). Studies unexpectedly showed that melarsoprol had activity at least equivalent to that of arsenic trioxide against both APL and non-APL cell lines (Konig et al., 1997; Rivi et al., 1996). A limited clinical study of melarsoprol was then initiated in the U.S. in patients with advanced leukemia (Soignet et al., 1999). A total of 8 patients were treated on a 3 days per week schedule for 3 consecutive weeks (a dosing schedule that had previously been used for treatment of central nervous system trypanosomiasis). Only one patient (with chronic lymphocytic leukemia) displayed antitumor effects while most experienced neurological side effects. These results suggest that the dosing schedule developed for treatment of trypanosomiasis is excessively toxic in patients with leukemia and that further preclinical experiments, particularly in animal model of leukemia, is needed for melarsoprol.

Other organic arsenicals have been synthesized and include carboxylic acid and dicarboxylic acid arsenicals. These arsenicals have trivalent arsenic of the form:

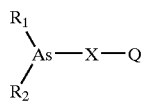

wherein $R_1$ and $R_2$ are independently alkyls with 1–10 carbon atoms and are preferably methyl, ethyl or hydroxyethyl and most preferably methyl. X is S or Se, and is preferably S. Q is an organic grouping, usually of biochemical origin such as a sugar, peptide, amino acid, or steroid. However, Q can also be a non-biochemical moiety, such as a carboxylic acid moiety. The organic arsenicals of the present invention have at least one carboxylic acid group separated by one or two carbon atoms from X. These compounds can be described by:

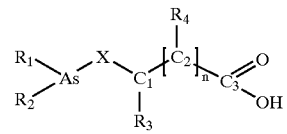

wherein $R_1$ & $R_2$ are the same as in the previous structure; $R_3$ is —COOH, —CH$_2$—COOH, —CH$_2$—CH$_2$—COOH, —CH(CH$_3$)—COOH, —CH(CH$_2$—CH$_3$)—COOH, —CH$_2$—CH$_2$—CH$_2$—COOH, or $R_3$ forms an aromatic ring or substituted aromatic ring comprising $R_4$, $C_1$ and $C_2$; n is 0 or 1; and $R_4$ is —H—CH$_3$, or is part of an aromatic ring. Part of an aromatic ring is defined herein as an atom that is bonded to two or more other atoms in an aromatic ring system.

Compounds of particular relevance to the present invention include S-dimethylarsino-thiosuccinic acid (MER1), S-dimethylarsino-2-thiobenzoic acid (SAL-1), and S-(dimethylarsino) glutathione (SGLU1). The present inventors have shown that MER1, SAL-1, and SGLU1 exert significant anti-cancer activity against a panel of human leukemia cell lines. This observation has been confirmed and extended to the activity against human solid tumor cell lines as well (>60 cell lines in total) by the experiments done at the National Institute of Health. In addition, MER1 and SGLU1 showed significant activity against blood tumor cells from patients with leukemia. When compared to the activity of the arsenic trioxide, MER1, SAL1, and SGLU1showed similar efficacy. MER1 and SGLU1 also showed low toxicity against nonmalignant blood mononuclear cells (obtained from normal donors). Furthermore, MER1 and SGLU1 showed less toxicity toward normal blood mononuclear cells than arsenic trioxide.

III. Toxicity of Inorganic vs. Organic Arsenicals

The use of arsenic trioxide is limited by its toxicity. OA, on the other hand, are much less toxic, to the extent that the methylation of inorganic arsenic in vivo into OA has been considered a detoxification reaction. The OA monomethylarsinic acid and dimethylarsinic acid are the primary metabolites of inorganic arsenic (Hughes et al., 1998).

Inorganic arsenicals, including arsenic trioxide, have varied effects on many organ systems, including cardiovascular system, gastrointestinal tract, kidneys, skin, nervous system, and blood. Inorganic arsenicals are particularly toxic to the liver, causing infiltration, central necrosis, and cirrhosis (IARC, 1980: ACGIH, 1991; Beliles et al., 1994; Goyer et al., 1996). There is now sufficient evidence that inorganic arsenic compounds are skin and lung carcinogens in humans (Goyer et al., 1996).

The toxicity of a given arsenical is related to the rate of its clearance from the body and to the extent of its tissue accumulation (Beliles et al., 1994). In general, toxicity increases in the following sequence: organic arsenicals $<As^{5+}<As^{3+}$ (including arsenic trioxide)<arsine. Unlike inorganic arsenicals, no deaths or serious cases of toxicity due to OA have been reported in the literature. Consequently, in mammals the methylation of inorganic arsenic has been considered a detoxification reaction because of the lower toxicity of methylated OA, and their fast excretion and low retention (Beliles et al., 1994; Goyer et al., 1996). A good example is that of dimethylarsinic acid, an organic compound, the predominant urinary metabolite excreted by most mammals after exposure to inorganic arsenic, including arsenic trioxide. In in vivo toxicity studies in mice, after intraperitoneal administration of arsenic trioxide, the $LD_{50}$ (a dose at which 50% of animals die due to acute toxicity) was 10 mg/kg, (Investigator's Brochure, 1998), while after administration of dimethylarsinic acid, the $LD_{50}$ was 500 mg/kg (MSDS, 1998).

IV. Cancer Treatment

The organic arsenicals of the current invention may be used to treat a variety of cancers, including all solid tumors and all hematological cancers, including leukemia, lymphoma, multiple myeloma, myelodysplasia, or myeloproliferative disorders. The OA can also be used to treat hematological cancers that have become refractory to other forms of treatment.

Leukemia is a malignant neoplasm of blood-forming tissues, characterized by abnormal proliferation of leukocytes and is one of the four major types of cancer. Leukemias are classified according to the type of leucocyte most prominently involved. Acute leukemias are predominantly undifferentiated cell populations and chronic leukemias have more mature cell forms (WO9924029).

The acute leukemias are divided into lymphoblastic (ALL) and non-lymphoblastic (ANLL) types and may be further subdivided by morphologic and cytochemical appearance according to the French-American-British classification or according to their type and degree of differentiation. Specific B- and T-cell, as well as myeloid cell surface markers/antigens are used in the classification too. ALL is predominantly a childhood disease while ANLL, also known as acute myeloid leukemia, is a more common acute leukemia among adults.

Chronic leukemias are divided into lymphocytic (CLL) and myeloid (CML) types. CLL is characterized by the increased number of mature lymphocytes in blood, bone marrow, and lymphoid organs. Most CLL patients have clonal expansion of lymphocytes with B cell characteristics. CLL is a disease of older persons. In CML, the granulocytic cells predominate at all stages of differentiation in blood and bone marrow, but may also affect liver, spleen, and other organs. Other malignant hematological disease that may be treated with the OA of the current invention, include, but are not limited to: myelodysplasia, myeloproliferative diseases, lymphomas, and multiple myeloma.

V. Pharmaceutical Preparations

Pharmaceutical compositions of the present invention comprise an effective amount of one or more organic arsenic derivative, or more particularly s-dialkyl-thio acetic acids such as MER-1, SAL1 or SGLU1 or a salt or a derivative of MER1, SAL1 or SGLU1, or additional agent dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. The preparation of an pharmaceutical composition that contains at least one organic arsenical or additional active ingredient will be known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289–1329, incorporated herein by reference). Except insofar as any conventional carrier is incompatible with the active ingredient, its use in the therapeutic or pharmaceutical compositions is contemplated.

The organic arsenical may comprise different types of carriers depending on whether it is to be administered in solid, liquid or aerosol form, and whether it need to be sterile for such routes of administration as injection. The present invention can be administered intravenously, intradermally, intraarterially, intraperitoneally, intralesionally, intracranially, intraarticularly, intraprostaticaly, intrapleurally, intratracheally, intranasally, intravitreally, intravaginally, intrarectally, topically, intratumorally, intramuscularly, intraperitoneally, subcutaneously, subconjunctival, intravesicularlly, mucosally, intrapericardially, intraumbilically, intraocularally, orally, topically, locally, injection, infusion, continuous infusion, localized perfusion bathing target cells directly, via a catheter, via a lavage, in lipid compositions (e.g., liposomes), or by other method or any combination of the forgoing as would be known to one of ordinary skill in the art (see, for example, Remington's Pharmaceutical Sciences, 18th Ed. Mack Printing Company, 1990, incorporated herein by reference).

The actual dosage amount of a composition of the present invention administered to a patient can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an organic arsenical compound. In other embodiments, the an active compound may comprise between about 2% to about 75% of the weight of the unit, or between about 25% to about 60%, for example, and any range derivable therein. In other non-limiting examples, a dose may also comprise from about 0.1 mg/kg/body weight, 0.5 mg/kg/body weight, 1 mg/kg/body weight, about 5 mg/kg/body weight, about 10 mg/kg/body weight, about 20 mg/kg/body weight, about 30 mg/kg/body weight, about 40 mg/kg/body weight, about 50 mg/kg/body weight, about 75 mg/kg/body weight, about 100 mg/kg/body weight, about 200 mg/kg/body weight, about 350 mg/kg/body weight, about 500 mg/kg/body weight, about 750 mg/kg/body weight, to about 1000 mg/kg/body weight or more per administration, and any range derivable therein. In non-limiting examples of a derivable range from the numbers listed herein, a range of about 10 mg/kg/body weight to about 100 mg/kg/body weight, etc., can be administered, based on the numbers described above.

In any case, the composition may comprise various antioxidants to retard oxidation of one or more component. Additionally, the prevention of the action of microorganisms can be brought about by preservatives such as various antibacterial and antifungal agents, including, but not limited to parabens (e.g., methylparabens, propylparabens), chlorobutanol, phenol, sorbic acid, thimerosal or combinations thereof.

The organic arsenical may be formulated into a composition in a free base, neutral or salt form. Pharmaceutically acceptable salts include the salts formed with the free carboxyl groups derived from inorganic bases such as for example, sodium, potassium, ammonium, calcium or ferric hydroxides; or such organic bases as isopropylamine, trimethylamine, histidine or procaine.

In embodiments where the composition is in a liquid form, a carrier can be a solvent or dispersion medium comprising, but not limited to, water, ethanol, polyol (e.g., glycerol, propylene glycol, liquid polyethylene glycol, etc.), lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof such methods. In many cases, it will be preferable to include isotonic agents, such as, for example, sugars, sodium chloride or combinations thereof.

Sterile injectable solutions are prepared by incorporating the active compounds in the required amount of the appropriate solvent with various of the other ingredients enumerated above, as required, followed by filtered sterilization. Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsion, the preferred methods of preparation are vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The preparation of highly concentrated compositions for direct injection is also contemplated, where the use of DMSO as solvent is envisioned to result in extremely rapid penetration, delivering high concentrations of the active agents to a small area.

The composition must be stable under the conditions of manufacture and storage, and preserved against the contaminating action of microorganisms, such as bacteria and fingi. It will be appreciated that endotoxin contamination should be kept minimally at a safe level, for example, less that 0.5 ng/mg protein.

In particular embodiments, prolonged absorption of an injectable composition can be brought about by the use in the compositions of agents delaying absorption, such as, for example, aluminum monostearate, gelatin or combinations thereof.

VI. Combination Therapy

It is an aspect of this invention that the organic arsenical can be used in combination with another agent or therapy method, preferably another cancer treatment. The organic arsenical may precede or follow the other agent treatment by intervals ranging from minutes to weeks. In embodiments where the other agent and expression construct are applied separately to the cell, one would generally ensure that a significant period of time did not expire between the time of each delivery, such that the agent and expression construct would still be able to exert an advantageously combined effect on the cell. For example, in such instances, it is contemplated that one may contact the cell, tissue or organism with two, three, four or more modalities substantially simultaneously (i.e., within less than about a minute) with the organic arsenical. In other aspects, one or more agents may be administered within about 1 minute, about 5 minutes, about 10 minutes, about 20 minutes about 30 minutes, about 45 minutes, about 60 minutes, about 2 hours, about 3 hours, about 4 hours, about 5 hours, about 6 hours, about 7 hours about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, about 25 hours, about 26 hours, about 27 hours, about 28 hours, about 29 hours, about 30 hours, about 31 hours, about 32 hours, about 33 hours, about 34 hours, about 35 hours, about 36 hours, about 37 hours, about 38 hours, about 39 hours, about 40 hours, about 41 hours, about 42 hours, about 43 hours, about 44 hours, about 45 hours, about 46 hours, about 47 hours, to about 48 hours or more prior to and/or after administering the organic arsenical. In certain other embodiments, an agent may be administered within of from about 1 day, about 2 days, about 3 days, about 4 days, about 5 days, about 6 days, about 7 days, about 8 days, about 9 days, about 10 days, about 11 days, about 12 days, about 13 days, about 14 days, about 15 days, about 16 days, about 17 days, about 18 days, about 19 days, about 20, to about 21 days prior to and/or after administering the organic arsenical. In some situations, it may be desirable to extend the time period for treatment significantly, however, where several weeks (e.g., about 1, about 2, about 3, about 4, about 5, about 6, about 7 or about 8 weeks or more) lapse between the respective administrations.

Various combinations may be employed, the organic arsenical is "A" and the secondary agent, which can be any other therapeutic agent, is "B":

A/B/A B/A/B B/B/A A/A/B A/B/B B/A/A A/B/B/B B/A/B/B

B/B/B/A B/B/A/B A/A/B/B A/B/A/B A/B/B/A B/B/A/A

B/A/B/A B/A/A/B A/A/A/B B/A/A/A A/B/A/A A/A/B/A

Administration of the therapeutic compositions of the present invention to a patient will follow general protocols for the administration of chemotherapeutics, taking into account the toxicity, if any. It is expected that the treatment cycles would be repeated as necessary. It also is contemplated that various standard therapies or adjunct cancer therapies, as well as surgical intervention, may be applied in combination with the described arsenical agent. These therapies include but are not limited to chemotherapy, radiotherapy, immunotherapy, gene therapy and surgery. The section below describes some adjunct cancer therapies:

a. Chemotherapy

Cancer therapies also include a variety of combination therapies with both chemical and radiation based treatments. Combination chemotherapies include, for example, cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, gemcitabien, navelbine, farnesyl-protein tansferase inhibitors, transplatinum, 5-fluorouracil, vincristin, vinblastin and methotrexate, or any analog or derivative variant of the foregoing.

b. Radiotherapy

Other factors that cause DNA damage and have been used extensively include what are commonly known as γ-rays, X-rays, and/or the directed delivery of radioisotopes to tumor cells. Other forms of DNA damaging factors are also contemplated such as microwaves and V-irradiation. It is most likely that all of these factors effect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells. The terms "contacted" and "exposed," when applied to a cell, are used herein to describe the process by which a therapeutic construct and a chemotherapeutic or radiotherapeutic agent are delivered to a target cell or are placed in direct juxtaposition with the target cell. To achieve cell killing or stasis, both agents are delivered to a cell in a combined amount effective to kill the cell or prevent it from dividing.

c. Immunotherapy

Immunotherapeutics, generally, rely on the use of immune effector cells and molecules to target and destroy cancer cells. The immune effector may be, for example, an antibody specific for some marker on the surface of a tumor cell. The antibody alone may serve as an effector of therapy or it may recruit other cells to actually effect cell killing. The antibody also may be conjugated to a drug or toxin (chemotherapeutic, radionucleotide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells.

Immunotherapy, thus, could be used as part of a combined therapy, in conjunction with gene therapy. The general approach for combined therapy is discussed below. Generally, the tumor cell must bear some marker that is amenable to targeting, i.e., is not present on the majority of other cells. Many tumor markers exist and any of these may be suitable for targeting in the context of the present invention. Common tumor markers include carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B and p155.

d. Gene Therapy

In yet another embodiment, the secondary treatment is a secondary gene therapy in which a therapeutic polynucleotide is administered before, after, or at the same time a first therapeutic agent. Delivery of the therapeutic agent in conjunction with a vector encoding a gene product will have a combined anti-hyperproliferative effect on target tissues.

e. Surgery

Approximately 60% of persons with cancer will undergo surgery of some type, which includes preventative, diagnostic or staging, curative and palliative surgery. Curative surgery is a cancer treatment that may be used in conjunction with other therapies, such as the treatment of the present invention, chemotherapy, radiotherapy, hormonal therapy, gene therapy, immunotherapy and/or alternative therapies. Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and miscopically controlled surgery (Mohs' surgery). It is further contemplated that the present invention may be used in conjunction with removal of superficial cancers, precancers, or incidental amounts of normal tissue.

VII. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Synthesis of S-dimethylarsino-thiosuccinic acid (MER1), S-dimethylarsino-Salicylic acid (SAL1), and S-(dimethylarsino)glutathione (SGLU1)

MER-1: Mercaptosuccinic acid, 4.5 g, was placed in 100 ml of glyme (1,2-dimethoxyethane) in a 250 ml round-bottom flask. Four ml of dimethylchloroarsine (0.03 mol) was added drop-wise, followed by 4 ml of diethylamine (0.04 mol), again drop-wise. The reaction mixture was stirred for 20 h at room temperature. A white precipitate of diethylamine hydrochloride-was formed and was separated by filtration. The solution of MER1 in the glyme was greatly reduced in volume by evaporation at reduced pressure. White crystals of MER1 were separated by filtration and washed with cold distilled water. The colorless crystalline product was then recrystallized from ethanol-water to a constant melting point of 150° C.

SAL-1: In a 100 ml flask 5 g of 2-mercapto benzoic acid (thiosalicylic acid), 75 ml of glyme, 5 ml of dimethylchloroarsine, and 5 ml diethylamine were placed. The mixture was refluxed for 1 hour under an atmosphere of nitrogen and stirred at room temperature overnight. The precipitate of diethylamine hydrochloride was separated by filtration. The filtrate was evaporated slowly under reduced pressure until crystals of the product separate. The evaporated solution containing the product was chilled in ice and the cold solution was filtered. Crystals of the product were recrystallized from ethanol to a constant melting point of 97° C.

SGLU-1: Glutathione (14.0 g, 45.6 mmol) was stirred rapidly in glyme while dimethylchoroarsine (6.5 g, 45.6 mmol) was added dropwise. Pyridine (6.9 g, 91.2 mmol) was then added to the slurry and the mixture was subsequently heated to reflux. The heat was removed immediately and the mixture stirred at room temperature for 4 h. Isolation of the resultant insoluble solid and recrystallization from ethanol afforded 4 as the pyridinium hydrochloride (75% yield): mp 115–118° C.; NMR (D2O) δ1.35 (s, 6H), 1.9–4.1 (m's, 10H), 7.8–9.0 (m, 5H); mass spectrum (m/e) 140, 125, 110, 105, 79, 52, 45, 36.

The studies that let to the synthesis of MER-1, SGLU-1 and SAL-1 were funded by the Robert A. Welch foundation of Houston, Tex., in a grant to inventor Ralph Zingaro.

Example 2

Assay for In Vitro Evaluation

A variety of in vitro assays were used to determine the response of cancer cells to the arsenical compounds, compositions, and/or formulations of the present invention. Some of the responses assayed included cell survival, cell cycle, apoptosis, and maturation. The present inventors also designed an assay to evaluate the requirement of the PML/RARalpha gene in cancer cells for sensitivity to the arsenical compositions of the invention. Provided below is a description of these assays:

Sulforhodamine B Assay. Various human cancer cells were incubated on a microtiter plate with or without indicated concentrations of MER1, SAL1 or SGLU1 for 48 hours, and then sulforhodamine B dye was added to the cultures. The sulforhodamine B dye is a protein binding dye and labels live cells. Results are reported as the percent growth of treated cells when compared to untreated control cells (negative data indicate cell kill).

MTT and Trypan Blue Assays. For these assays mononuclear cells from peripheral blood samples of leukemia patients and normal donors were separated by Ficoll Hipaque fractionation and resuspended in DMEM complete medium. Alternatively, cell line cells were used in some cases. Malignant cells from various human cell lines (usually at $5\times10^4$ cells/ml) or mononuclear cells from peripheral blood of leukemia patients and healthy donors ($1\times10^6$ cells/ml) were incubated in either alpha MEM or RPMI 1640 with or without various concentrations of MER1, SAL1 or SGLU1. Each experimental condition was done in triplicate. After the indicated number of days (usually 3 days) of exposure to MER1, SAL1 or SGLU1, cell survival was assessed by the addition of a dye to the wells (either MTT or trypan-blue). The MTT dye changes its color depending on the presence of live cells in the well. Survival of cells under MTT treatment was evaluated as a percentage of control cell growth. The trypan-blue dye penetrates dead cells and live cells can be counted under the microscope and percentage survival estimated.

Clonogenic Assay. Clonogenicity or colony formation was analyzed by obtaining peripheral blood mononuclear cells (from normal donors or leukemia patients) which were resuspended in semisolid medium containing recombinant cytokines and plated in quadruplicate, 0.1 ml/well, in 96-well microtiter plates at $4\times10^4$ cells/0.1 ml density. Cell aggregates composed of more than 50 cells are counted as one colony after ~10 days of incubation at 37° C. in 5% $CO_2$ humidified atmosphere. Growth inhibition was evaluated as a percentage of colony growth as compared to colony growth in control (no drug) samples.

Analysis of Apoptosis. Three different methods were used to analyze apoptosis by assaying different events in the apoptotic pathways. Percentages of apoptotic cells induced by arsenic derivatives of the invention were evaluated using flow cytometer. Different methods of staining cells for apoptosis were utilized to assess different aspects of apoptotic cascade.

1. Annexin V and Propidium Iodide (PI) Staining. Annexin V binds to cells that express phosphatidylserine on the outer layer of the cell membrane, while propidium iodide stains the cellular DNA of cells with a compromised cell membrane. This allows live cells (unstained with either fluorochrome) to be discriminated from apoptotic cells (stained only with annexin V) and necrotic cells (stained with both annexin and PI).

Following treatment of cells in culture with indicated arsenicals of the invention for the indicated time, cells were washed in phosphate-buffered saline (PBS) and resuspended in 100 µl of binding buffer containing annexin V-FITC (Travigene) and incubated for 15 minutes in the dark. Cells were analyzed on flow cytometer after the addition of PI.

2. Cytofluorometric Analysis of the Mitochondrial Membrane Potential. To evaluate the changes in the potential of mitochondrial membrane, following treatment with arsenic derivatives for indicated time, cells were incubated in submicromolar concentrations of MitoTracker probes. MitoTracker probes passively diffuse across the plasma membrane and accumulate in active mitochondria. Cells were stained with two colors: MitoTracker Red CMXRos (Molecular Probes) and MitoTracker Green FM (Molecular Probes). Cells were washed in PBS, stained with MitoTracker dyes and incubated for 1 hour at 37° C. in the dark. CMXRos is incorporated into mitochondria driven by the mitochondrial membrane potential and reacts with thiol residues to form covalent thiol ester bonds. MitoTracker Green FM dye preferentially accumulates in mitochondria regardless of mitochondrial membrane potential, making it a useful tool for determining mitochondrial mass.

3. Detection of Caspase Activity. In order to monitor caspase activity by flow cytometry, the fluorogenic substrate PhiPhiLux G1D1 (Oncoimmunin) was used. PhiPhiLux G1D1 is a substrate for the detection and measurement of caspase 3 and caspase 3-like activities in living cells. Following treatment with the arsenic derivatives of the invention for indicated time, cells were washed in PBS, resuspended in 5 ul substrate solution and incubated for 1 hour at 37° C. in the dark. After incubation cells were washed, and few minutes before flow cytometry analysis, PI was added to exclude necrotic cells during analysis.

Cell Cycle Analysis. Cell cycle was analyzed as follows: After 72 h of incubation with the different arsenical compounds of the invention, cells ($1\times10^6$) were washed twice in PBS. Cell pellet was resuspended in staining solution that contained hypotonic solution (RNAse solution, Triton X-100, sodium citrate, PEG) and PI (25 µg/ml). Cells were incubated 15 minutes in dark at room temperature and then they were analyzed by flow cytometer using CellQuest program (Becton-Dickinson).

Maturation Analysis. Human acute prolymphocytic leukemia cell line NB4 was used to test the effect of the arsenicals of the invention on the maturation of leukemic cells. Phycoerythrin-conjugated anti-CD11b monoclonal antibody (Becton-Dickinson) was used as a marker of mature myelocytes. After 72 h of incubation with drugs, cells were washed in PBS. Cells in the density of $1\times10^6$ cells/ml were then incubated with monoclonal antibody in dilution 1:10 in dark at room temperature for 15 minutes. After incubation cells were washed in PBS and the pellet was resuspended in 500 µl of PBS. To exclude nonspecific binding appropriate isotypic control was prepared in the same manner. Cells were sorted using a flow cytometer and analyzed using CellQuest Document Analysis.

Role of PML/RARalpha Protein. Arsenic trioxide is approved as a treatment for acute prolymphocytic leukemia and it kills APL cells in large part due to their expression of PML/RARalpha gene and protein. To establish whether the presence of PML/RARalpha fusion protein in the leukemic cells contributes to the observed sensitivity of leukemic cells to SGLU and MER1 the present inventors used the following system: U937 cells, known to be resistant to arsenic trioxide, were transfected with PML/RARalpha gene. The transfected cells are called U937/PR9 and were kindly provided by Dr. Michael Andreeff (M.D. Anderson Cancer Center). The PML/RARalpha gene becomes functional in the presence of zinc. $Zn^{2+}$-inducible expression of the PML/RARalpha gene in the U937/PR9 cell line is described in Grignani et al. (1993). In order to establish the PML/RARalpha expression, cells were treated with 0.1 mM $ZnSO_4$ for 3 h before the addition of arsenic compounds for 72 h. PML/RARα expression is typically established at about 3 h following zinc addition to the cells and is stable for 48 hours.

Example 3

In Vitro Evaluation of Anticancer Activity of MER1, SAL1, and SGLU1

Figure 2:
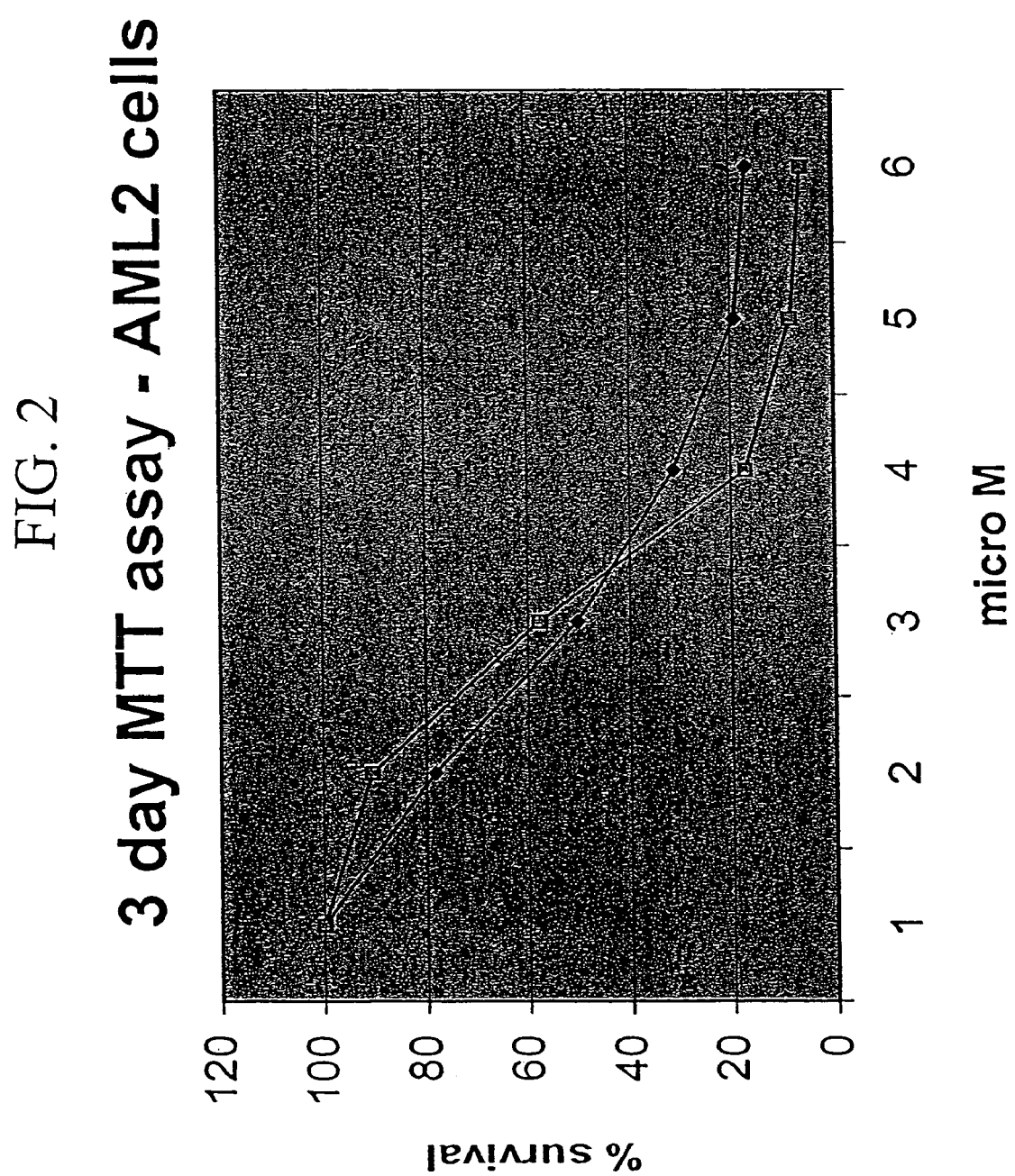
FIG. 2. The human leukemia cell line AML2 was incubated for 3 days with indicated concentrations of MER1 or arsenic trioxide. Cell survival was assessed by the trypan-blue exclusion method.
Figure 3A:
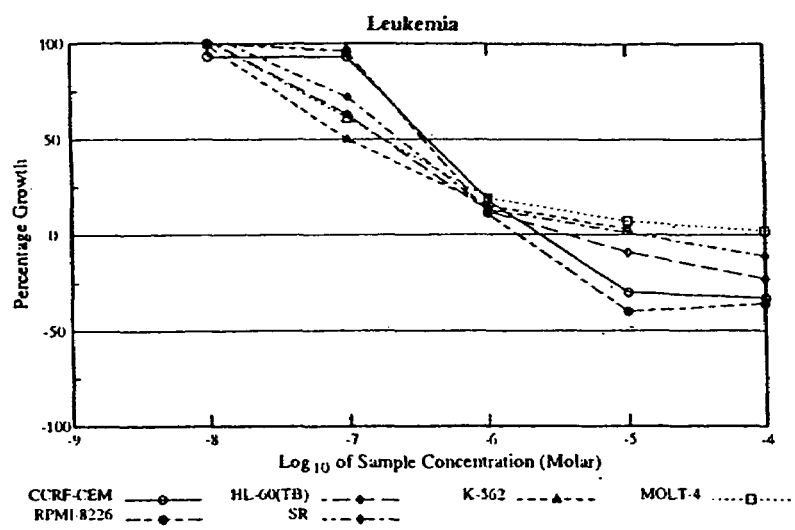
FIGS. 3A, 3B, 3C, 3D, 3E, 3F, 3G, 3H, & 3I. Percent growth for 60 human cell lines when treated with MER1. Various human cancer cells were incubated on a microtiter plate with indicated concentrations of MER1 for 48 hours. End point determinations were made with sulforhodamine B, a protein binding dye. Results are reported as the percentage of growth of treated cells when compared to untreated control cells. Negative data indicate cell kill.
Figure 3B:
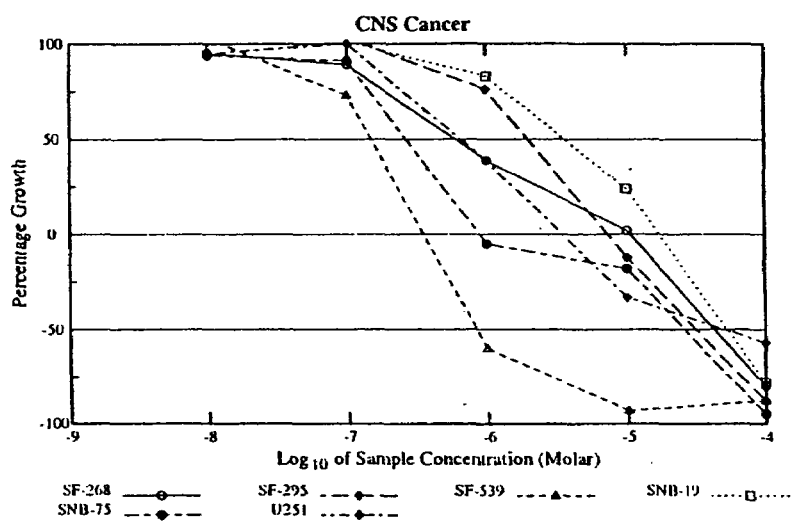
Figure 3C:
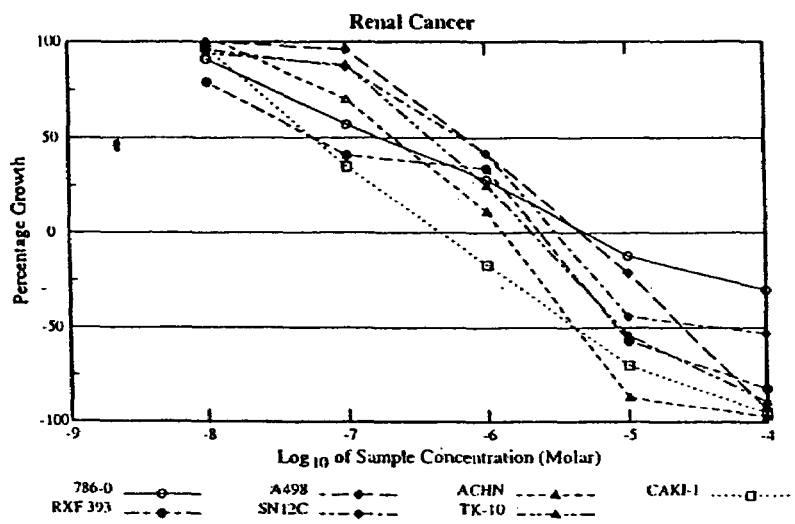
Figure 3D:
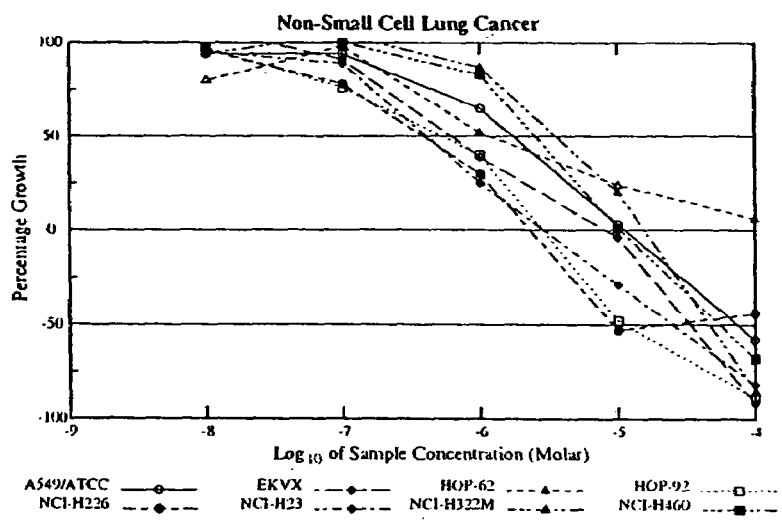
Figure 3E:
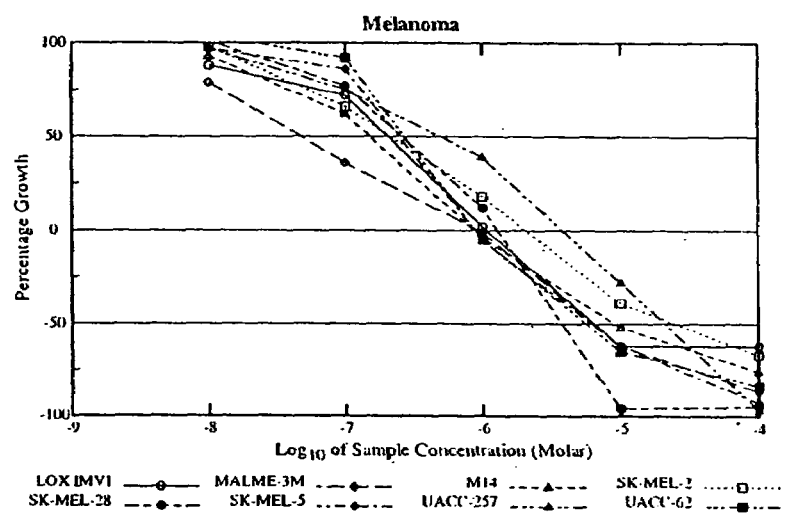
Figure 3F:
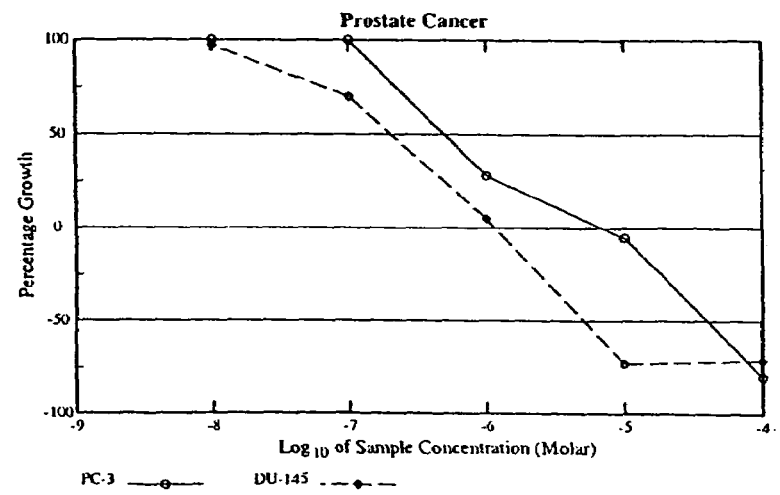
Figure 3G:
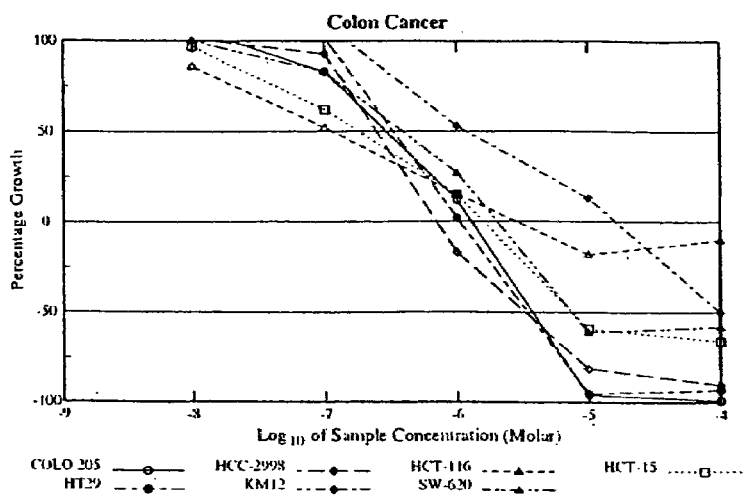
Figure 3H:
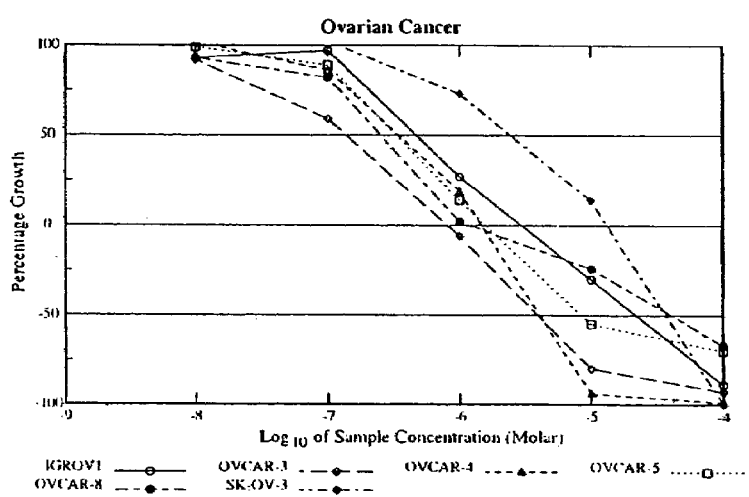
Figure 3I:
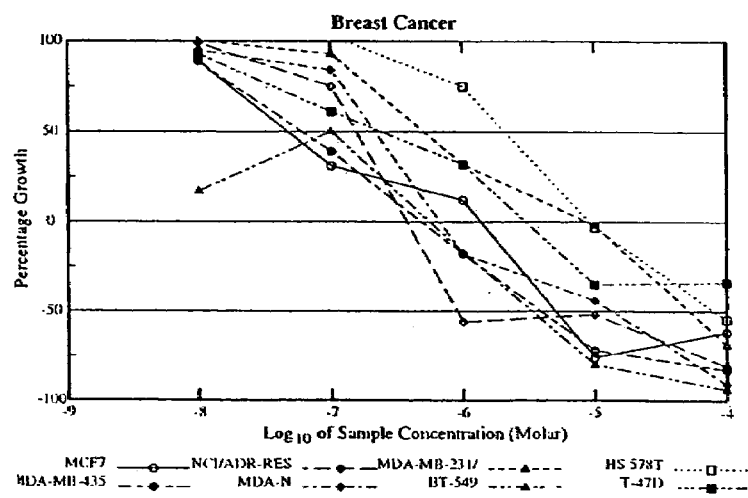

The anti-leukemic activity of MER1 has been evaluated by 3 day MTT assay/trypan blue exclusion method against 6 different human leukemia cell lines: AML2, AML3 and HL60 (an AML derived cell line), NB4 (an APL derived cell line), K562 (a CML-BP derived cell line), and KBM7 (an AML derived cell line). MER1 was most effective against NB4 cells with an $IC_{50}$ (the concentration that results in 50% survival of cells, as compared to untreated control cells) at 1 µM (FIG. 1). MER1 treatment of other cell lines, including the analysis of AML2 cells and KBM7 cells by the MTT assay and AML2 cells (see FIG. 2), AML3 cells, K562 cells, and HL60 cells by the trypan blue assay showed $IC_{50}$ between 1.5–4 µM. This activity was similar to the activity of arsenic trioxide against these cell lines (examples of arsenic trioxide activity are shown in FIG. 1 and FIG. 2). MER1 was also tested for anticancer activity by the National Institute Of Health (NIH), in vitro against a panel of 60 tumor cell lines using sulforhodamine B assay (FIG. 3). The compound showed evidence of activity at low concentrations against a variety of tumor cell lines, but particularly against leukemia cells tested. At the concentration of 1 µM of MER1, the growth of all 6 leukemia cell lines tested was significantly retarded (<20% growth; FIG. 3, first panel).

Figure 4:
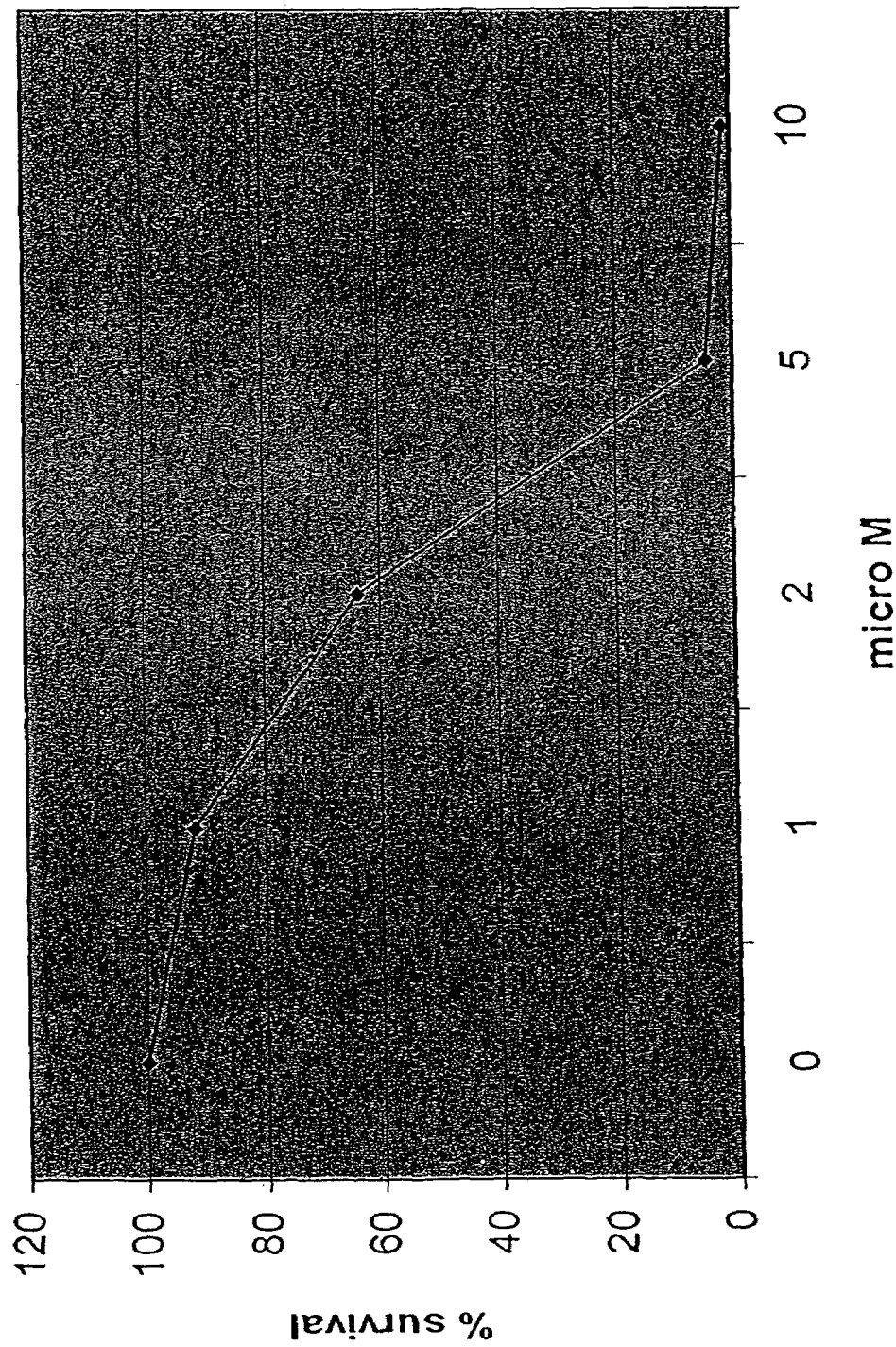
FIG. 4. HL60 human leukemia cells were incubated for 3 days with indicated concentrations of S-dimethylarsino-2-thiobenzoic acid (SAL1). Cell survival was assessed by trypan-blue exclusion method.
Figure 5A:
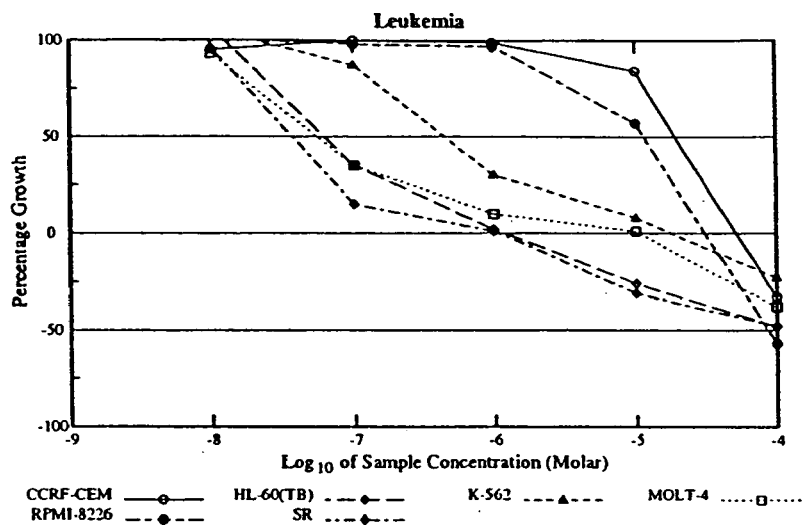
FIGS. 5A, 5B, 5C, 5D, 5E, 5F, 5G, 5H, & 5I. Percentage growth for 60 human cell lines when treated with SAL1. Various human cancer cells were incubated on a microtiter plate with indicated concentrations of SAL1 for 48 hours. End point determinations were made with sulforhodamine B, a protein binding dye. Results are reported as the percentage of growth of treated cells when compared to untreated control cells. Negative data indicate cell kill.
Figure 5B:
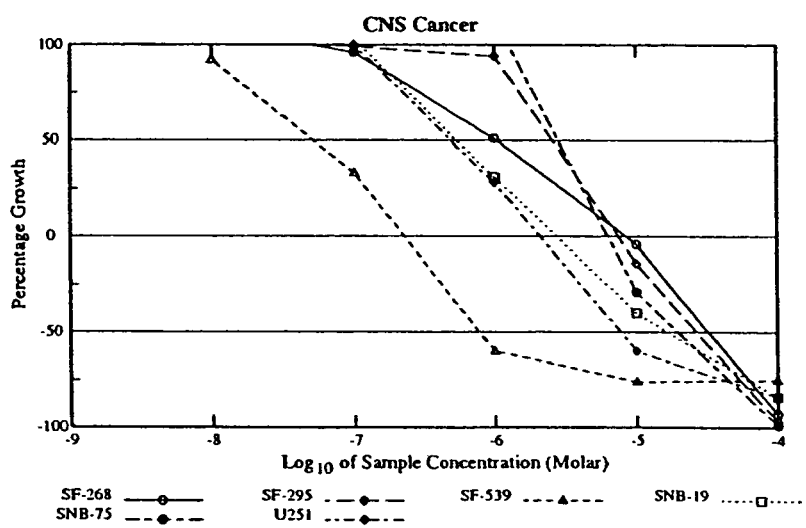
Figure 5C:
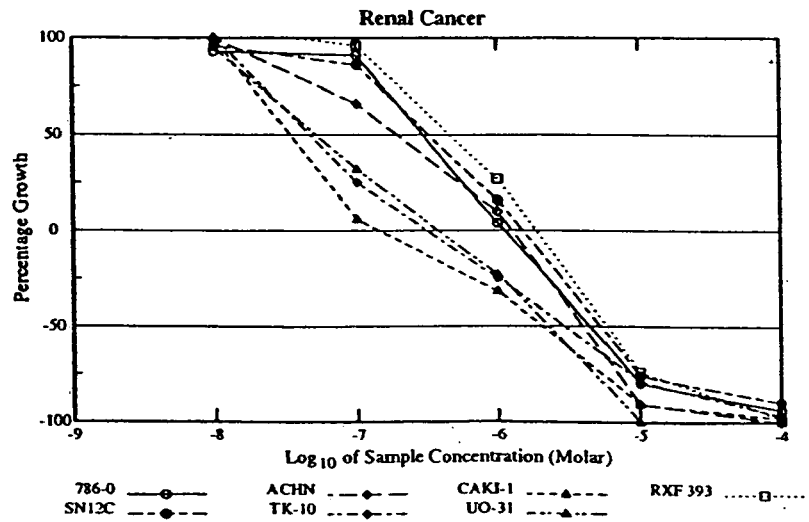
Figure 5D:
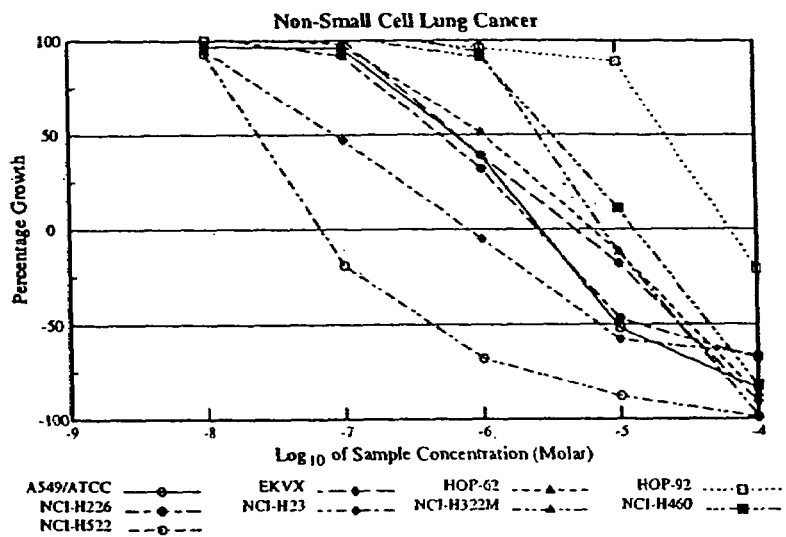
Figure 5E:
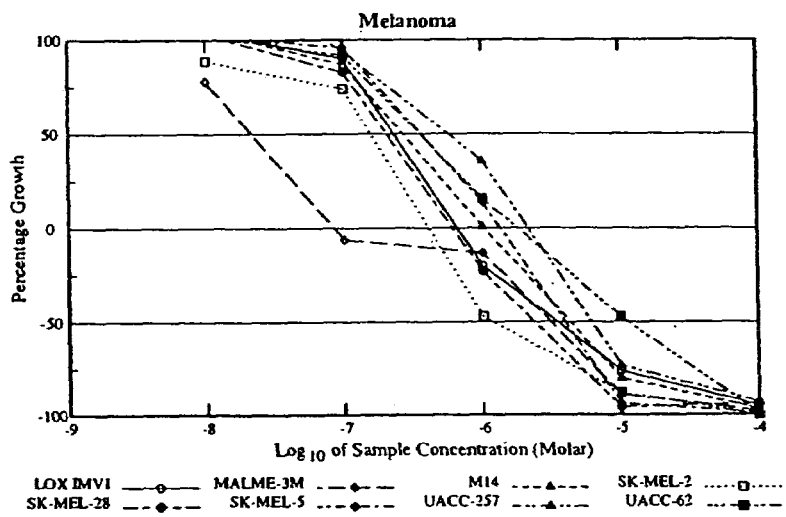
Figure 5F:
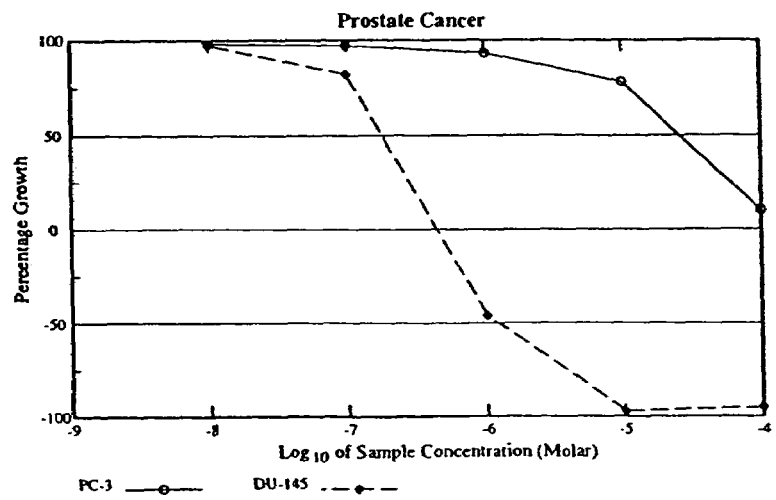
Figure 5G:
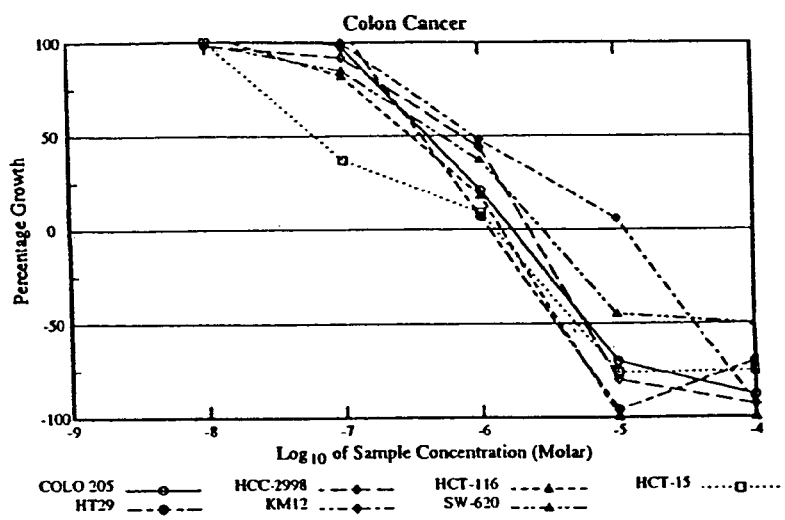
Figure 5H:
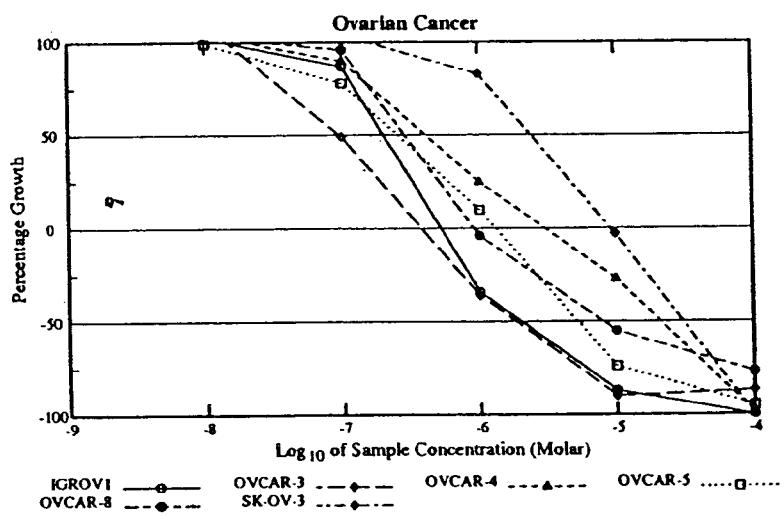
Figure 5I:
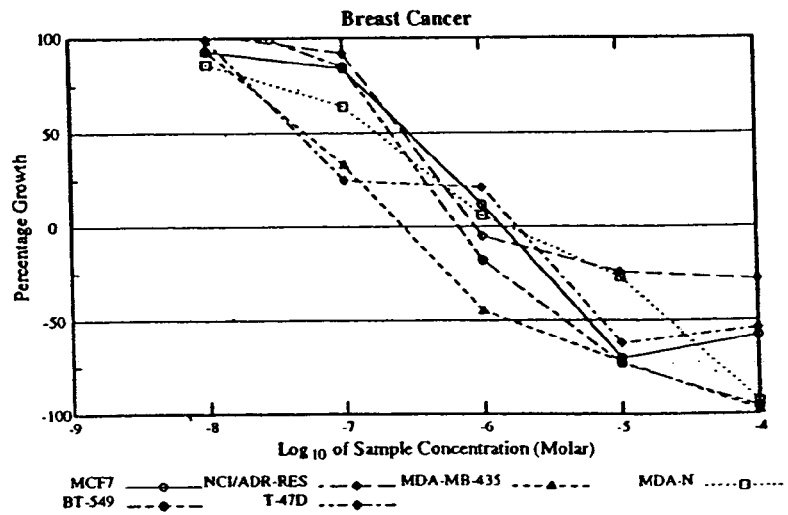

The antileukemic activity of SAL1 has been evaluated by 3 day trypan blue assays against 2 human cell lines: HL60 cells (depicted in FIG. 4), and Z138 (an ALL cell line). SAL1 was also tested for anticancer activity by the NIH in vitro against a panel of 60 tumor cell lines using sulforhodamine B assay (FIG. 5). The compound showed evidence of activity at low concentrations against a variety of tumor cell lines.

Figure 6:
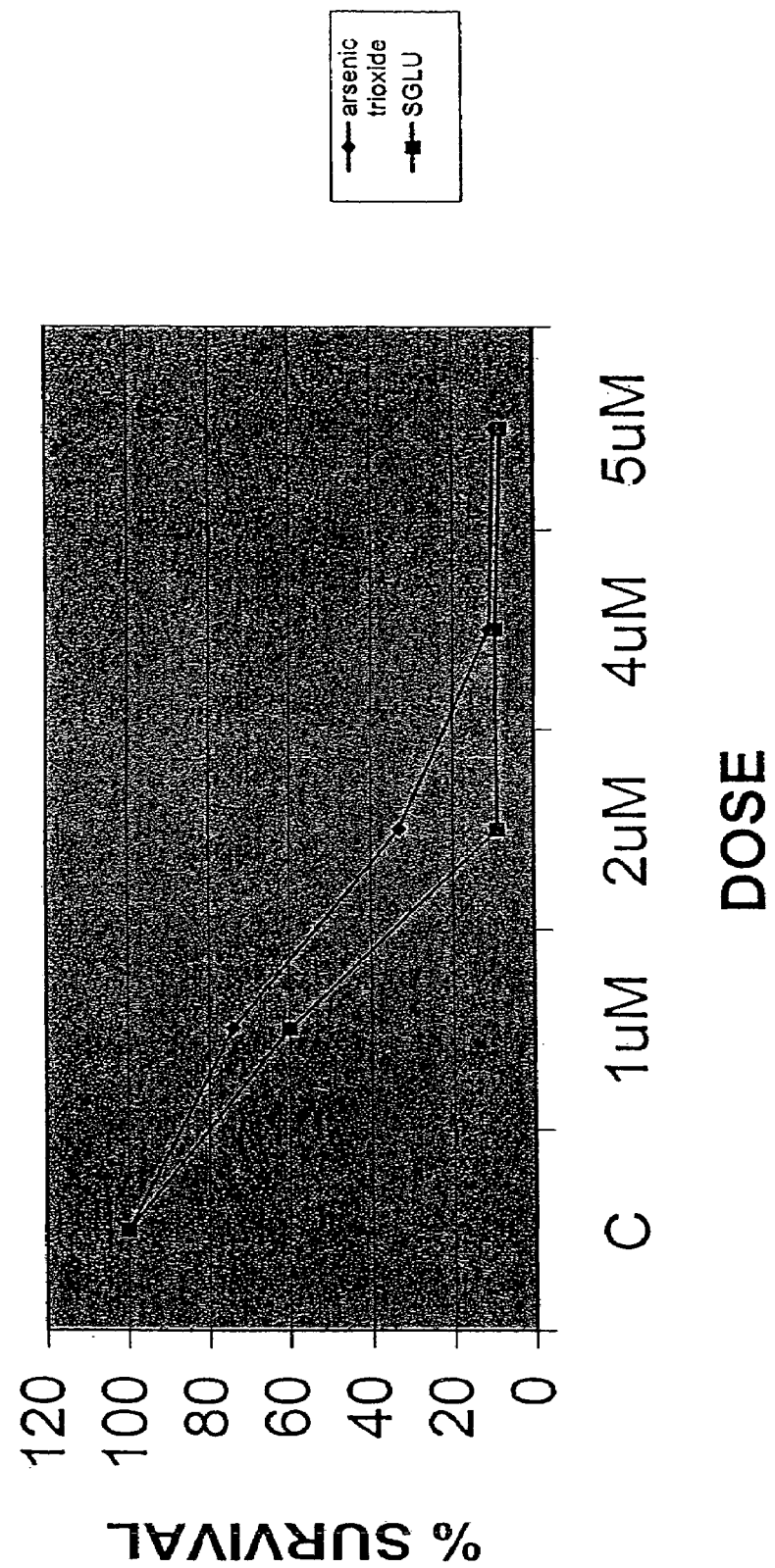
FIG. 6. NB4 cells were incubated for 3 days with indicated concentrations of S-dimethylarsino-glutathione (SGLU1) or arsenic trioxide. Cell survival was assessed by the MTT assay.
Figure 7:
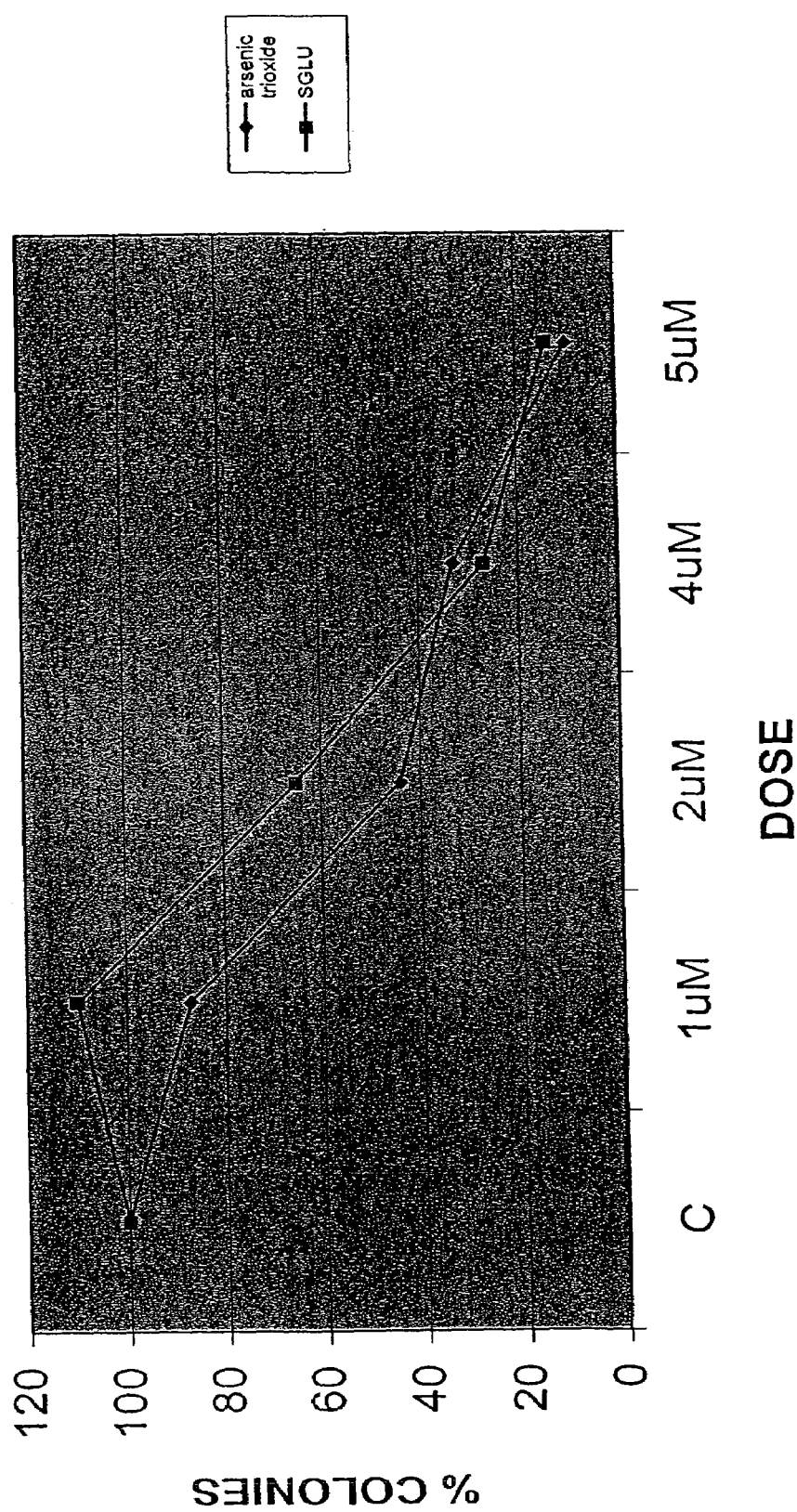
FIG. 7. A five day clonogenic assay was performed using HL60 cells and SGLU1 or arsenic trioxide. Cell aggregates composed of more than 50 cells were counted as one colony and growth inhibition was evaluated as a percentage of colony growth as compared to colony growth in control (no drug) samples.
Figure 8A:
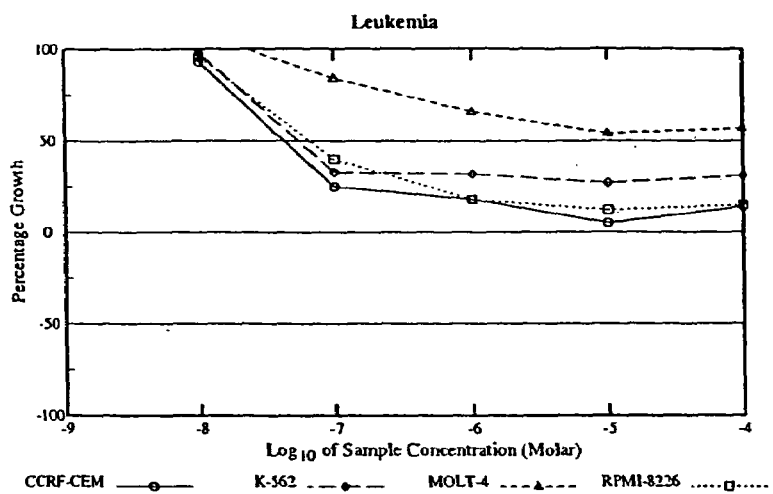
FIGS. 8A, 8B, 8C, 8D, 8E, 8F, 8G, 8H, & 8I. Percent growth for 60 human cell lines when treated with SGLU1. Various human cancer cells were incubated on a microtiter plate with indicated concentrations of SGLU1 for 48 hours. End point determinations were made with sulforhodamine B, a protein binding dye. Results are reported as the percentage of growth of treated cells when compared to untreated control cells. Negative data indicate cell kill.
Figure 8B:
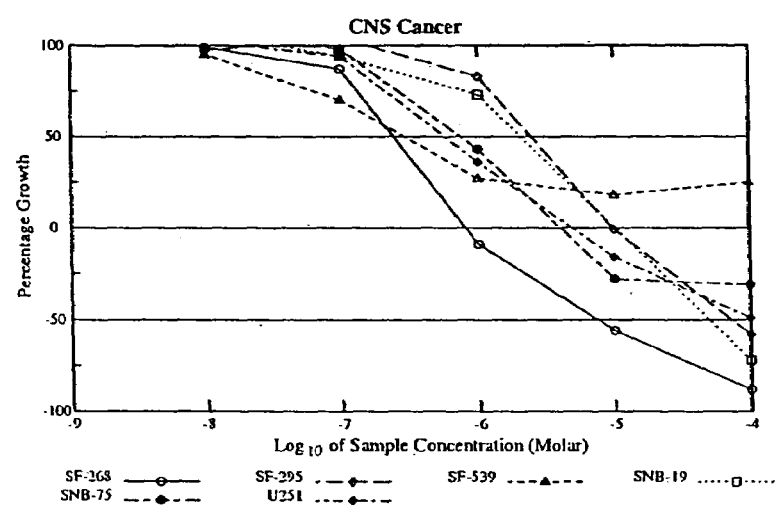
Figure 8C:
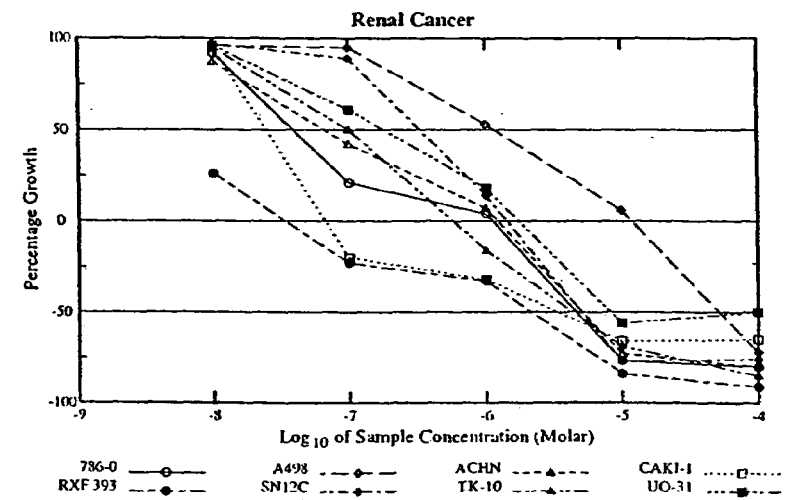
Figure 8D:
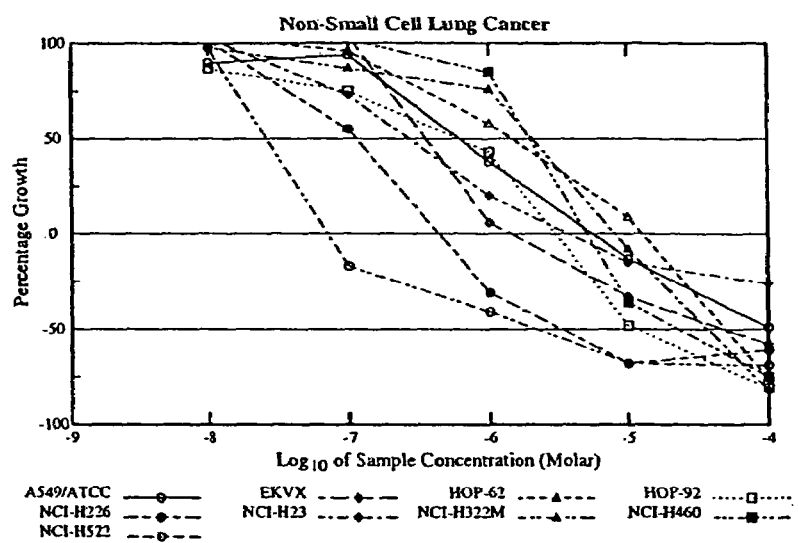
Figure 8E:
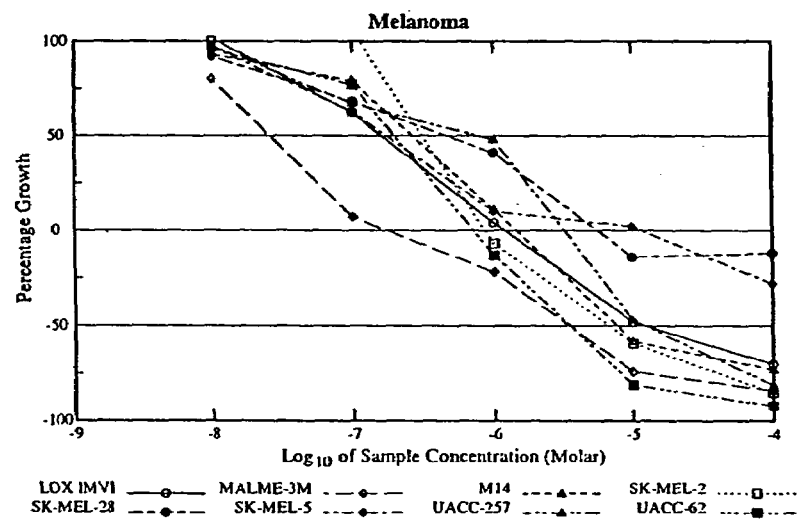
Figure 8F:
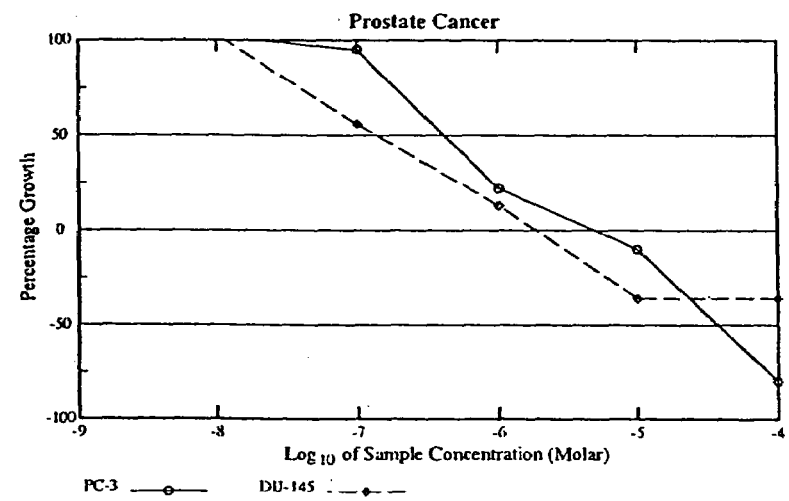
Figure 8G:
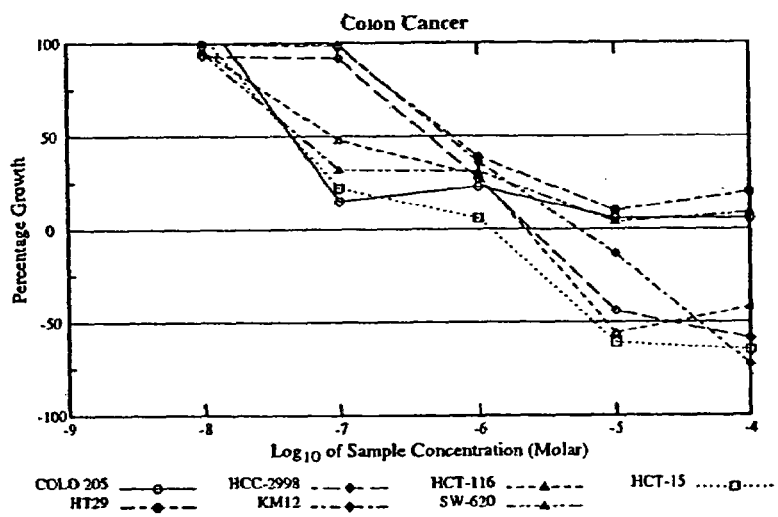
Figure 8H:
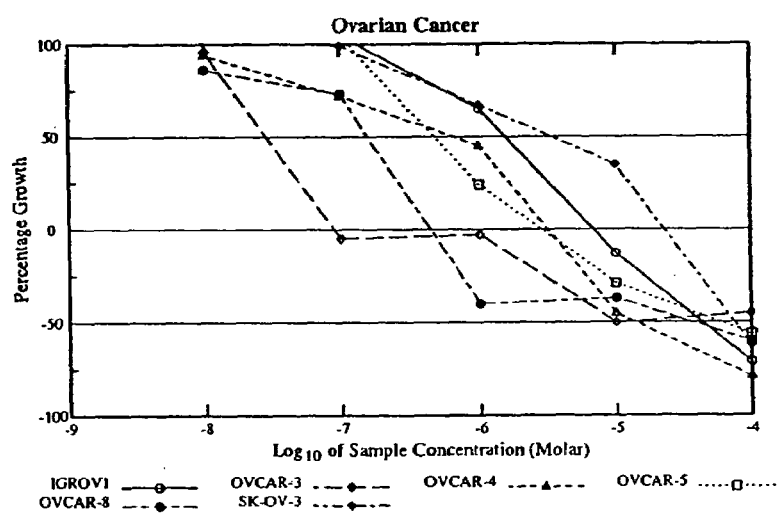
Figure 8I:
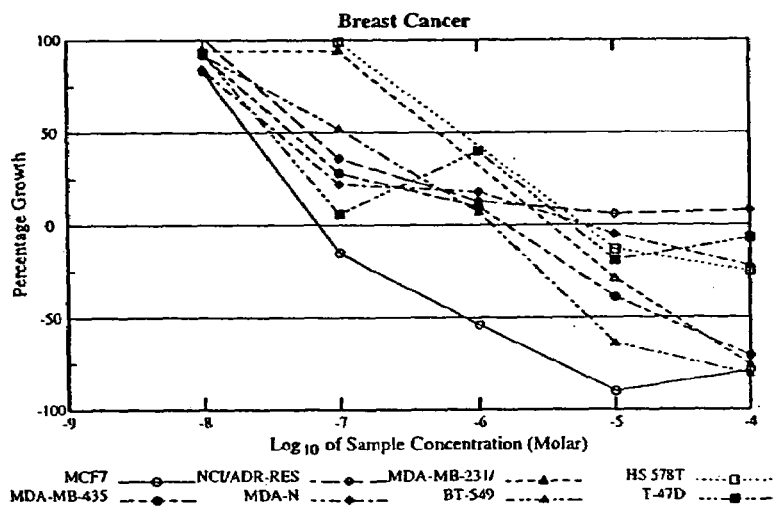

The antileukemic activity of SGLU1 has been evaluated by 3 day MTT assay against 9 human leukemia cell lines: NB4, CAG (multiple myeloma cell line), JURKAT and RAJI (lymphoma cell line), HL60, AML2, AML3, KBM5 (CML-BP derived cell line, and KBM7. The results for the cell line NB4 are depicted in FIG. 6, as an example. The antileukemic activity of SGLU1 has also been evaluated by 3 day trypan blue exclusion method against 6 human leukemia cell lines: NB4, CAG, JURKAT, HL60, KBM3 (AML cell line), and Z119 (an ALL cell line), showing similar results. The activity was similar to the activity of arsenic trioxide as depicted in FIG. 6, as an example. The antileukemic activity of SGLU1 has also been evaluated by 5 day clonogenic assay against HL60 human leukemia cells (FIG. 7). SGLU1 was also tested for anticancer activity by the NIH in vitro against a panel of 60 tumor cell lines using sulforhodamine B assay (FIG. 8). The compound showed evidence of activity at low concentrations against a variety of tumor cell lines.

Example 4

Figure 9:
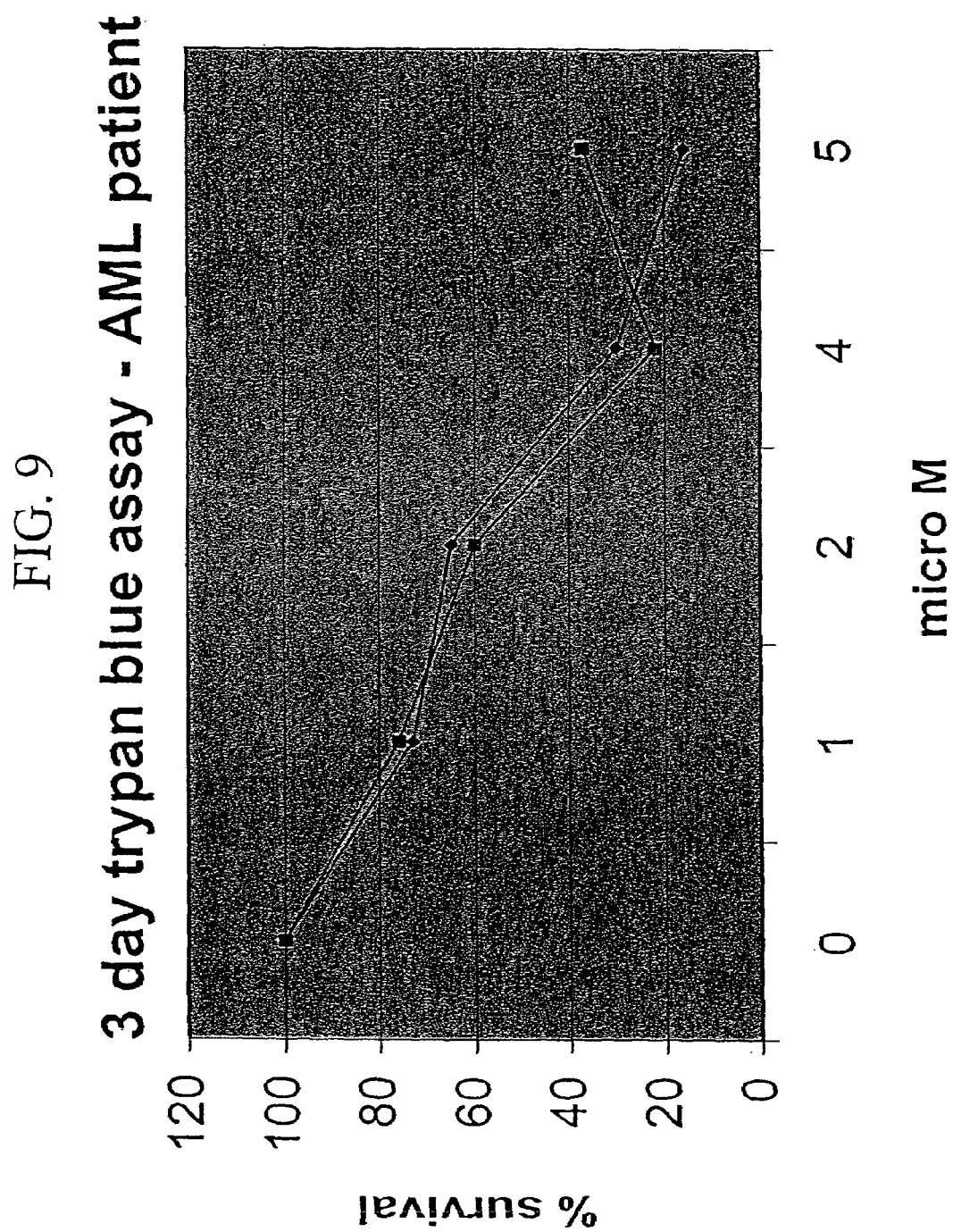
FIG. 9. Mononuclear cells from acute myeloid leukemia (AML) patient were incubated for 3 days with indicated concentrations of MER1 or arsenic trioxide. Cell survival was assessed by trypan-blue exclusion method.
Figure 10:
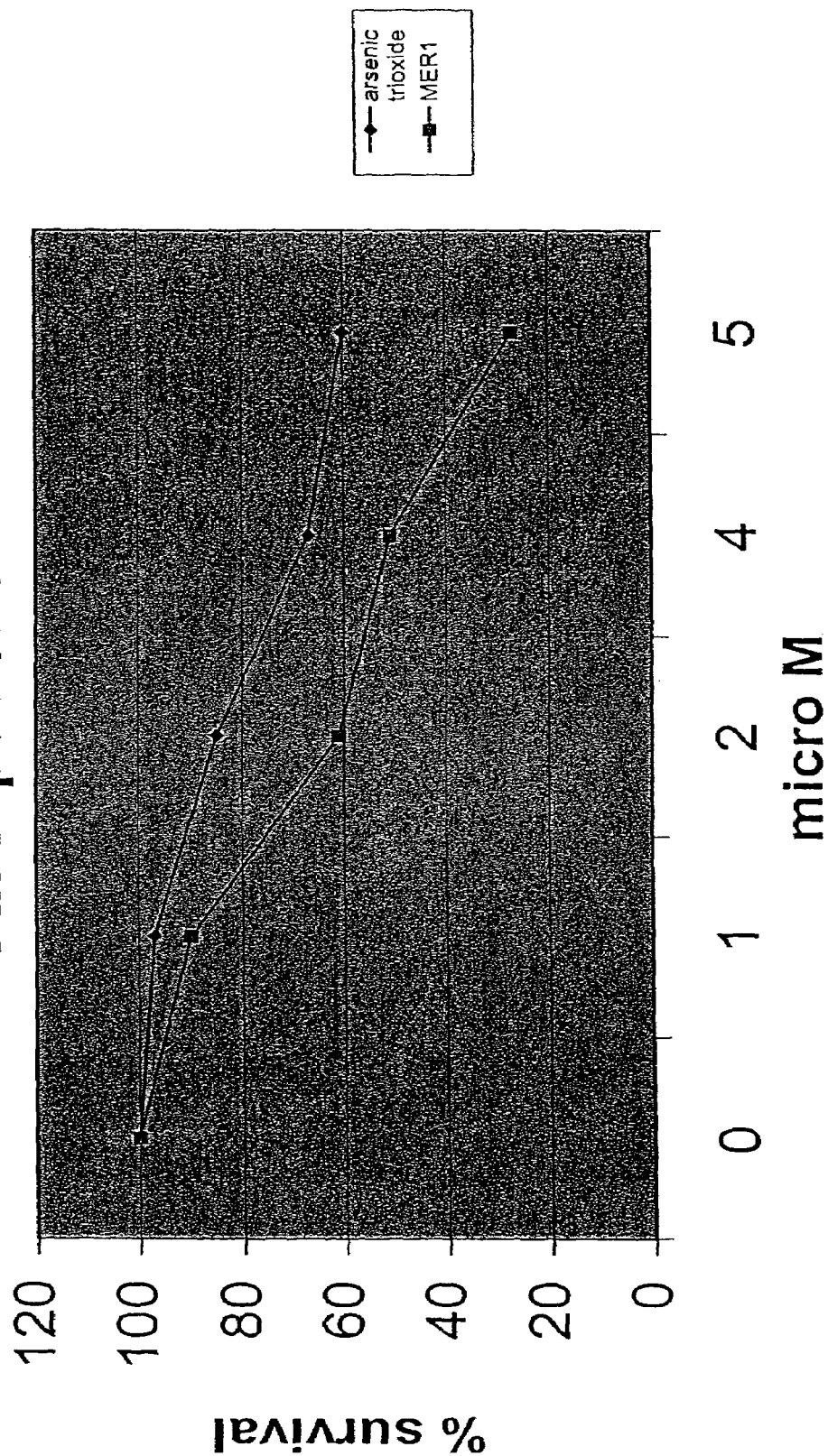
FIG. 10. Mononuclear cells from AML patient were incubated for 4 days with indicated concentrations of MER1 or arsenic trioxide. Cell survival was assessed by trypan-blue exclusion method.
Figure 11:
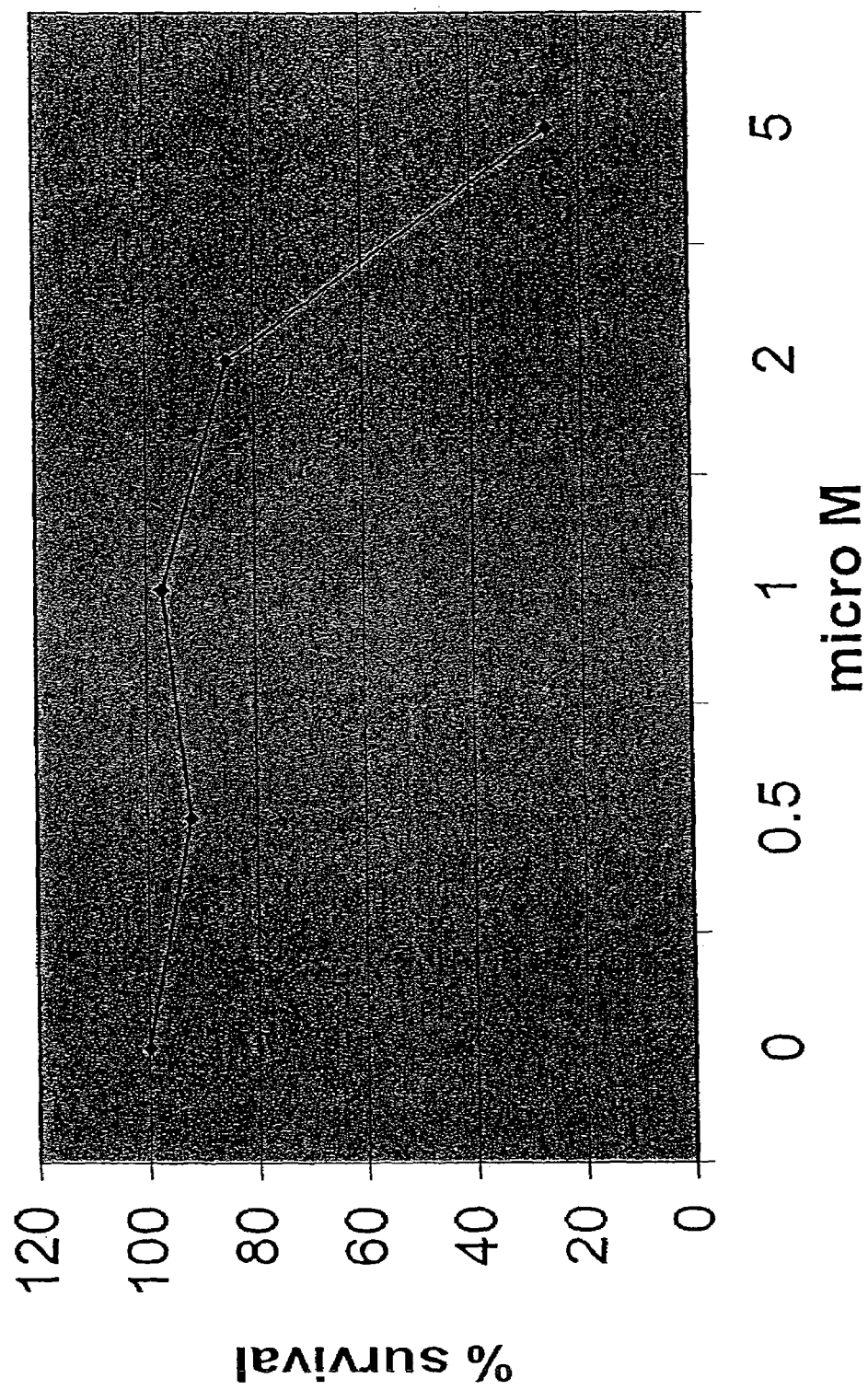
FIG. 11. Mononuclear cells from AML patient were incubated for 5 days with indicated concentrations of MER1 or arsenic trioxide. Cell survival was assessed by trypan-blue exclusion method.
Figure 12:
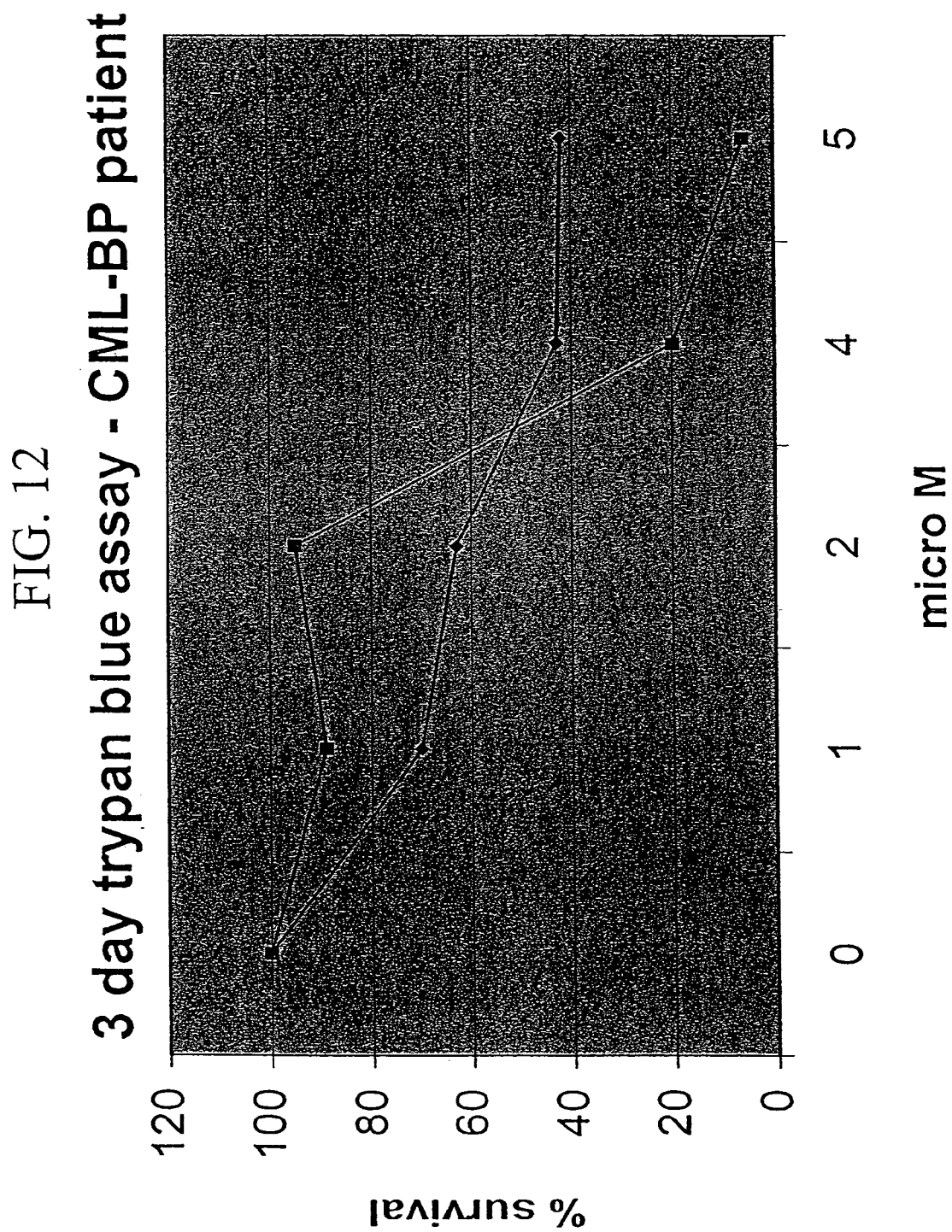
FIG. 12. Mononuclear cells from chronic myeloid leukemia—blastic phase (CML-BP) patient were incubated for 3 days with indicated concentrations of MER1 or arsenic trioxide. Cell survival was assessed by trypan-blue exclusion method.
Figure 13:
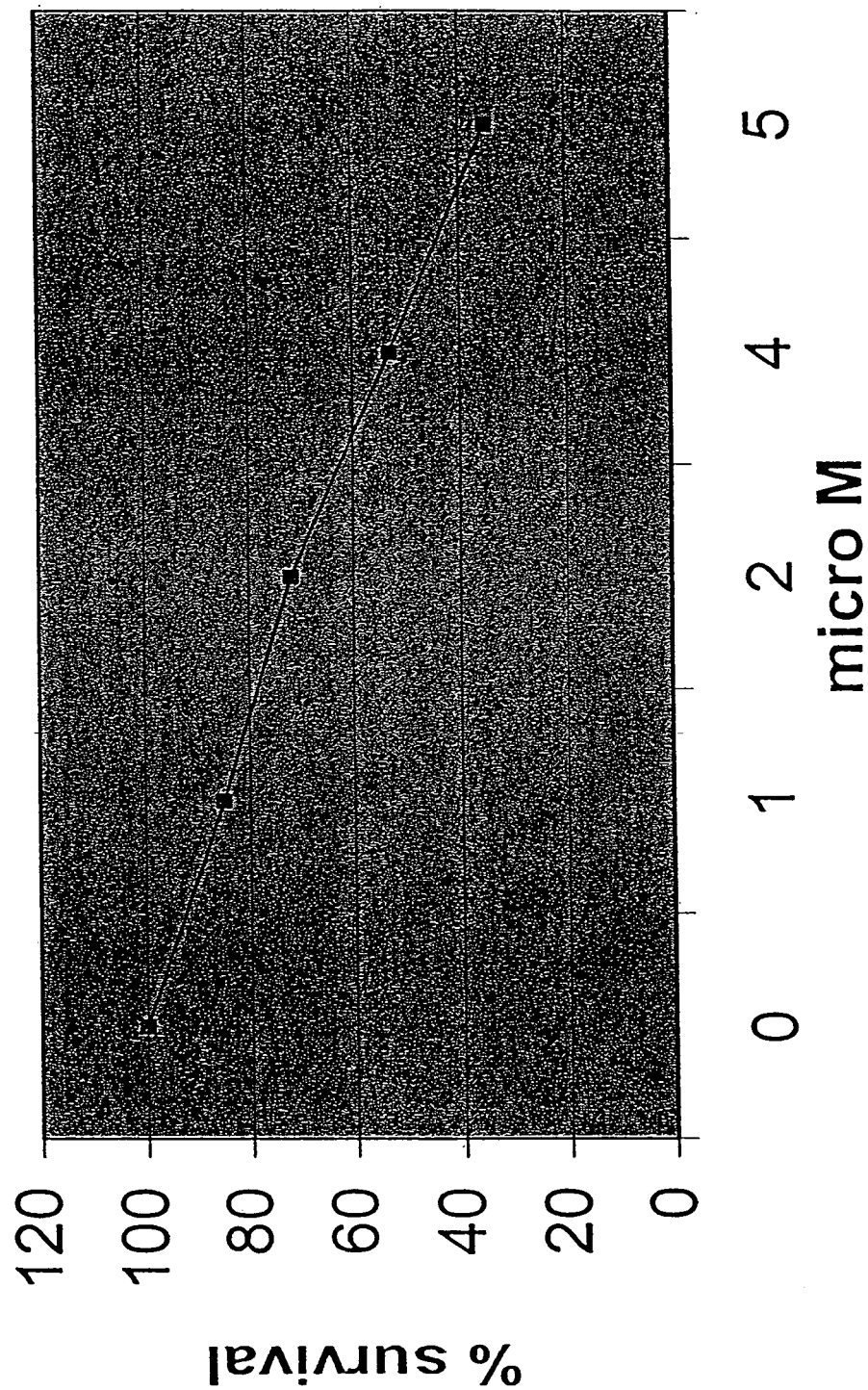
FIG. 13. Mononuclear cells from acute lymphoblastic leukemia (ALL) patient were incubated for 4 days with indicated concentrations of MER1 or arsenic trioxide. Cell survival was assessed by trypan-blue exclusion method.
Figure 14:
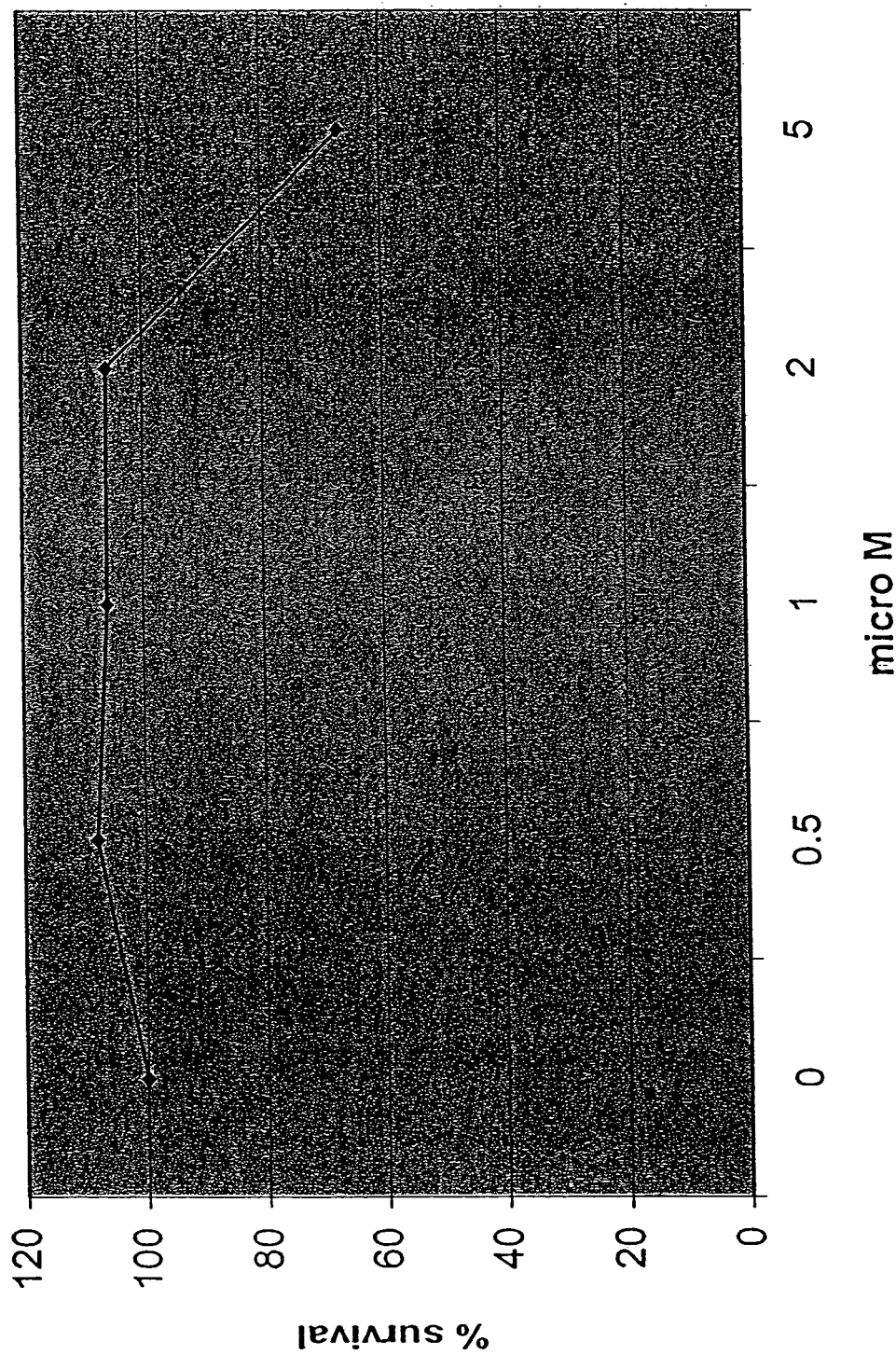
FIG. 14. Mononuclear cells from normal donor were incubated for 5 days with indicated concentrations of MER1 or arsenic trioxide. Cell survival was assessed by trypan-blue exclusion method.
Figure 15:
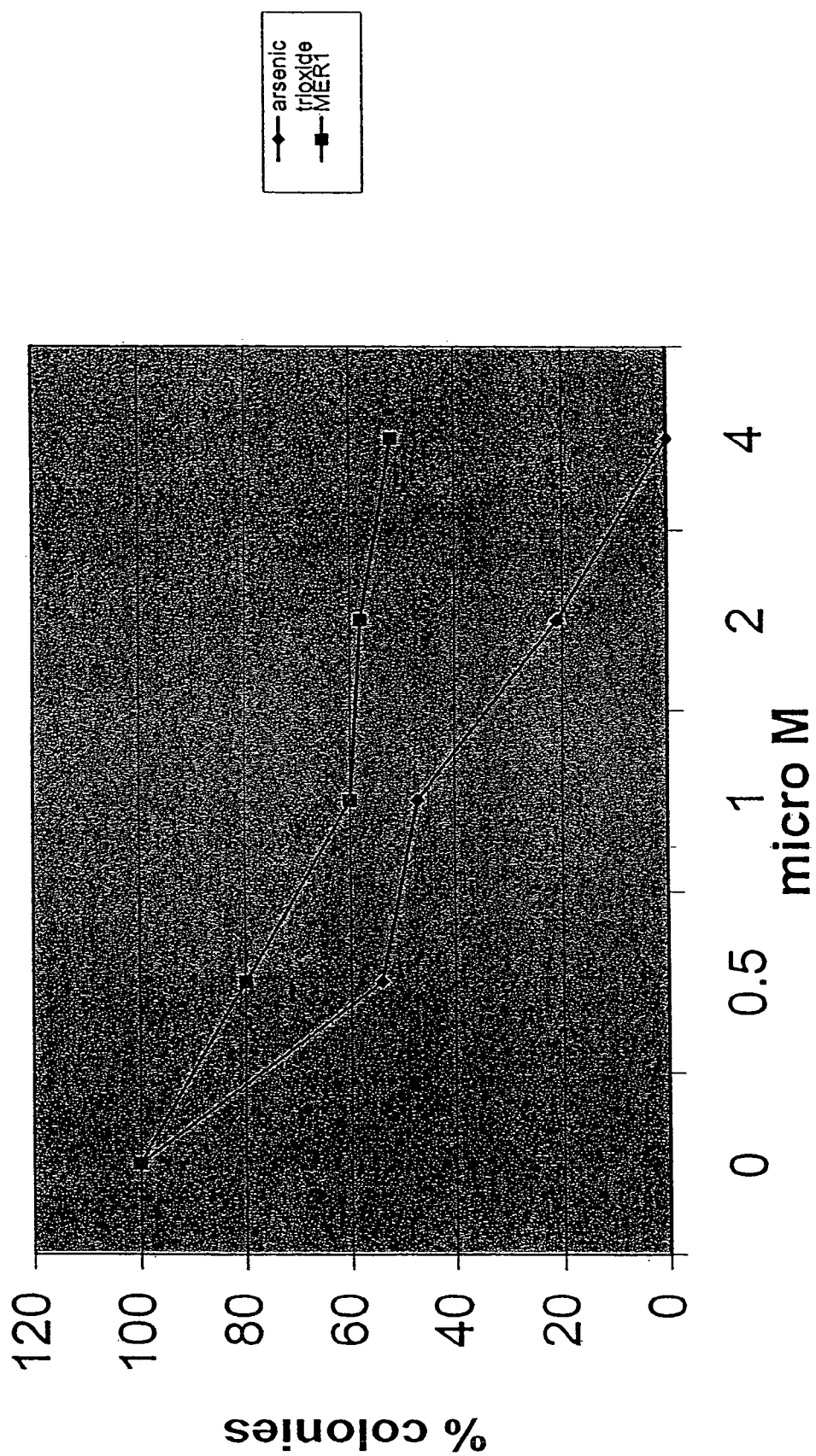
FIG. 15. An 8 day clonogenic assay was performed using normal donor cells and MER1 or arsenic trioxide. Cell aggregates composed of more than 50 cells were counted as one colony and growth inhibition was evaluated as a percentage of colony growth as compared to colony growth in control (no drug) samples.

Toxicity Determination of MER1 and SGLU1 Against Malignant and Normal Blood Cells The present inventors also tested MER1 against blood mononuclear cells (>80% blasts) from 5 leukemia patients (3 with AML, one with CML-BP, and one with ALL; FIGS. 9–13). In short term cell cultures MER1 was as effective as arsenic trioxide (an example is shown in FIGS. 9, 10, and 12). In addition, toxicity of MER1 against normal peripheral blood mononuclear cells was evaluated in samples from 4 healthy donors. In short-term cell suspension cultures by MTT assay MER1 was less toxic to normal cells than malignant cells from leukemia patients (FIG. 14). Most importantly, in long-term clonogenic assay MER1 was less toxic to normal cells than arsenic trioxide (FIG. 15).

Figure 16:
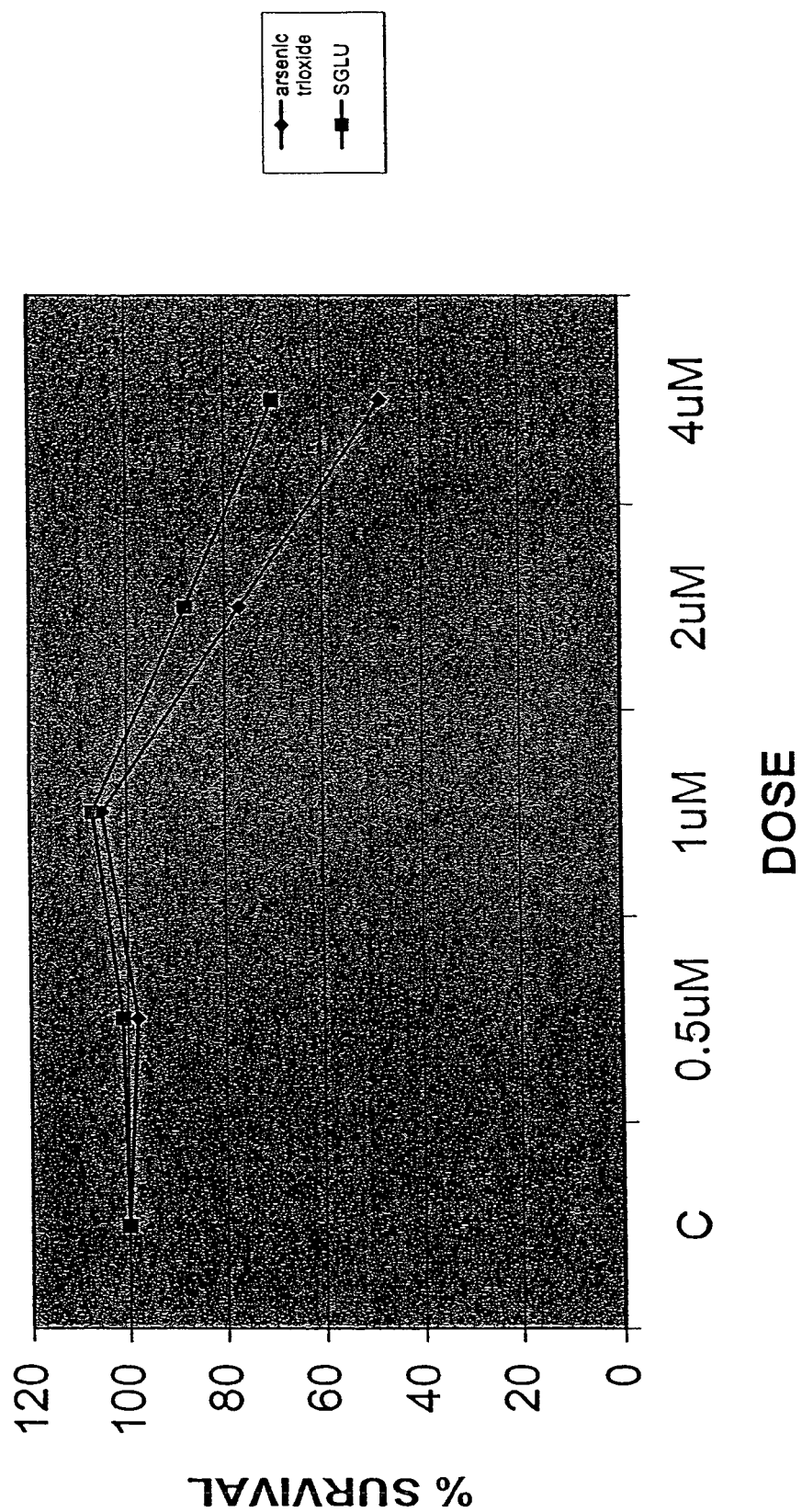
FIG. 16. Mononuclear cells from chronic lymphocytic leukemia (CLL) patient were incubated for 5 days with indicated concentrations of SGLU1 or arsenic trioxide. Cell survival was assessed by trypan blue assay.
Figure 17:
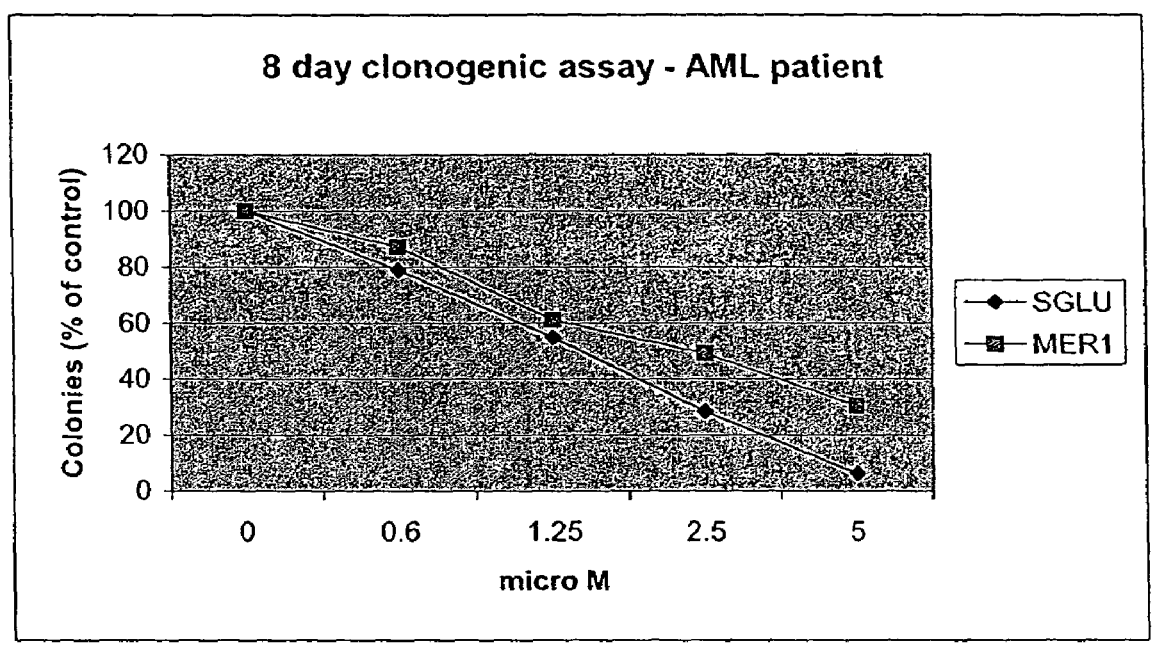
FIG. 17. An 8 day clonogenic assay was performed using mononuclear cells from AML patient with SGLU1 or arsenic trioxide. Cell aggregates composed of more than 50 cells were counted as one colony and growth inhibition was evaluated as a percentage of colony growth as compared to colony growth in control (no drug) samples.
Figure 18:
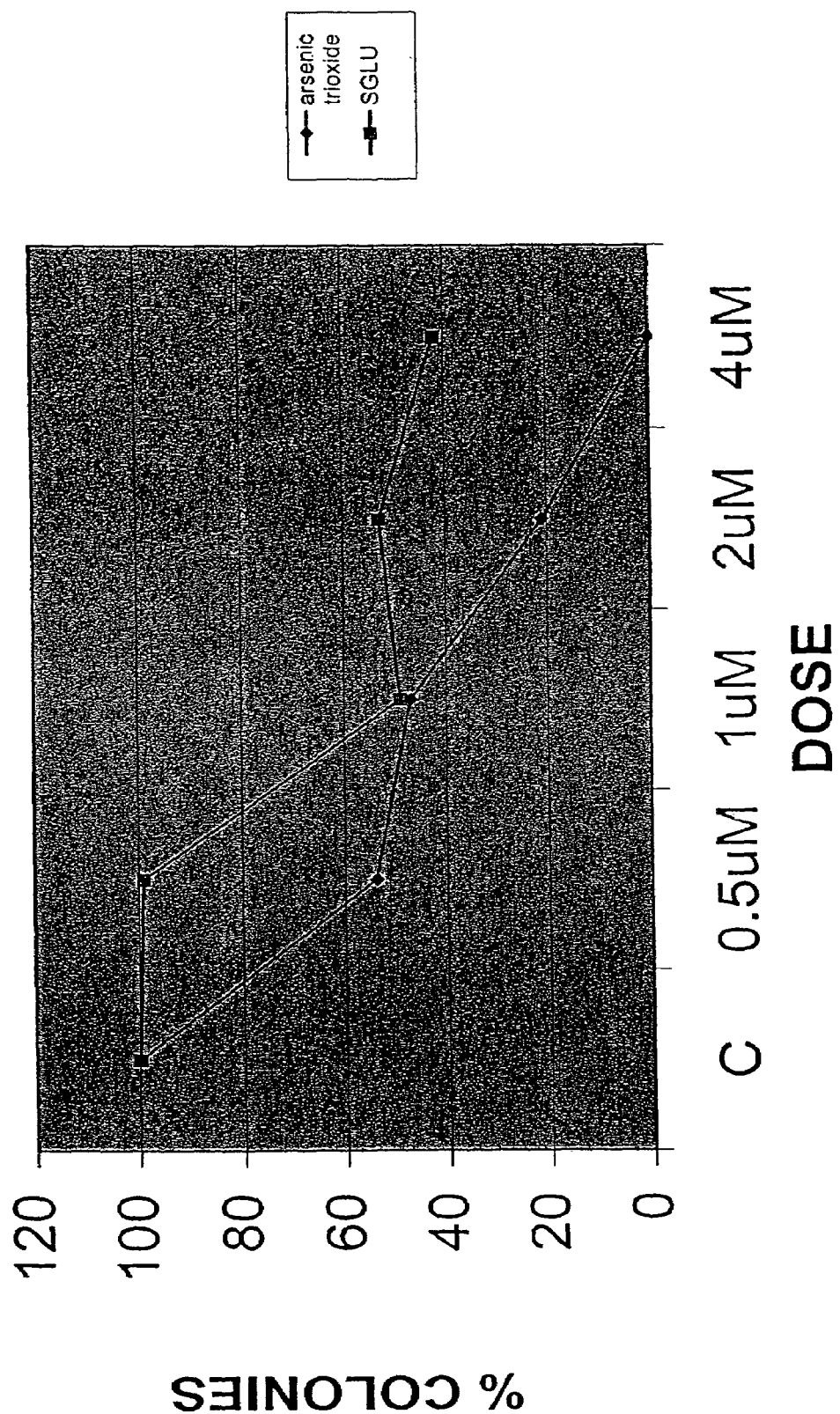
FIG. 18. An 8 day clonogenic assay was performed using normal donor cells, and SGLU1 or arsenic trioxide. Cell aggregates composed of more than 50 cells were counted as one colony and growth inhibition was evaluated as a percentage of colony growth as compared to colony growth in control (no drug) samples.

SGLU1 was tested against blood mononuclear cells from 3 leukemia patients, including a patient with CLL (FIG. 16 which shows a comparison to arsenic trioxide), and 2 patients with AML (FIG. 17). In long-term clonogenic assay SGLU1 was less toxic then arsenic trioxide to normal cells (FIG. 18). In addition to the 8 day clonogenic assay shown in FIG. 18, 9 day and 13 day clonogenic assays have also been performed.

Example 5

Formulation and Stability of MER1

Figure 19:
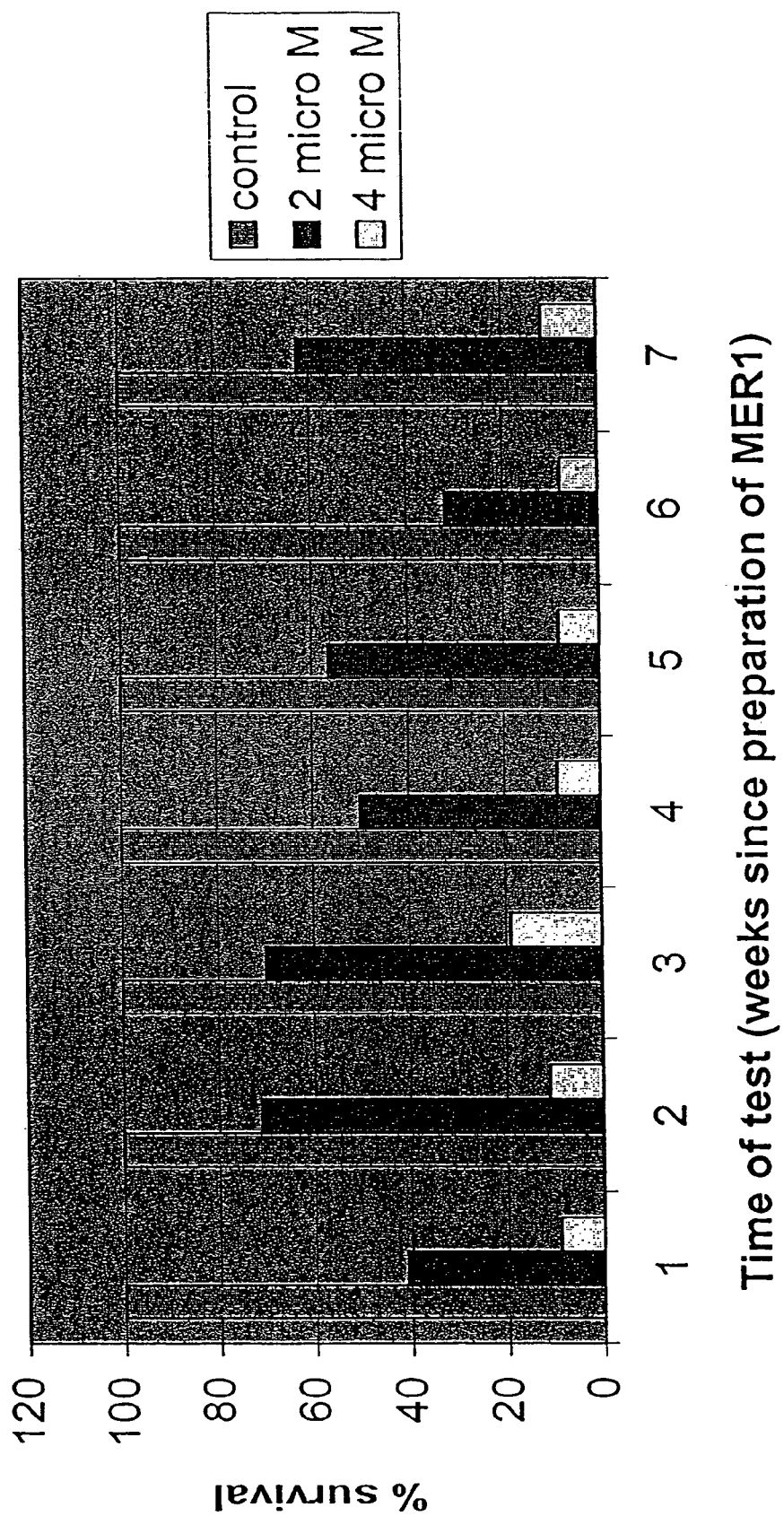
FIG. 19. Stability of MER-1 formulation. Trypan blue assays were performed using HL60 cells and MER-1 1–7 weeks since the preparation of MER-1. HL60 human leukemia cells were incubated for 3 days with indicated concentrations of MER1. Cell survival was assessed by trypan-blue exclusion method. Time of test (i.e., weeks from the time MER1 was prepared) is indicated.

Data has been obtained that shows that MER1 is stable for at least 2 months when dissolved in phosphate buffered saline, as the solutions have maintained cytotoxic activity at the same level in in vitro experiments done during this time period (FIG. 19). In addition detailed pharmaceutical evaluation of MER1 and SGLU1 were performed.

I. Pharmaceutical Evaluation of MER-1

MER-1 was found to have a sufficient solubility and stability to be acceptable for administration in a clinical setting (see data below). It is also sufficiently stable that solutions can be extemporaneously compounded for use in animal testing and possibly an early Phase I study. However, the solution stability is not adequate for manufacturing of larger batches of a liquid dosage form for use in larger clinical trials and distribution in the commercial marketplace where long-term storage is required. A lyophilized dosage form that is reconstituted at the time of use is contemplated for these applications. Preparation of such lyophilized compositions are well known in the art.

A. Solubility

MER-1 has an aqueous solubility of about 15 mg/mL. Higher MER-1 concentrations up of about 150 mg/mL can be achieved by the use of 0.1 N sodium hydroxide to adjust to pH 6. In ethanol, MER-1 has a solubility of more than 100 mg/mL.

B. Solution pH

The natural pH values of aqueous solutions of MER-1 are as follows:

| | |
|---|---|
| 0.1 mg/mL | pH 3.7 |
| 1 mg/mL | pH 3.1 |
| 10 mg/mL | pH 2.3 |

C. Solution Stability

The effects of various pH values were evaluated at a concentration of 10 mg/mL in 0.9% sodium chloride injection. Samples having a pH of 2.3 (natural pH) and also adjusted with sodium hydroxide to pH 5, 7.1, and 8.5 have been evaluated over a period of 3 months under refrigeration. The samples at pH 5 demonstrated better stability retaining about 89% of the initial concentration after 3 months. The solutions at pH 7.1 and 8.5 retained about 92% and 96%, respectively, after 14 days but fell below 90% after that time. The pH 2.3 samples were stable for 7 days but developed a precipitate after that time. See Table 2.

MER-1 is less stable in aqueous solutions at lower concentrations, but is increasingly stable at higher concentrations. At 0.1 mg/mL in water, about 40% of the drug was lost in as little as one hour. As concentrations increased from 1 to 10 mg/mL in 0.9% sodium chloride injection, the drug was stable for increasingly longer periods. The 10-mg/mL concentration was stable for up to 3 months under refrigeration, but unacceptable decomposition occurred after that time. See Table 3.

TABLE 2 pH Stability Profile of MER-1 10 mg/mL in 0.9% Sodium Chloride Injection

| Assay Interval | Remaining MER-1 (%) | | | |
|---|---|---|---|---|
| (Days) | pH 2.3 | pH 5.0 | pH 7.1 | pH 8.5 |
| 0 | 100 | 100 | 100 | 100 |
| 7 | 102 | 105 | 96 | 97 |
| 14 | ppt | 101 | 92 | 96 |
| 30 | | 100 | 80 | 82 |
| 60 | | 91 | | |
| 90 | | 91 | | |
| 180 | | 87 | | |

TABLE 3

MER-1 Solution Stability at Varying Concentrations in 0.9% Sodium Chloride Injection

| Assay Interval | Remaining MER-1 (%) | | | |
|---|---|---|---|---|
| (days) | 0.1 mg/mL[a] | 1 mg/mL | 2 mg/mL | 10 mg/mL |
| 0 | 60[b] | 100 | 100 | 100 |
| 7 | | 94 | 99 | 105 |
| 14 | | 89 | 102 | 101 |
| 21 | | 81 | 96 | 102 |
| 30 | | 79 | 98 | 100 |
| 60 | | | 88 | 91 |
| 90 | | | 84 | 91 |
| 180 | | | | 87 |

[a] In water.
[b] About 40% loss occurred in 60 minutes.
[c] Not determined at this interval.

II. Pharmaceutical Evaluation of SGLU-1

SGLU-1 is found to have sufficient solubility and stability to be acceptable for administration in a clinical setting. It is also sufficiently stable that solutions can be extemporaneously compounded for use in animal testing and possibly an early Phase I study. However, the solution stability is not adequate for manufacturing of larger batches of a liquid dosage form for use in larger clinical trials and distribution in the commercial marketplace where long-term storage is required. A lyophilized dosage form that is reconstituted at the time of use is contemplated for these applications.

A. Solubility

SGLU-1 has an aqueous solubility of about 60 mg/mL. Higher SGLU-1 concentrations can be achieved by the use of 0.1 N sodium hydroxide to raise the solution pH. However, the drug appears to be unstable in an alkaline environment. SGLU-1 is insoluble in ethanol.

B. Solution pH

The natural pH values of aqueous solutions of SGLU-1 are:

0.1 mg/mL, pH 3.9

1 mg/mL pH 3.2

2.5 mg/mL pH 3.0

60 mg/mL pH 2.7

C. Solution Stability

The effects of various pH values were evaluated at a concentration of 2.5 mg/mL in 0.9% sodium chloride injection. Samples having a pH of 3 (natural pH) and also adjusted with sodium hydroxide to pH 5 and 7 were evaluated over 30 days under refrigeration. The samples at pH 5 demonstrated slightly better stability retaining about 90% concentration after 30 days. The solutions at pH 3 and 7 retained about 84% and 82%, respectively. See Table 4.

SGLU-1 at concentrations of 20 mg/mL and 50 mg/mL in 0.9% sodium chloride injection adjusted to pH 5 have undergone stability testing. Less than 10% loss occurred through 60 days of storage under refrigeration. The stability results are shown in Table 5.

SGLU-1 is less stable at lower concentrations. At 0.1 mg/mL in water, more than 10% decomposition occurred in 24 hours at room temperature.

TABLE 4 pH Stability Profile of SGLU-1 2.5 mg/mL in 0.9% Sodium Chloride Injection

| Assay Interval | Remaining SGLU-1 (%) | | |
|---|---|---|---|
| (Days) | pH 3.0 | pH 5.0 | pH 7.0 |
| 0 | 100 | 100 | 100 |
| 3 | 104 | 101 | 97 |
| 5 | 100 | 99 | 93 |
| 7 | 100 | 97 | 91 |
| 14 | 97 | 97 | 91 |
| 21 | 87 | 93 | 84 |
| 30 | 84 | 91 | 82 |

TABLE 5

Stability if SGLU-1 20 mg/mL and 50 mg/mL in 0.9% Sodium Chloride Injection at 4° C.

| Assay Interval | Remaining SGLU-1 (%) | |
|---|---|---|
| (Days) | 20 mg/mL | 50 mg/mL |
| 7 | 101 | 97 |
| 14 | 98 | 98 |
| 30 | 94 | 94 |
| 60 | 92 | 93 |
| 90 | 85 | 87 |

Example 6

Mechanisms for MER1, SAL1, and SGLU1

Figure 20:
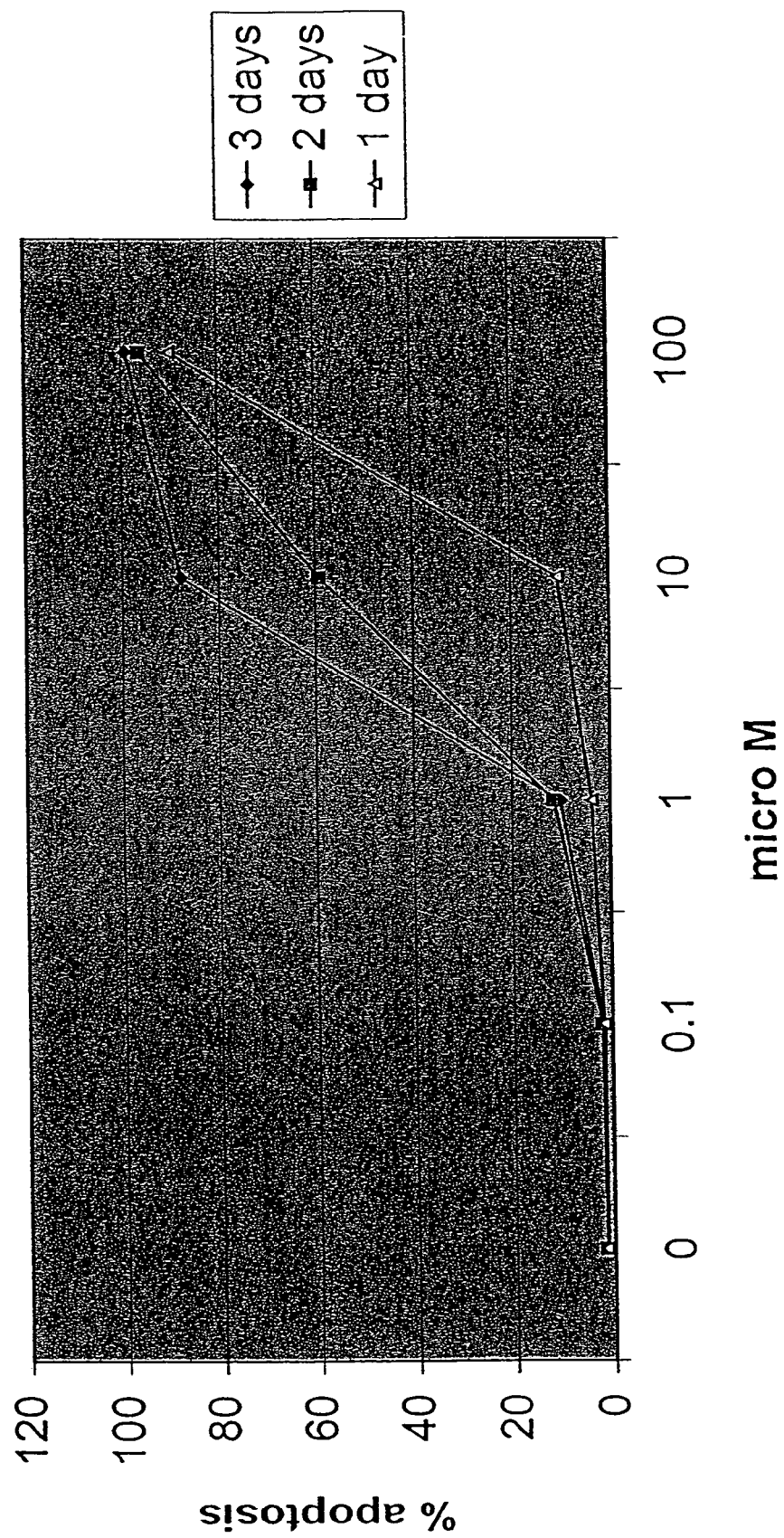
FIG. 20. Apoptosis was assessed by annexin V assay in Hl-60 cells treated with MER1 for 1, 2, or 3 days.
Figure 21:
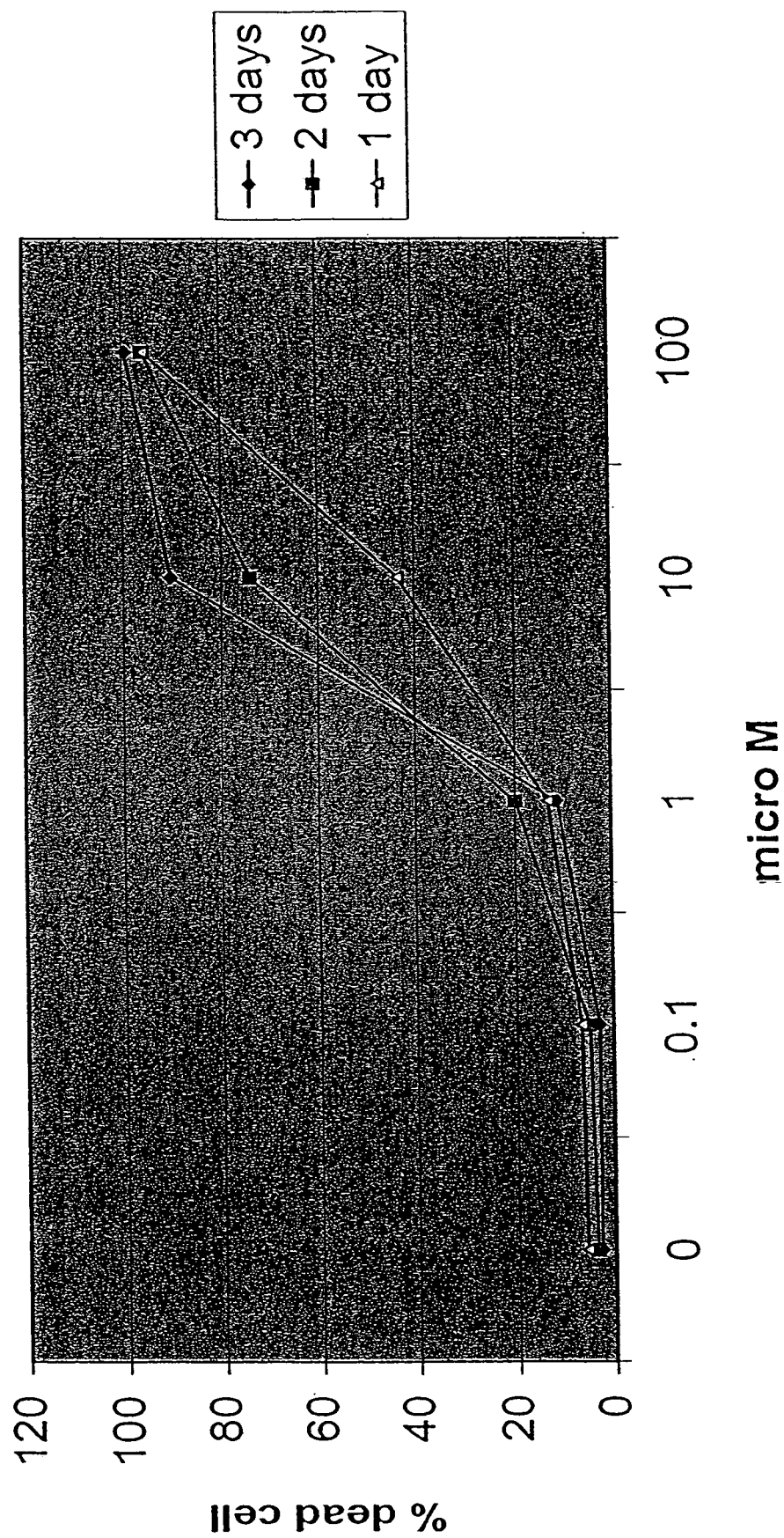
FIG. 21. Dead cell number was assessed by the propidium iodine assay on Hl-60 cells treated with MER1 for 1, 2, or 3 days.
Figure 22:
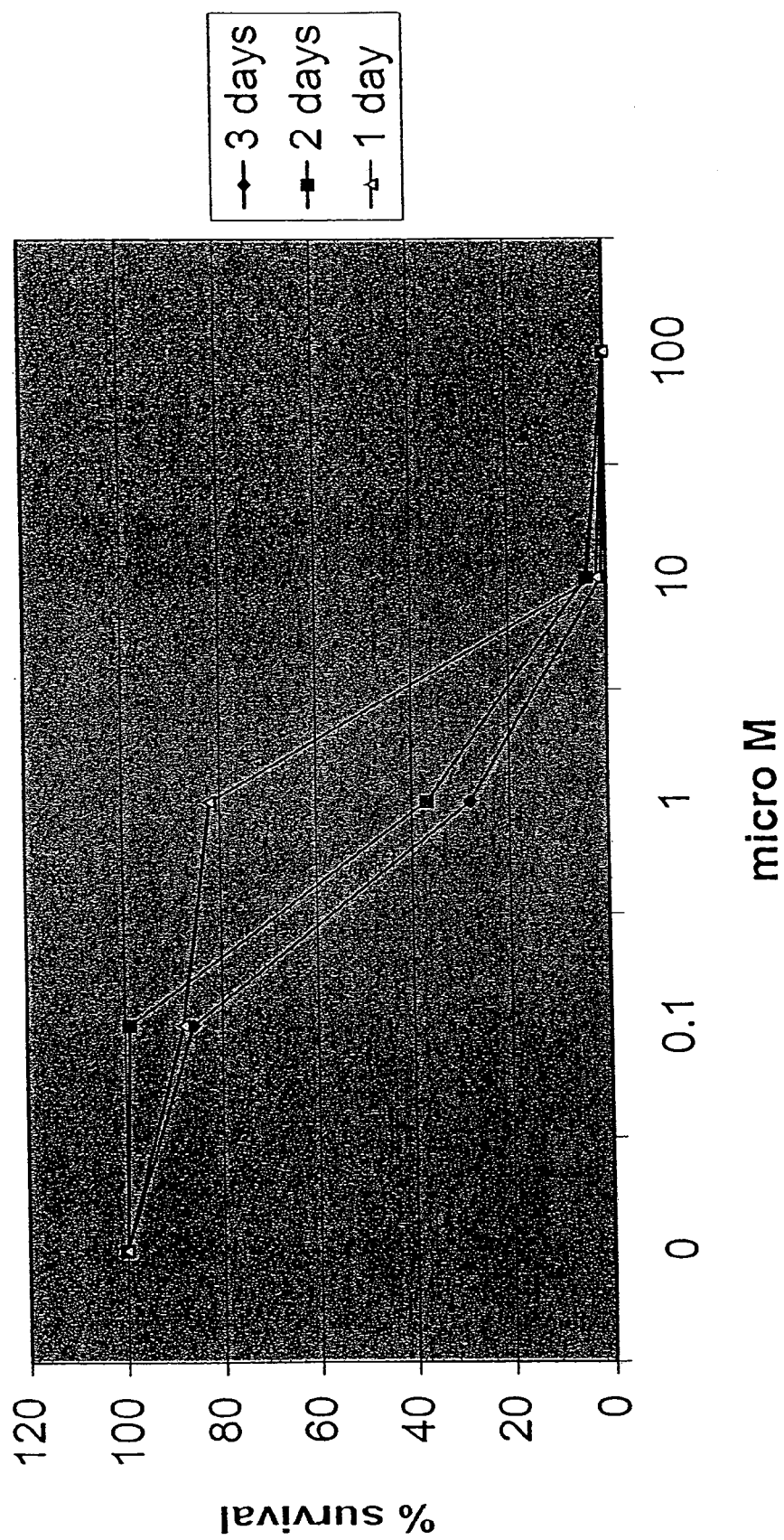
FIG. 22. Cell survival was assessed by trypan-blue exclusion method in HL60 cells treated with MER1 for 1, 2, or 3 days.
Figure 23A:
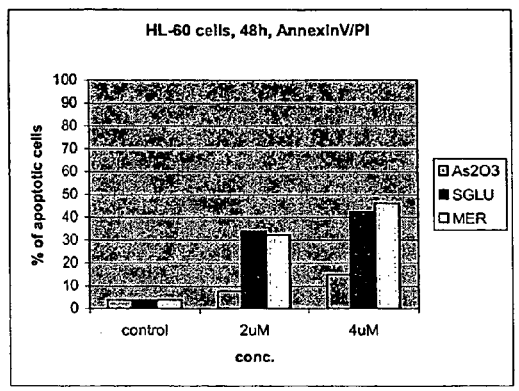
FIGS. 23A, 23B, 23C, 23D, 23E, & 23F. Apoptosis was assessed in HL-60 cells treated with MER1, SGLU1 or arsenic trioxide, as indicated, by the annexin V assay and propidium iodide staining at 48 hours (FIG. 23A) and at 72 hours (FIG. 23D); by the caspase assay (phi-phi-lux staining) at 48 hours (FIG. 23B) and 72 hours (FIG. 23E); and by the CMXRos/MT-Green Assays at 48 hours (FIG. 23C) and 72 hours (FIG. 23F).
Figure 23B:
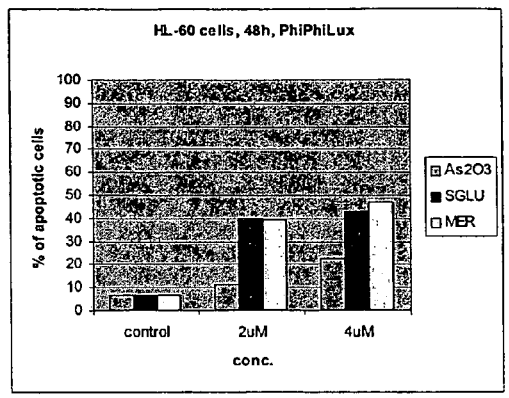
Figure 23C:
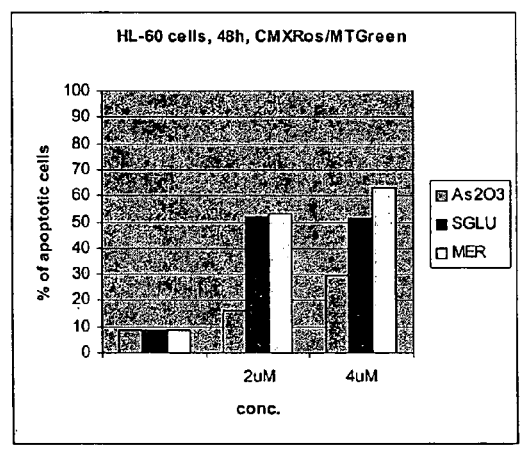
Figure 23D:
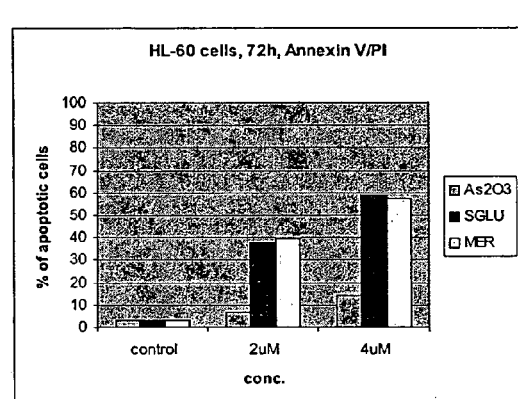
Figure 23E:
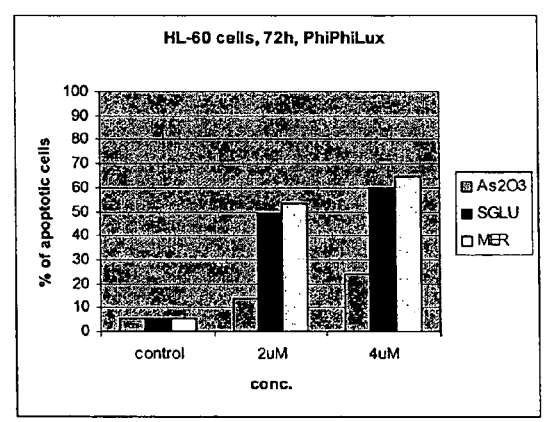
Figure 23F:
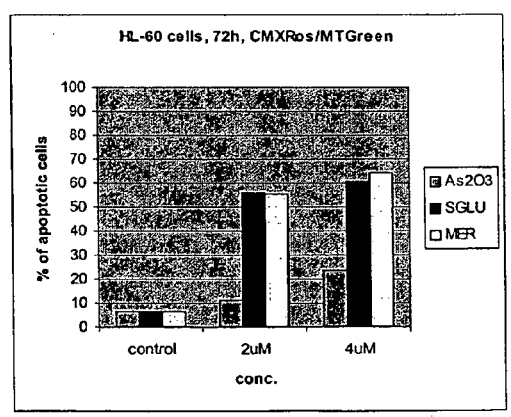

The induction of apoptosis, effects on the cell cycle, induction of maturation, and degradation of aberrant PML/RARalpha fusion protein, have all shown to be mechanisms of action of arsenic trioxide. The present inventors have examined the potential of MER1 to induce apoptosis in HL60 human leukemia cells (assay time 1–3 days). The induction of apoptosis followed closely diminished percentage of surviving cells (FIGS. 20, 21 & 22). Additional studies using both MER1 and SGLU have established that the induction of apoptosis (annexin V staining) by these compounds involves change of the potential of mitochondrial membrane (CMXRos staining) and activation of caspases (PhiPhiLux staining) see FIGS. 23A, 23B, 23C, 23D, 23E, & 23F.

Figure 24:
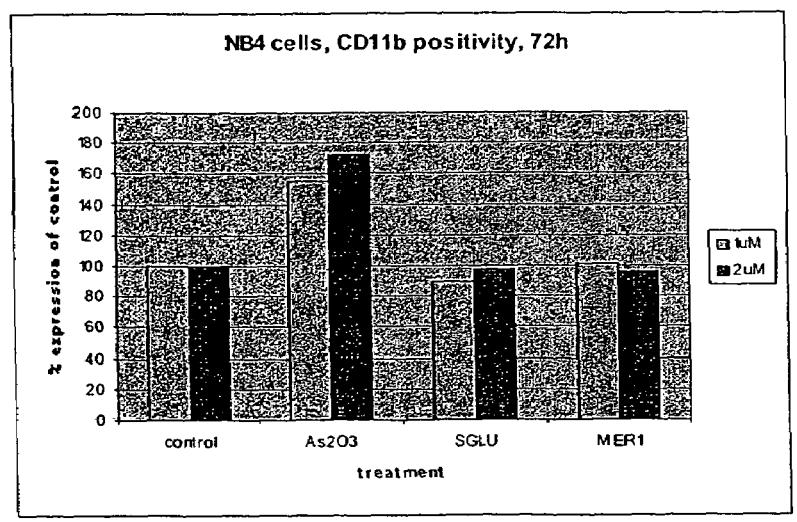
FIG. 24. NB4 cells assayed for the effects of arsenic trioxide, SGLU1 and MER1 on maturation by assaying the expression of CD11b marker on the surface of leukemic cells by flow cytometer (after 3 day incubation). Data shows that, in contrast to arsenic trioxide, SGLU1 and MER1 do not induce maturation.
Figure 25A:
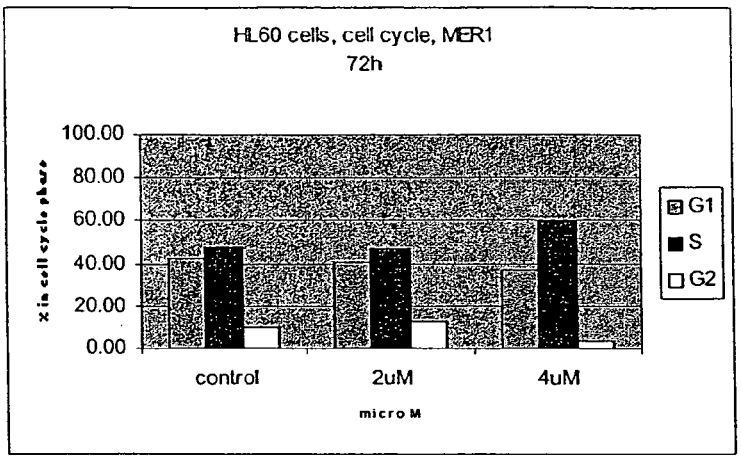
FIGS. 25A, 25B & 25C. HL60 cells assayed for the effects of MER1 (FIG. 25A), SGLU1 (FIG. 25B) & arsenic trioxide (FIG. 25C) on the cell cycle after 3 day incubation with indicated concentrations.
Figure 25B:
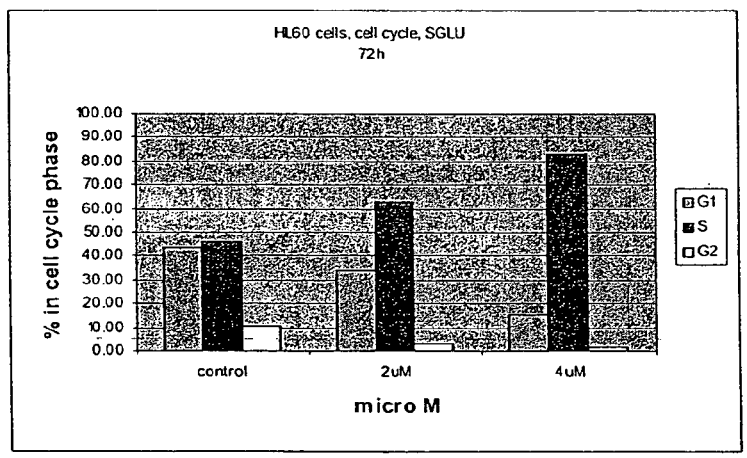
Figure 25C:
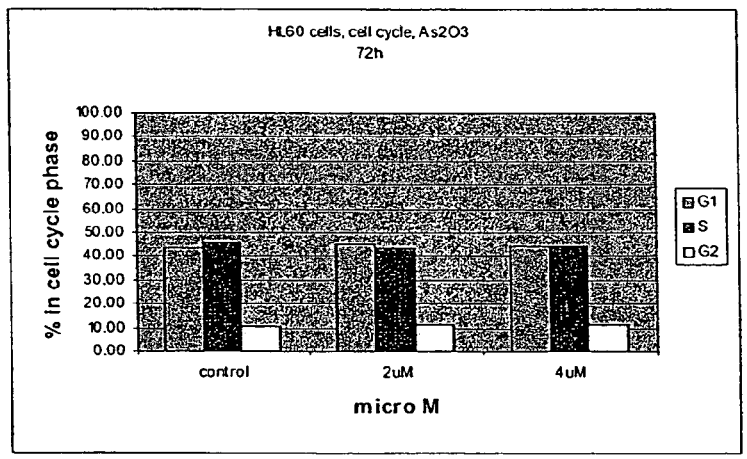

It has been reported that arsenic trioxide induced maturation of cells expressing PML/RARalpha gene. To test whether SGLU and MER1 have similar capability NB4 cells (expressing the PML/RARalpha gene) were used and, after 3 days of exposure to arsenicals, the expression of CD11b on the surface of the cells was measured by flow cytometer. CD11b is a maturation marker for myeloid cells. Data is presented in FIG. 24 indicating that SGLU and MER1 do not induce maturation. Possible cell cycle disturbance in HL-60 cells treated with the different arsenicals of the invention was assessed using flow cytometry and staining with propidium iodide. It was found that SGLU caused marked accumulation of cells in S-phase of cell cycle, with MER1 causing a similar effect to lesser degree (FIGS. 25A, 25B). FIG. 25C describes S-phase accumulation of cells in response to arsenic trioxide.

Figure 26A:
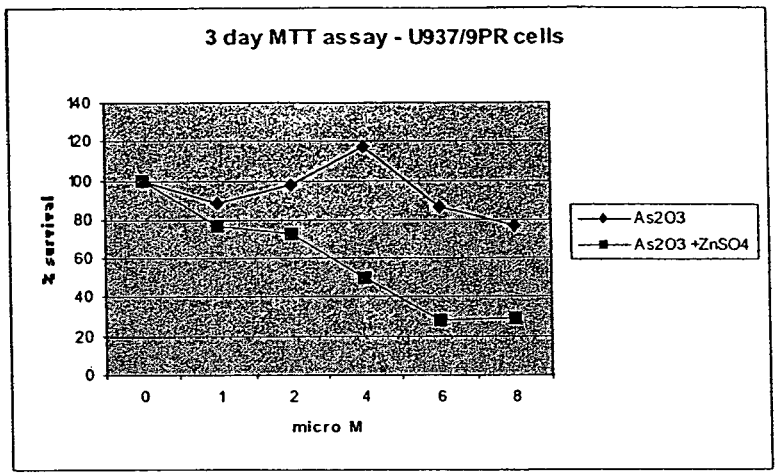
FIGS. 26A, 26B & 26C. Three day MTT assay in U937/9PR cells treated with arsenic trioxide (FIG. 26A), SGLU1 (FIG. 26B) and MER1 (FIG. 26C) with and without zinc to analyze the role of the PML/RARalpha gene. Zinc activates the the PML/RARalpha gene. The data shows that the presence of functional PML/RARalpha gene is pre-requisite for cells to be sensitive to arsenic trioxide but has no influence on the sensitivity of the cells to SGLU1 and MER1.
Figure 26B:
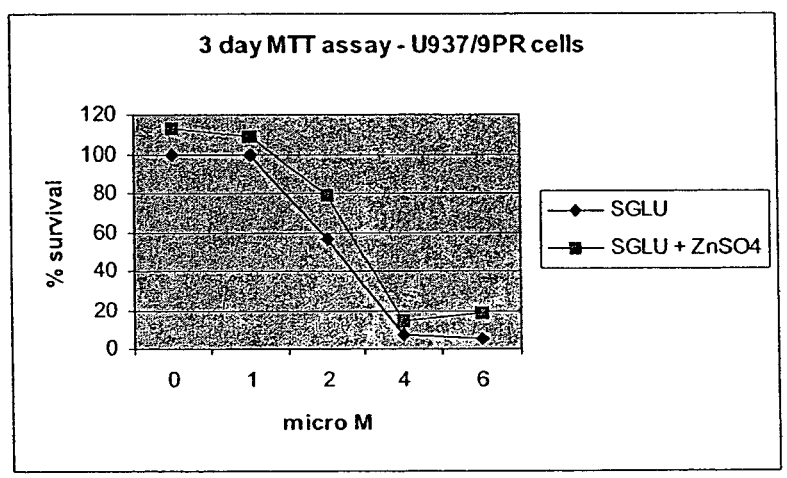
Figure 26C:
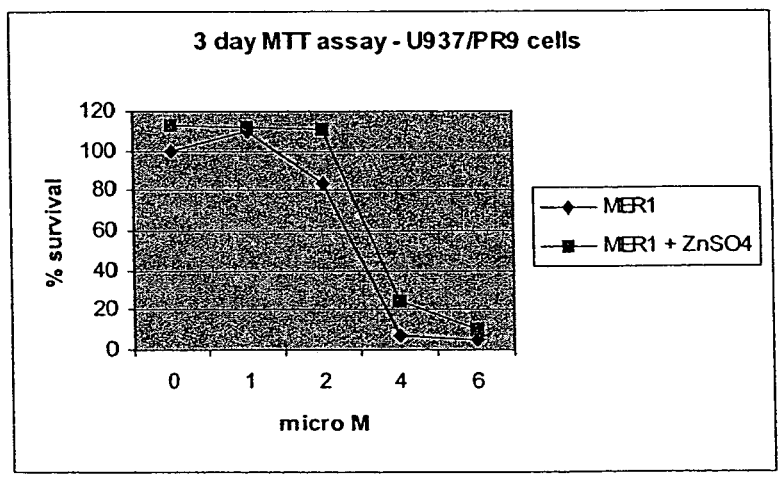

To establish whether the presence of PML/RARalpha fusion protein in the leukemic cells contributes to the observed sensitivity of leukemic cells to SGLU and MER1 the following system was used: U937 cells, known to be resistant to arsenic trioxide, were transfected with PML/RARalpha gene. This gene becomes functional in the presence of zinc. Thus, transfected U937 cells (U937/PR9) were treated with different arsenical with or without zinc. Results are shown in FIGS. 26A, 26B & 26C which indicate that the presence of functional PML/RARalpha gene is pre-requisite for cells to become sensitive to arsenic trioxide but have no influence on the sensitivity of the cells to SGLU and MER1.

Example 7

In Vivo Evaluation of the Therapeutic Potential of MER1, SAL1, and SGLU1

The animal model of human leukemia is represented by severe combined immunodeficient (SCID) mouse bearing human leukemia cells. This model is unique in that it allows growth of human leukemia in animals in a mode similar to that seen in patients. It offers an opportunity to rapidly test the in vivo efficacy of new drugs at different dose levels and schedules. Furthermore, not only can animal survival be monitored, but also the effect of treatment on the dissemination pattern of the disease. Treatment of SCID mice typically starts 2 days after inoculation with human leukemic cells. Initial in vivo experiments in SCID mice injected with one human leukemia cell line will determine dose and schedule of MER1, SAL1 or SGLU1 for the other mice model as well as for initial human trials.

Animals are monitored daily and sacrificed when moribund or at the completion of the study (usually double the survival time of the control group). Necropsy is performed on animals that survive for long time and tissues are analyzed for the presence of human DNA by polymerase chain reaction (PCR) using primers specific for DNA sequences of HLA-DQα. Since leukemia is a systemic disease, the presence of minimal residual disease is studied by checking for HLA-DQα in DNA from different mouse tissues. This data may help predict whether the drug is active in selective compartments for leukemia, e.g. bone marrow, solid organs, or central nervous system.

Prerequisites for in vivo therapeutic experimentation in SCID mice are 1) the verification of leukemia cells engraftment in animals and 2) the determination of acute toxicity of tested compounds (definition of maximally tolerated dose).

I. Verification Of Leukemia Cells Engraftment In Animals. The first in vivo experiment involved 4 groups of SCID mice. Five mice per group were inoculated intraperitoneally with human leukemia cells of different types: HL60 (AML), KBM5 (CML-BP), KBM7-acute myeloid leukemia, and Z119 (ALL). HL60 and KBM5 cells showed excellent engraftment: in HL60 group all mice died within days 31 and 36 after inoculation, while in the KBM5 group mice died within 34th and 36th day. The engraftment was verified by performing PCR for DNA sequences of human HLA-DQα (test was positive in all tissues from all the mice). At day 100, there were still 4 of 5 mice alive in KBM7 and 5 of 5 mice alive in Z119 group. At that day all mice were sacrificed and tissues analyzed by PCR for HLA-DQα.Testing was negative indicating lack of leukemia cell engraftment. Alternative cell lines of same type will be required for planned therapeutic studies.

II. Determination of Acute Toxicity of Tested Compounds. For toxicology testing, immunocompetent Swiss Webster mice were used. The present inventors have confirmed that $LD_{50}$ concentration for arsenic trioxide is 10 mg/kg.

A. Brief Toxicity Testing Of SLGU1 in Swiss-Webster Mice. Two studies were performed on Swiss-Webster mice to test the toxicity of SGLU1. In the first study, SGLU1 was administered at doses of 178 mg/kg; 285 mg/kg; and 357 mg/kg via the IP route. The toxicity was measured by the mortality of mice. It was found that the mice tolerated the 178 mg/kg and the 285 mg/kg doses of SGLU1 well. The data of this study are summarized in Table 6.

TABLE 6

Brief Toxicity Testing Of SLGU1

| | Dose (mg/kg) | | |
|---|---|---|---|
| Administered IP | 178 | 285 | 357 |
| Dead/Total Number | 0/5 | 1/5 | 5/5 |

In the second study the toxicity with each mouse weighted were studies for administration of SGLU1 by both the IP and IV routes at doses of 318 mg/kg and 375 mg/kg. Thus, inventors have established that $LD_{50}$ concentration for SGLU1 is 350 mg/kg. The results are summarized in Table 7.

TABLE 7

Better Performance With Each Mouse Weighted

| | Dose (mg/kg) | |
|---|---|---|
| | 318 | 375 |
| Dead/Total Number for IP Administration | 0/5 | 4/5 |
| Dead/Total Number for IV Administration | 1/5 | 5/5 |

B. Brief Toxicity Testing Of MER-1 in Swiss-Webster Mice. Two studies were performed on Swiss-Webster mice to test the toxicity of MER-1. In the first study, MER-1 was administered at doses of 71 mg/kg; 107 mg/kg; and 143 mg/kg via the IP route. The toxicity was measured by the mortality of mice. It was found that the mice tolerated the 71 mg/kg and the 107 mg/kg doses of MER-1 well with no mortality. The data of this study are summarized in Table 8.

TABLE 8

Brief Toxicity Testing Of MER-1

| | Dose (mg/kg) | | |
|---|---|---|---|
| Administered IP | 71 | 107 | 143 |
| Dead/Total Number | 0/5 | 0/5 | 5/5 |

In the second study the toxicity with each mouse weighted were studies for administration of MER-1 by both the IP and IV routes at doses of 125 mg/kg; 156 mg/kg; and 170 mg/kg. Thus, inventors have established that $LD_{50}$ concentration for MER1 is 150 mg/kg. The results are summarized in Table 9.

TABLE 9

Better Performance With Each Mouse Weighted

| | Dose (mg/kg) | | |
|---|---|---|---|
| | 125 | 156 | 170 |
| Dead/Total Number for IP Administration | 0/5 | 2/5 | 5/5 |
| Dead/Total Number for IV Administration | 0/5 | 0/5 | 5/5 |

C. Brief Toxicity Testing Of SAL1 in Swiss-Webster Mice. Similar to experiments above, brief toxicity testing of SAL1 established that $LD_{50}$ concentration for SAL1 is 50 mg/kg.

Example 8

Pharmacokinetics of MER1, SAL1, and SGLU1

The pharmacokinetic disposition of MER1, SAL1, and SGLU1 will be evaluated in mice following intravenous administration via the tail vein. A dose near the previously determined MTD will be studied initially. Blood samples will be collected at different sampling time points (0 (pre), 5, 10, 15, 30, 45, 60 min and 2, 3, 4, 6, 8, 12, 16, 24, 48, 72 hrs) following drug administration (8 mice/time point). For blood collection, mice are euthanized by $CO_2$ inhalation, then decapitated and blood collected by exsanguination. Blood samples will be collected in test tubes containing heparin, centrifuged, and plasma separated and stored at −80° C. until analysis. Studies will be repeated and plasma ultrafiltrate collected via centrifugation of plasma at 2000 g×0.20 minutes in Amicon Centrifree micropartition units. Ultrafiltrate will be stored at −80° C. until analysis. In selected groups, various tissues will be harvested post-mortem and frozen for analysis of tissue disposition. Arsenic content in plasma and ultrafiltrate samples will be measured via graphite furnace (flameless) atomic absorption spectroscopy. Measured drug concentrations will be analyzed compartmentally to obtain pharmacokinetic parameters.

Example 9

Toxicology Studies

A. Single-Dose Toxicology Study for MER1. Data from the single dose Merltoxicology study is summarized in Table 10 below.

TABLE 10

MER1 Single Dose: 3 Day, 14 Day, 42 Day Toxicology

Strain: Swiss Webster  
Age at Start: ~6 wks  
Group Size: 15/sex, with 5/sex in each of the 72 h, 14 d, and 42 d groups.  
Groups: 0, 50, 80, 120, and 150 mg/kg/d  
Objective: To investigate the initial toxicology of MER1 when given intravenously as a single dose to mice.  
Parameters Evaluated: Clinical signs (daily), body weight (pre and twice weekly), clin path, gross pathology, organ weight, and histopathology (72 h, d 14, d 42).  
Processed and read: All tissues (72 h, found dead) in all dose groups. Heart, lung, ovary (d 14, d 42) in all dose groups.

Dosing Frequency: Once  
Dosing Volume: 10 mL/kg  
Vehicle: Saline, pH adjusted w/NaOH to 7.0 (except for the male 120 and 150 groups and the female 150 groups which had pH = 5.0)  
Lot: Merida Sotelo notebook, p43, May 10, 2001, M.P. 151 degrees

| | MER1 -Related Findings | | | |
|---|---|---|---|---|
| mg/kg/day | 40 mg/kg F<br>57 mg/kg M | 80 mg/kg F<br>86 mg/kg M | 120 | 150 |
| Conclusions: • | | | | |
| Death | 0 | 0 | 0 | 1 F d 1 |
| Comment: | | | | |
| Clinical Signs | | | | 5 F moribund & sac d 2 |
| Comments | Tail necrosis after single I.V. dose of MER1 in 86, 120, & 150 mg/kg mice. Animal health and tails are monitored twice daily. As needed, tails are amputated and then cauterized while animal is under Isoflurane anesthesia. | | | |
| Body Weights | — | — | | |
| Fd Consump | N/A | N/A | N/A | N/A |

| Hematology-3 day | Male | Female | Male | Female | Male | Female | Male | Female |
|---|---|---|---|---|---|---|---|---|
| RBC | — | — | — | — | — | — | | |
| HGB | — | — | — | — | — | — | | |
| HCT | — | — | — | — | — | — | | |
| Hematology-14 day | | | | | | | | |
| RBC | | | | | | | | |
| HGB | | | | | | | | |
| HCT | | | | | | | | |
| Hematology-42 day | | | | | | | | |
| RBC | — | — | — | — | — | — | | |
| HGB | — | — | — | — | — | — | | |
| HCT | — | — | — | — | — | — | | |
| Comment: • | | | | | | | | |

| Serum Chem-3 day | Male | Female | Male | Female | Male | Female | Male | Female |
|---|---|---|---|---|---|---|---|---|
| | — | — | — | — | | | | |
| Serum Chem-14 day | | | | | | | | |
| Serum Chem-42 day | | | | | | | | |
| | — | — | — | | | | | |
| Comment: • | | | | | | | | |

| Gross Path - 3 day | Male | Female | Male | Female | Male | Female | Male | Female |
|---|---|---|---|---|---|---|---|---|
| | — | — | — | — | — | | | |
| Gross Path - 14 day | | | | | | | | |
| Gross Path - 42 day | | | | | | | | |
| Organ wts - 3 day (rel. to brain) | — | — | — | | | | | |
| Organ wts - 14 day (rel. to brain) | | | | | | | | |
| Organ wts - 42 day (rel. to brain) | | | | | | | | |
| Comment: • | | | | | | | | |

| Histopathology | Low | | Low-intermediate | | High-intermediate | | High | |
|---|---|---|---|---|---|---|---|---|
| Sex | F | M | F | M | F | M | F | M |
| Dose: mg/kg/day | 40 | 57 | 80 | 86 | 120 | 120 | 150 | 150 |
| Lung/Heart: Arteritis/Vasculitis/thrombosis | | | | | | | | |
| 72 h | 0/5 | 0/5 | 0/5 | 1/5 | 0/5 | 0/2 | 1/5 | 0/5 |
| 14 d | | | | | | 2/5 | 1/5 | 1/5 |
| 40/42 d | | | | | | | | |
| Total | | | | | | | | |
| Ovary: increased apoptosis of follicular cells | | | | | | | | |
| 72 h | | | | | | | | |
| 14 d | | | | | | | | |
| 40/42 d | | | | | | | | |
| Total | | | | | | | | |

TABLE 10-continued

MER1 Single Dose: 3 Day, 14 Day, 42 Day Toxicology

| | |
|---|---|
| Comment: | • Vascular lesions in heart and lungs. To date, effect level in male arm = 86 mg/kg and female arm = 150 mg/kg. |

Unless indicated otherwise, values = treatment group mean ÷ control group mean.
"—" indicates no compound-related finding.

B. Multiple-Dose Toxicology Studies

Further studies were performed to determine the dose-limiting toxicity associated with the administration of repeated doses in groups of mice. Tables 11–16 below describe the results of the multiple-dose toxicology studies for MER-1 and Tables 17–21 describe results of the multiple-dose toxicology of SGLU-1.

TABLE 11

MER-1 Multiple Dose Toxicology In Vivo

Multiple Dose 28 d Toxicology

| | |
|---|---|
| Strain: Swiss Webster | Dosing Frequency: Daily × 5 |
| Age at Start: ~6 wks | Dosing Volume: 10 mL/kg |
| Group Size: 3/grp, male only | Vehicle: Saline, pH w/NaOH to 5.0 |
| Groups: 0, 30, 40, 50, 60, 70, 80, 90 and 100 mg/kg/d | Lot: Merida Sotelo notebook, p 43, May 10, 2001, M. P. 151 degrees |
| Operator: Julie Miller | Dose Dates: Mar. 10, 2002–Mar. 14, 2002 Sacrifice Date: Apr. 12, 2002 |

Objective: To investigate the potential toxicity and maximally-tolerated cumulative dose of MER1 when given intravenously (tail vein) daily × 5 to mice.
Total cumulative dose = 150, 200, 250, 300, 350, 400, 450, and 500 mg/kg.
Parameters Evaluated: Clinical signs (daily), body weight (pre dose and twice weekly) × 4 weeks. Necropsy moribund/dead animals. Necropsy surviving animals (d 28).
To process and read: Heart, lung, liver, kidney (d 28) in control (0 mg/kg) and high dose (100 mg/kg) groups. Depending on whether lesions are found, next lower dose groups may be evaluated.

| | MER1-Related Findings | | | |
|---|---|---|---|---|
| mg/kg/day | 30 | 40 | 50 | 60 |
| Conclusions: | | | | |
| Death | — | — | — | — |
| Comment: | Initial period of hyperactivity after dosing, followed by slightly decreased activity. Normal activity resumed 2–3 hours after dosing. | | | |
| Clinical Signs | | | | |
| Comments | Animal tolerance of multiple doses of pH adjusted MER1 - MER1_02 study. There is no evidence of tail necrosis after 4 days of daily dosing in the 0–80 mg/kg/day groups; no evidence of tail necrosis after 3 days of daily dosing in the 90–100 mg/kg/day groups. All animals recover within several hours from short period of moderately decreased activity. Tail lesions and necrosis first noted one day after daily × 5 dosing is completed (Day 6) in all dose groups from 30–100 mg/kg/d. Animals are monitored daily and tails amputated as needed. | | | |
| Fd Consump | N/A | N/A | N/A | N/A |
| Body Weights | Male Female | Male Female | Male Female | Male Female |
| | 35 g — | 39 g — | 34 g — | 35 g — |
| Histopathology 28 d | | | | |

Unless indicated otherwise, values = treatment group mean ÷ control group mean.
"—" indicates no compound-related finding.

TABLE 12

Analysis of Organ Lesions in Response to MER-1

| Animal No. | Dose Group | Heart | Lung | Liver | Kidneys |
|---|---|---|---|---|---|
| MER1-02-1001 | 0 mg/kg/day | No significant lesion | No significant lesion | No significant lesion | No significant lesion |

TABLE 12-continued

Analysis of Organ Lesions in Response to MER-1

| | | | | | |
|---|---|---|---|---|---|
| MER1-02-1003 | 0 mg/kg/day | No significant lesion | No significant lesion | No significant lesion | No significant lesion |
| MER1-02-1005 | 0 mg/kg/day | No significant lesion | No significant lesion | No significant lesion | No significant lesion |
| MER1-02-2001 | 30 mg/kg/day | No significant lesion | No significant lesion | No significant lesion | No significant lesion |
| MER1-02-2003 | 30 mg/kg/day | No significant lesion | No significant lesion | No significant lesion | No significant lesion |
| MER1-02-2005 | 30 mg/kg/day | No significant lesion | Vasculitis, 1+ Fibrin thrombi, 1+ | No significant lesion | Inflammation, 1+ |
| MER1-02-3001 | 40 mg/kg/day | No significant lesion | Fibrin thrombi, 1+ | No significant lesion | No significant lesion |
| MER1-02-3003 | 40 mg/kg/day | No significant lesion | No significant lesion | Infarct, 1+ | No significant lesion |
| MER1-02-3005 | 40 mg/kg/day | No significant lesion | Vasculitis, 1+ Fibrin thrombi, 1+ | No significant lesion | No significant lesion |
| MER1-02-4001 | 50 mg/kg/day | No significant lesion | No significant lesion | No significant lesion | No significant lesion |
| MER1-02-4003 | 50 mg/kg/day | No significant lesion | No significant lesion | No significant lesion | No significant lesion |
| MER1-02-4005 | 50 mg/kg/day | No significant lesion | No significant lesion | No significant lesion | No significant lesion |
| MER1-02-5001 | 60 mg/kg/day | Vasculitis, 1+ | Cardiomyopathy, 1+ | No significant lesion | No significant lesion |
| MER1-02-5003 | 60 mg/kg/day | No significant lesion | No significant lesion | No significant lesion | No significant lesion |
| MER1-02-5005 | 60 mg/kg/day | Perivasculitis, 1+ | No significant lesion | No significant lesion | No significant lesion |
| MER1-02-6001 | 70 mg/kg/day | No significant lesion | No significant lesion | No significant lesion | No significant lesion |
| MER1-02-6003 | 70 mg/kg/day | Perivasculitis, 1+ | No significant lesion | No significant lesion | No significant lesion |
| MER1-02-6005 | 70 mg/kg/day | Vasculitis, 1+ Fibrin thrombi, 1+ | No significant lesion | No significant lesion | No significant lesion |
| MER1-02-7001 | 80 mg/kg/day | No significant lesion | No significant lesion | No significant lesion | No significant lesion |
| MER1-02-7003 | 80 mg/kg/day | No significant lesion | No significant lesion | CL Hypertrophy, 1+ | No significant lesion |
| MER1-02-7005 | 80 mg/kg/day | No significant lesion | No significant lesion | CL Hypertrophy, 1+ Hemorrhage, 1+ | No significant lesion |
| MER1-02-8001 | 90 mg/kg/day | Perivasulitis, 1+ | No significant lesion | CL Hypertrophy, 1+ | No significant lesion |
| MER1-02-8003 | 90 mg/kg/day | No significant lesion | No significant lesion | CL Hypertrophy, 1+ | No significant lesion |
| MER1-02-8005 | 90 mg/kg/day | No significant lesion | No significant lesion | CL Hypertrophy, 1+ | No significant lesion |
| MER1-02-9001 | 100 mg/kg/day | No significant lesion | No significant lesion | CL Hypertrophy, 1+ | No significant, lesion |
| MER1-02-9003 | 100 mg/kg/day | No significant lesion | Perivasculitis, 1+ | CL Hypertrophy, 1+ | No significant lesion |
| MER1-02-9005 | 100 mg/kg/day | Fibrin thrombi, 1+ | No significant lesion | CL Hypertrophy, 1+ | No significant lesion |

| Lesion | 30 mg/kg | 40 mg/kg | 50 mg/kg | 60 mg/kg | 70 mg/kg | 80 mg/kg/d | 90 mg/kg/d | 100 mg/kg/d |
|---|---|---|---|---|---|---|---|---|
| Vasculitis/ perivasculitis | 1/3 | 1/3 | 0/3 | 2/3 | 2/3 | 0/3 | 1/3 | 0/3 |
| Fibrin thrombi | 1/3 | 2/3 | 0/3 | 0/3 | 1/3 | 0/3 | 0/3 | 1/3 |
| CL Hypertrophy | 0/3 | 0/3 | 0/3 | 0/3 | 0/3 | 2/3 | 3/3 | 3/3 |

The vasculitis/perivasculitis/and fibrin thrombi are considered part of the same process, and are related to IV administration of MER1. In this study, there is not a no-observed-effect-level for the vasculitis. At the higher does (80 mg/kg/d and above) there was central lobular hypertophy of hepatocytes in the liver (CL Hypertrophy). This finding is not uncommon when a xenobiotic is metabolized in the liver, and the enlarged cells are indicative of smooth endoplasmic reticulum increase. This could be confirmed by measuring enzyme induction in the liver.

TABLE 13

MER-1 Multiple Dose Toxicology

MER1 Multiple Dose 28 d Toxicology

Strain: Swiss Webster  
Age at Start: ~16 wks  
Group Size: 5/sex, male and female  
Groups: 110, 120, 130, 140, 150 mg/kg/d  
Dosing Frequency: Daily × 5  
Dosing Volume: ~10 mL/kg  
Vehicle: Saline, pH w/NaOH to 5.0  
Lot: Merida Sotelo notebook, p43, May 10, 2001, M.P. 151 degrees Objective: To investigate the potential toxicity and maximally-tolerated cumulative dose of MER1 when given intravenously (tail vein) daily × 5 to mice. Total cumulative dose = 500, 550, 600, 650, 700, 750 mg/kg.
Parameters Evaluated: Clinical signs (daily), body weight (pre dose and twice weekly) × 4 weeks. Necropsy moribund/dead animals. Necropsy surviving animals (d 27, Friday Jun. 14, 2002).
To process and read: Heart, lung, kidney, liver in moribund/dead animals and in surviving animals (d 28) in control (0 mg/kg) and high dose groups.

| | MER1-Related Findings | | | |
|---|---|---|---|---|
| mg/kg/day | 0 | 110 | 120 | 130 |
| Conclusions: | • | | | |
| Death | | 2F 2M d2, 3M d3 | 1F d1, 2F 5M d2, 1F d4 | 2F 5M d2, 1F d3, 1F d4, 1F d5 |
| Comment: | • | | | |
| Clinical Signs | | Decr. activity, rough hair coat, tail necrosis. | | |
| Comment: | | | | |
| Fd Consump | N/A | N/A | N/A | N/A |
| Body Weights | Male / Female | Male / Female | Male / Female | Male / Female |
| Average Weight→ | 51 g / 40 g | 50 g / 38 g | 49 g / 36 g | 48 g / 35 g |
| Standard Deviation→ | 0.5477 / 0 | 0.4472 / 1.3038 | 0.5477 / 0.5477 | 0.5477 / 0.5477 |

| | MER1-Related Findings | |
|---|---|---|
| mg/kg/day | 140 | 150 |
| Death | 2F 2M d1, 3F 3M d2 | 3F 5M d1, 2F d2 |
| Comment: | | |
| Clinical Signs | Decr. activity & rough hair coat. | |
| Comment: | | |
| Fd Consump | N/A | N/A |
| Body Weights | Male / Female | Male / Female |
| Average Weight→ | 47 g / 34 g | 46 g / 33 g |
| Standard Deviation→ | 0 / 0.4472 | 0.5477 / 0 |

| | | | | |
|---|---|---|---|---|
| mg/kg/day | 70 | 80 | 90 | 100 |
| Death | — | — | — | — |
| Comment: | Initial period of hyperactivity after dosing, followed by moderately decreased activity. Normal activity resumed 2–3 hours after dosing. | | | |
| Clinical Signs | | | | |
| Fd Consump | N/A | N/A | N/A | N/A |
| Body Weights | Male / Female | Male / Female | Male / Female | Male / Female |
| | 35 g / — | 35 g / — | 29 g / — | 31 g / — |

Histopathology 28 d

| mg/kg/day | 0 | | | |
|---|---|---|---|---|
| Death | — | — | — | — |
| Comment: | | | | |
| Clinical Signs | | | | |
| Fd Consump | — | — | — | |

TABLE 13-continued

MER-1 Multiple Dose Toxicology

| Body Weights | Male | Female | Male | Female | Male | Female | Male | Female |
|---|---|---|---|---|---|---|---|---|
| | | — | | — | | — | | — |
| Histopathology 28 d | | | | | | | | | mg/kg/day

| | MER1-Related Findings | | | | | | | |
|---|---|---|---|---|---|---|---|---|
| Gross Path - | 00 | | 110 | | 120 | | 130 | |
| | Male | Female | Male | Female | Male | Female | Male | Female |
| Organ wts (rel. to brain) | — | — | — | — | — | — | | |
| Comment: | — | — | — | — | | | | |
| Histopathology | — | — | — | — | | | | |
| Sex | • | | | | | | | |
| Dose: mg/kg/day | | | | | | | | |
| Lung/Heart: | F | M | F | M | F | M | F | M |
| 28 d Total | | | | | | | | |
| Ovary: | | | | | | | | |
| 28 d Total | | | | | | | | |
| Comment: | | | | | | | | |

| mg/kg/day | • | | | | | | | |
|---|---|---|---|---|---|---|---|---|
| Gross Path - | | 140 | | 150 | | | | |
| | Male | Female | Male | Female | Male | Female | Male | Female |
| Organ wts (rel. to brain) | — | — | — | — | — | — | | |
| Comment: | — | — | — | — | | | | |
| Histopathology | — | — | — | — | | | | |
| Sex | • | | | | | | | |
| Dose: mg/kg/day | | | | | | | | |
| Lung/Heart: | F | M | F | M | F | M | F | M |
| 28 d Total | | | | | | | | |
| Ovary: | | | | | | | | |
| 28 d Total | | | | | | | | |
| Comment: | | | | | | | | |

Unless indicated otherwise, values = treatment group mean ÷ control group mean.
"—" indicates no compound-related finding.

TABLE 14

Mortality and Number of Doses Tolerated for MER1

| No. of doses | 110 mg/kg Number of animals/dose | | 120 mg/kg Number of animals/dose | | 130 mg/kg Number of animals/dose | | 140 mg/kg Number of animals/dose | | 150 mg/kg Number of animals/dose | |
|---|---|---|---|---|---|---|---|---|---|---|
| | F | M | F | M | F | M | F | M | F | M |
| 1 | 1/5 | | 2/5 | 2/5 | | 4/5 | 4/5 | 4/5 | 5/5 | 5/5 |
| 2 | 1/5 | 2/5 | 1/5 | 3/5 | 2/5 | 1/5 | 1/5 | 1/5 | | |
| 3 | | 3/5 | | | 1/5 | | | | | |
| 4 | | | 1/5 | | 1/5 | | | | | |
| 5 | 3/5 | | 1/5 | | 1/5 | | | | | |

Based on mortality, there is not a no-observable-effect level (NOEL) for this study.

TABLE 15

Summary of Histopathological Findings for MER1 Treated Females

| Animal ID | # doses | Sac. or Death-date | Diagnoses and/observations |
|---|---|---|---|
| | | | 0 mg/kg/day females |
| MER1-03-1002 | 5 | S-Jun. 14, 2002 | Heart: no significant lesions<br>Lungs: no significant lesions<br>Liver: no significant lesions<br>Kidney: Modest, 1 + focal lymphoid aggregate |
| MER1-03-1004 | 5 | S-Jun. 14, 2002 | Heart: no significant lesions<br>Lungs: no significant lesions<br>Liver: no significant lesions<br>Kidney: Modest, 1 + multifocal lymphoid aggregates |
| MER1-03-1006 | 5 | S-Jun. 14 2002 | Heart: no significant lesions<br>Lungs: no significant lesions<br>Liver: no significant lesions |

TABLE 15-continued

Summary of Histopathological Findings for MER1 Treated Females

| Animal ID | # doses | Sac. or Death-date | Diagnoses and/observations |
|---|---|---|---|
| MER1-03-1008 | 5 | S-Jun. 14, 2002 | Kidney: Modest, 1 + focal subacute/chronic inflammation<br>Heart: no significant lesions<br>Lungs: no significant lesions<br>Liver: no significant lesions |
| MER1-03-1010 | 5 | S-Jun. 14, 2002 | Kidney: Modest, 1 + focal subacute/chronic inflammation<br>Heart: no significant lesions<br>Lungs: no significant lesions<br>Liver: no significant lesions<br>Kidney: no significant lesions |
| 110 mg/kg/day females | | | |
| MER1-03-2002 | 5 | S-Jun. 14, 2002 | Heart: no significant lesions<br>Lungs: no significant lesions<br>Liver: no significant lesions<br>Kidney: no significant lesions |
| MER1-03-2004 | 1 | S-May 20, 2002 | Heart: no significant lesions<br>Lungs: no significant lesions<br>Liver: no significant lesions<br>Kidney: Mild, 2 + cell death, lymphoid aggregates |
| MER1-03-2006 | 5 | S-Jun. 14, 2002 | Heart: no significant lesions<br>Lungs: no significant lesions<br>Liver: no significant lesions<br>Kidney: no significant lesions<br>Tail: Severe, 4 + acute necrosis with vasculitis, thrombosis, and ulcerative dermatitis |
| MER1-03-2008 | 2 | S-May 20, 2002 | Heart: no significant lesions<br>Lungs: no significant lesions<br>Liver: no significant lesions<br>Kidney: modest, 1 + tubular necrosis, medulla |
| MER1-03-2010 | 5 | S-Jun. 14, 2002 | Heart: no significant lesions<br>Lungs: Modest, 1 + hypertrophy/hyperplasia, alveolar macrophages<br>Liver: no significant lesions<br>Kidney: no significant lesions |
| 120 mg/kg/day females | | | |
| MER1-03-3002 | 1 | S-May 5, 2002 | Heart: no significant lesions<br>Lungs: Modest, 1 + fibrin thrombus<br>Liver: no significant lesions<br>Kidney: no significant lesions |
| MER1-03-3004 | 2 | S-May 20, 2002 | Heart: no significant lesions<br>Lungs: no significant lesions<br>Liver: no significant lesions<br>Kidney: no significant lesions |
| MER1-03-3006 | 5 | S-Jun. 14 2002 | Heart: no significant lesions<br>Lungs: no significant lesions<br>Liver: no significant lesions<br>Kidney: Modest, 1 + focal lymphoid aggregate<br>Tail: Severe, 4 + acute necrosis with vasculitis, thrombosis, and ulcerative dermatitis |
| MER1-03-3008 | 4 | S-May 22, 2002 | Heart: no significant lesions<br>Lungs: Modest, 1 + fibrin thrombus<br>Liver: Mild, 2 + centrilobular hepatocyte hypertrophy w/ vacuolar degeneration<br>Kidney: no significant lesions<br>Tail: Moderate, 3 + acute necrosis with vasculitis, thrombosis, and ulcerative dermatitis |
| MER1-03-3010 | 1 | S-May 20, 2002 | Heart: no significant lesions<br>Lungs: Modest, 1 + thrombosis, veins<br>Liver: Moderate, 3 + hypertrophy panlobular hepatocytes w/vacuolar degeneration |
| | | | Kidney: Mild, 2 + tubular necrosis, C-M junction |
| 130 mg/kg/day females | | | |
| MER1-03-4002 | 2 | S-May 20, 2002 | Heart: no significant lesions<br>Lungs: no significant lesions<br>Liver: no significant lesions<br>Kidney: no significant lesions |
| MER1-03-4004 | 4 | S-May 22, 2002 | Heart: no significant lesions<br>Lungs: no significant lesions<br>Liver: no significant lesions<br>Kidney: no significant lesions<br>Tail: Severe, 4 + acute necrosis with vasculitis, thrombosis, and ulcerative dermatitis |
| MER1-03-4006 | 5 | S-May 19, 2002 | Heart: no significant lesions<br>Lungs: no significant lesions<br>Liver: no significant lesions<br>Kidney: no significant lesions |
| MER1-03-4008 | 2 | S-May 20, 2002 | Heart: no significant lesions<br>Lungs: no significant lesions<br>Liver: 1. Moderate, 3 + hypertrophy panlobular hepatocytes w/ vacuolar degeneration; 2. Modest, 1 + focal subacute/chronic inflammation, portal area<br>Kidney: no significant lesions |
| MER1-03-4010 | 3 | S- May 21, 2002 | Heart: no significant lesions<br>Lungs: Mild, 2 + acute thrombophlebitits, veins<br>Liver: no significant lesions<br>Kidney: no significant lesions<br>Tail: Moderate, 3 + acute necrosis with vasculitis, thrombosis, and hemorrhage |
| 140 mg/kg/day females | | | |
| MER1-03-5002 | 2 | S-May 20, 2002 | Heart: no significant lesions<br>Lungs: Modest, 1 + fibrin thrombus<br>Liver: no significant lesions<br>Kidney: no significant lesions |
| MER1-03-5004 | 1 | S-May 19, 2002 | Heart: no significant lesions<br>Lungs: Moderate, 3 + acute congestion & hemorrhage<br>Liver: no significant lesions<br>Kidney: no significant lesions |
| MER1-03-5006 | 1 | S-May 20, 2002 | Heart: no significant lesions<br>Lungs: no significant lesions<br>Liver: no significant lesions<br>Kidney: no significant lesions |
| MER1-03-5008 | 1 | D-May 20, 2002 | Heart: no significant lesions<br>Lungs: no significant lesions<br>Liver: Mild to moderate, 2–3 + acute hepatocellular necrosis<br>Kidney: no significant lesions |
| MER1-03-5010 | 1 | S-May 19, 2002 | Heart: no significant lesions<br>Lungs: Modest, 1 + vasculitis & fibrin thrombus<br>liver: no significant lesions<br>Kidney: no significant lesions |
| 150 mg/kg/day females | | | |
| MER1-03-6002 | 1 | D-May 20, 2002 | Heart: no significant lesions<br>Lungs: no significant lesions<br>Liver: no significant lesions<br>Kidney: no significant lesions |
| MER1-03-6004 | 1 | S-May 19, 2002 | Heart: no significant lesions<br>Lungs: Moderate, 3 + acute fibrin thrombosis, alveolar capillaries<br>Liver: no significant lesions<br>Kidney: no significant lesions |
| MER1-03-6006 | 1 | S-May 20, 2002 | Heart: no significant lesions<br>Lungs: no significant lesions |

TABLE 15-continued

Summary of Histopathological Findings for MER1 Treated Females

| Animal ID | # doses | Sac. or Death-date | Diagnoses and/observations |
|---|---|---|---|
| MER1-03-6008 | 1 | S-May 19, 2002 | Liver: no significant lesions<br>Kidney: no significant lesions<br>Heart: no significant lesions<br>Lungs: Mild, 2 + acute fibrin thrombosis, alveolar capillaries<br>Liver: Moderate, 3 + hypertrophy panlobular hepatocytes w/vacuolar degeneration<br>Kidney: no significant lesions |
| MER1-03-6010 | 1 | S-May 19, 2002 | Heart: no significant lesions<br>Lungs: no significant lesions<br>Liver: no significant lesions<br>Kidney: no significant lesions |

TABLE 16

Summary of Histopathological Findings for MER1 Treated Males

| Animal ID | # doses | Sac. or Death-date | Diagnoses and/observations |
|---|---|---|---|
| *0 mg/kg/day males* | | | |
| MER1-03-1001 | 5 | S-Jun. 14, 2002 | Heart: no significant lesions<br>Lungs: no significant lesions<br>Liver: 1. Moderate 3 +, increased cytoplasmic glycogen, hepatocytes<br>2. Modest 1 +, focal acute necrosis<br>Kidney: no significant lesions |
| MER1-03-1003 | 5 | S-Jun. 14, 2002 | Heart: no significant lesions<br>Lungs: no significant lesions<br>Liver: no significant lesions<br>Kidney: no significant lesions |
| MER1-03-1005 | 5 | S-Jun. 14, 2002 | Heart: no significant lesions<br>Lungs: no significant lesions<br>Liver: no significant lesions<br>Kidney: no significant lesions |
| MER1-03-1007 | 5 | S-Jun. 14, 2002 | Heart: no significant lesions<br>Lungs: no significant lesions<br>Liver: no significant lesions<br>Kidney: no significant lesions |
| MER1-03-1009 | 5 | S-Jun. 14, 2002 | Heart: 1. Moderate, 3 + medial hyperplasia, coronary arteries<br>2. Mild, 2 + polyarteritis, coronary arteries<br>Lungs: no significant lesions<br>Liver: no significant lesions<br>Kidney: no significant lesions |
| *110 mg/kg/day males* | | | |
| MER1-03-2001 | 3 | S-May 21, 2002 | Heart: no significant lesions<br>Lungs: no significant lesions<br>Liver: no significant lesions<br>Kidney: no significant lesions |
| MER1-03-2003 | 2 | S-May 20, 2002 | Heart: no significant lesions<br>Lungs: no significant lesions<br>Liver: no significant lesions<br>Kidney: no significant lesions |
| MER1-03-2005 | 3 | S-May 21, 2002 | Heart: 1. Mild, 2 + acute sub-endocardial myocarditis<br>2. Mild, 2 + myocyte vacuolation<br>Lungs: no significant lesions<br>Liver: no significant lesions<br>Kidney: no significant lesions |
| MER1-03-2007 | 2 | S-May 20, 2002 | Heart: no significant lesions<br>Lungs: Mild, 2 + acute hemorrhage<br>Liver: Modest, 1 + centrilobular hepatocyte hypertrophy w/vacuolar degeneration (microvescicular)<br>Kidney: no significant lesions |
| MER1-03-2009 | 3 | S-May 21, 2002 | Heart: no significant lesions<br>Lungs: Mild, 2+ acute hemorrhage<br>Liver: , 1 + centrilobular hepatocyte hypertrophy<br>Kidney: Mild, 2 + lymphoid hyperplasia, pelvis & perivascular |
| *120 mg/kg/day males* | | | |
| MER1-03-3001 | 2 | S-May 20, 2002 | Heart: no significant lesions<br>Lungs: no significant lesions<br>Liver: Mild, 2 + cystic hyaline degeneration of hepatocytes<br>Kidney: no significant lesions |
| MER1-03-3003 | 2 | S-May 20, 2002 | Heart: no significant lesions<br>Lungs: no significant lesions<br>Liver: no significant lesions<br>Kidney: no significant lesions |
| MER1-03-3005 | 2 | S-May 20, 2002 | Heart: no significant lesions<br>Lungs: no significant lesions<br>Liver: no significant lesions<br>Kidney: Modest, 1 + hyaline casts tubules, medulla |
| MER1-03-3007 | 1 | S-May 20, 2002 | Heart: no significant lesions<br>Lungs: Modest, 1 + acute thrombophlebitis<br>Liver: no significant lesions<br>Kidney: no significant lesions |
| MER1-03-3009 | 1 | D-May 20, 2002 | Heart: no significant lesions<br>Lungs: Modest, 1 + vasculitis<br>Liver: no significant lesions<br>Kidney: no significant lesions |
| *130 mg/kg/day males* | | | |
| MER1-03-4001 | 1 | D-May 20, 2002 | Heart: no significant lesions<br>Lungs: 1. Mild, 2 + acute hemorrhage; 2. Modest, 1 + fibrin thrombus<br>Liver: no significant lesions<br>Kidney: Mild, 2 + acute tubular necrosis |
| MER1-03-4003 | 1 | D-May 20, 2002 | Heart: no significant lesions<br>Lungs: no significant lesions<br>Liver: no significant lesions<br>Kidney: no significant lesions |
| MER1-03-4005 | 1 | D-May 20, 2002 | Heart: no significant lesions<br>Lungs: Mild, 2 + acute hemorrhage<br>Liver: no significant lesions<br>Kidney: Mild, 2 + acute tubular necrosis |
| MER1-03-4007 | 2 | S-May 20, 2002 | Heart: no significant lesions<br>Lungs: Modest, 1 + acute hemorrhage<br>Liver: Mild, 2 + fatty change hepatocytes<br>Kidney: Modest, 1 + acute tubular necrosis |
| MER1-03-4009 | 1 | D-May 20, 2002 | Heart: no significant lesions<br>Lungs: Modest, 1 + fibrin thrombus<br>Liver: no significant lesions<br>Kidney: no significant lesions |
| *140 mg/kg/day males* | | | |
| MER1-03-5001 | 2 | S-May 20 2002 | Heart: no significant lesions<br>Lungs: no significant lesions<br>Liver: no significant lesions<br>Kidney: no significant lesions |
| MER1-03-5003 | 1 | S-May 20, 2002 | Heart: no significant lesions<br>Lungs: Modest, 1 + acute venous thrombosis<br>Liver: Moderate, 3 + hypertrophy panlobular hepatocytes<br>Kidney: Mild, 2 + lymphoid hyperplasia, pelvis |

TABLE 16-continued

Summary of Histopathological Findings for MER1 Treated Males

| Animal ID | # doses | Sac. or Death-date | Diagnoses/observations |
|---|---|---|---|
| MER1-03-5005 | 1 | D-May 20, 2002 | Heart: no significant lesions<br>Lungs: no significant lesions<br>Liver: no significant lesions<br>Kidney: no significant lesions |
| MER1-03-5007 | 1 | D-May 19, 2002 | Heart: Moderate, 3 + medial hyperplasia, coronary arteries<br>Lungs: Moderate, 3 + atelectasis<br>Liver: no significant lesions<br>Kidney: no significant lesions |
| MER1-03-5009 | 1 | D-May 19, 2002 | Heart: no significant lesions<br>Lungs: Modest, 1 + acute hemorrhage<br>Liver: Mild, 2 + hypertrophy panlobular hepatocytes<br>Kidney: Mild, 2 + infarct kidney |
| 150 mg/kg/day males | | | |
| MER1-03-6001 | 1 | S-May 19, 2002 | Heart: Mild, 2 + medial hyperplasia, coronary arteries<br>Lungs: Mild, 2 + acute hemorrhage<br>Liver: Mild, 2 + hypertrophy panlobular hepatocytes<br>Kidney: no significant lesions |
| MER1-03-6003 | 1 | S-May 19, 2002 | Heart: no significant lesions<br>Lungs: Modest, 1 + thrombosis, veins & capillaries<br>Liver: Mild, 2 + hypertrophy panlobular hepatocytes<br>Kidney: no significant lesions |
| MER1-03-6005 | 1 | S-May 19, 2002 | Heart: no significant lesions<br>Lungs: Modest, 1 + thrombosis, veins & capillaries<br>Liver: no significant lesions<br>Kidney: no significant lesions |
| MER1-03-6007 | 1 | S-May 19, 2002 | Heart: no significant lesions<br>Lungs: no significant lesions<br>Liver: no significant lesions<br>Kidney: no significant lesions |
| MER1-03-6009 | 1 | S-May 19, 2002 | Heart: no significant lesions<br>Lungs: no significant lesions<br>Liver: no significant lesions<br>Kidney: no significant lesions |

The results of the MER1 Multiple Dose I.V. toxicology study evaluating 110, 120, 130, 140, and 150 mg/kg daily×5, are summarized as follows: The study focused on the microscopic examination of heart, lung liver, and kidney. Medial hyperplasia of coronary arteries is usually a spontaneous lesion that is more common in male mice than in female mice. Inflammatory lesions, e.g. lymphocyte aggregates, in the kidney and liver are concluded to be incidental findings unrelated to MER1. Hepatocyte hypertrophy and acute necrosis of renal tubules are lesions of uncertain significance encountered inconsistently in treated mice of both sexes. The panlobular hypertrophy observed in males at the higher doses was sometimes associated with a microvesicular vacuolation suggesting possible hepatic toxicity. These animals generally were sacrificed in extremis after a single dose. Vascular lesions in lungs of these multi-dose mice are not consistent or striking when present although vasculopathies were common in the single-dose study of MER1. The tolerance of fewer doses and greater mortality in male mice suggests that the male gender is more sensitive to toxic effects of this compound. Analysis for a difference in metabolism in the liver between the sexes may be helpful.

TABLE 17

SGLU1- Multiple Dose Toxicology In Vivo

SGLU1
Multiple - Dose Toxicity

| Dose Dates Males: Jun. 18, 2002–Jun. 22, 2002 | Dose Dates Females: Jun. 19, 2002–Jun. 23, 2002 |
|---|---|
| Strain: Swiss Webster | Dosing Frequency: Daily × 5 |
| Age at Start: ~6 wks | Dosing Volume: 10 mL/kg |
| Group Size: 5/grp, male and female | Vehicle: Saline |
| Groups: 0, 50, 100, 150, 200, 250, 300, and 350 mg/kg/d | Lot: xxxxxxxxx |

Objective: To investigate the potential toxicity and LD10–LD90 of SGLU1 when given intravenously (tail vein) daily × 5 to mice. Total cumulative dose = 250, 500, 750, 1000, 1250, 1500 and 1750 mg/kg. (IV single dose MTD = 350 mg/kg)
Parameters Evaluated: Clinical signs (daily), body weight (pre dose and twice weekly) × 4 weeks. Necropsy moribund/dead animals.
To process and read: Heart, lung, kidney, liver in moribund/dead animals and in surviving animals (d 28) in control (0 mg/kg) and high dose groups.

| | SGLU1 -Related Findings | | | | | | | |
|---|---|---|---|---|---|---|---|---|
| mg/kg/day | 50 | | 100 | | 150 | | 200 | |
| Conclusions: | • | | | | | | | |
| Death | — | | — | | — | | — | |
| Comment: | • | | | | | | | |
| Clinical Signs | None. | | None. | | None. | | 2 F tail necrosis: amputate | |
| Body Weights | Male | Female | Male | Female | Male | Female | Male | Female |
| Avg. in grams | 25 | 25 | 23 | 24 | 23 | 25 | 24 | 24 |
| Std Dev. | 0.707 | 0.837 | 1.304 | 0.837 | 0.707 | 0.894 | 0.894 | 0.447 |
| Comment: | • | | | | | | | |

TABLE 17-continued

| SGLU1- Multiple Dose Toxicology In Vivo | | | | | | | | |
|---|---|---|---|---|---|---|---|---|
| mg/kg/day | 250 | | 300 | | 350 | | 0 | |
| Death | 1F d4 | | 3F d2, 1M d3 | | 2M d1, 4F d1 1M d2, 1F d2 | | — | |
| Comment: | | | | | | | | |
| Clinical Signs | 2 M tail necr.: amputate | | Slight decr. activity 1 F tail necr.: amputate | | Moderate decr. activity 2 M tail necr.: amputate | | None. | |
| Body Weights | Male | Female | Male | Female | Male | Female | Male | Female |
| Avg. in grams | 24 | 24 | 23 | 24 | 20 | 24 | 26 | 26 |
| Std Dev. | 0.837 | 0.894 | 0.837 | 0.894 | 1.140 | 0.894 | 0.894 | 0.837 |
| Comment: | • | | | | | | | |

Unless indicated otherwise, values = treatment group mean ÷ control group mean.
"—" indicates no compound-related finding.

The results of the SGLU-1 Multiple Dose I.V. are summarized as follows: Five mice/sex were administered 5 daily intravenous injections of SGLU via the tail vein at doses of 50, 100, 150, 200, 250, 300, and 350 mg/kg/day. All surviving mice were held for 28 days, sacrificed, and designated tissues collected, formalin fixed, and examined.

Deaths occurred at 250, 300, and 350 mg/kg/day with female mice being more susceptible than males. Microscopic observations noted compound-related lesions in lung, liver, thymus, and testes. The no-observable-effect level for female mice in this study is 150 mg/kg and is based on the centrilobular hypertrophy of hepatocytes in 1/5 female mice at 200 mg/kg/day. The no-observable-effect level (NOEL) for male mice in this study is 100 mg/kg/day and is based on testicular seminiferous tubular degeneration in 1/5 males at 150 mg/kg/day.

TABLE 18

| | Deaths | | | | | | | | | | | | | |
|---|---|---|---|---|---|---|---|---|---|---|---|---|---|---|
| | 50 mg/kg/day Number of animals/dose | | 100 mg/kg/day Number of animals/dose | | 150 mg/kg/day Number of animals/dose | | 200 mg/kg/day Number of animals/dose | | 250 mg/kg/day Number of animals/dose | | 300 mg/kg/day Number of animals/dose | | 350 mg/kg/day Number of animals/dose | |
| | F | M | F | M | F | M | F | M | F | M | F | M | F | M |
| Deaths | 0/5 | 0/5 | 05/ | 0/5 | 0/5 | 0/5 | 0/5 | 0/5 | 1/5 | 0/5 | 3/5 | 1/5 | 5/5 | 3/5 |

TABLE 19

| | Number of Doses Tolerated | | | | | | | | | | | | | |
|---|---|---|---|---|---|---|---|---|---|---|---|---|---|---|
| No. of doses | 50 mg/kg/day Number of animals/dose | | 100 mg/kg/day Number of animals/dose | | 150 mg/kg/day Number of animals/dose | | 200 mg/kg/day Number of animals/dose | | 250 mg/kg/day Number of animals/dose | | 300 mg/kg/day Number of animals/dose | | 350 mg/kg/day Number of animals/dose | |
| | F | M | F | M | F | M | F | M | F | M | F | M | F | M |
| 1 | | | | | | | | | | | 1/5 | 3/5 | 4/5 | 3/5 |
| 2 | | | | | | | | | | | 2/5 | | 1/5 | |
| 3 | | | | | | | | | | | | | | |
| 4 | | | | | | | | | 1/5 | | | | | |
| 5 | 5/5 | 5/5 | 5/5 | 5/5 | 5/5 | 5/5 | 5/5 | 5/5 | 4/5 | 5/5 | 2/5 | 2/5 | | 2/5 |

TABLE 20

Compound-Related Lesions
Incidences of Test Substance-Related Microscopic Changes in Female and Male Mice

| | Group Designation | | | | | | | | | | | | | | | |
|---|---|---|---|---|---|---|---|---|---|---|---|---|---|---|---|---|
| | 1 | | 2 | | 3 | | 4 | | 5 | | 6 | | 7 | | 8 | |
| | Concentration (mg/kg/day) | | | | | | | | | | | | | | | |
| | 0 | | 50 | | 100 | | 150 | | 200 | | 250 | | 300 | | 350 | |
| | Number of Mice in Group | | | | | | | | | | | | | | | |
| | 5 | | 5 | | 5 | | 5 | | 5 | | 5 | | 5 | | 5 | |
| | F | M | F | M | F | M | F | M | F | M | F | M | F | M | F | M |
| Lungs: | | | | | | | | | | | | | | | | |
| Fibrin thrombi | — | — | — | — | — | — | — | — | — | — | — | — | — | — | 1/5 | 1/5 |
| Vasculitis | — | — | — | — | — | — | — | — | — | — | — | — | 1/5 | — | 1/5 | — |
| Liver: | | | | | | | | | | | | | | | | |
| Hepatocyte hypertrophy | | | | | | | | | | | | | | | | |
| Centrilobular (compatible with SER) | — | — | — | — | — | — | — | — | 1/5 | — | 1/5 | 5/5 | 2/5 | 4/5 | — | 1/5 |
| Panlobular w/eosinophilia | — | — | — | — | — | — | — | — | — | — | — | — | 1/5 | — | — | — |
| Periportal w/vacuolation | — | — | — | — | — | — | — | — | — | — | — | — | — | — | 2/5 | — |
| Thymus: | | | | | | | | | | | | | | | | |
| Apoptosis, increased | — | — | — | — | — | — | — | — | — | — | — | — | — | — | 5/5 | 2/5 |
| Testes: | | | | | | | | | | | | | | | | |
| Seminiferous tubule degeneration | — | — | — | — | — | — | — | — | 1/5 | — | 1/5 | — | 2/5 | — | 2/5 | — | 5/5 |
| Epididymis: | | | | | | | | | | | | | | | | |
| Oligospermia | — | — | — | — | — | — | — | — | 1/5 | — | 1/5 | — | 2/5 | — | 5/5 | |

[a] Indicates number of mice with microscopic lesion.

TABLE 21

Summary Incidences of All Microscopic Observations

| | Group 1 0 mg/kg Incidence Per organ Examined | | Group 2 50 mg/kg Incidence Per organ Examined | | Group 3 100 mg/kg Incidence Per organ Examined | | Group 4 150 mg/kg Incidence Per organ Examined | | Group 5 200 mg/kg Incidence Per organ Examined | | Group 6 250 mg/kg Incidence Per organ Examined | | Group 7 300 mg/kg Incidence Per organ Examined | | Group 8 350 mg/kg Incidence Per organ Examined | |
|---|---|---|---|---|---|---|---|---|---|---|---|---|---|---|---|---|
| Organ: Microscopic Observation | F | M | F | M | F | M | F | M | F | M | F | M | F | M | F | M |
| Heart: | | | | | | | | | | | | | | | | |
| Cardiomyopathy | — | — | — | — | — | — | — | — | — | — | — | — | — | — | — | — |
| Interstitial fat, increased | — | — | — | — | — | — | — | — | — | — | 1/5 | — | — | — | — | — |
| Medial hyprtrophy, coronary artery | — | — | — | — | — | — | — | — | — | — | — | — | — | 1/5 | — | — |
| Lung: | | | | | | | | | | | | | | | | |
| Congestion | — | — | — | — | — | — | — | — | — | — | — | — | 3/5 | 1/5 | 2/5 | — |
| Fibrin Thrombi | — | — | — | — | — | — | — | — | — | — | — | — | — | — | 1/5 | 1/5 |
| Thrombus, organized | — | 1/5 | — | — | — | — | — | — | — | — | — | — | — | — | — | — |
| Vasculitis | — | — | — | — | — | — | — | — | — | — | — | — | 1/5 | — | 1/5 | — |
| Hemorrhage, focal | — | — | 1/5 | — | — | — | — | — | — | — | — | — | — | — | — | 2/5 |
| Pleural adhesion, focal | — | — | — | — | 1/5 | — | — | — | — | — | — | — | — | — | — | — |
| Atelectasis | — | — | — | — | 1/5 | — | — | — | — | — | — | — | 1/5 | — | — | — |
| Inflammation, focal | — | — | — | — | — | — | — | 1/5 | — | — | 1/5 | — | — | — | — | — |
| Liver: | | | | | | | | | | | | | | | | |
| Pyogranuloma, focal | 2/5 | 1/5 | 1/5 | 1/5 | 5/5 | 1/5 | 3/5 | 1/5 | 3/5 | 2/5 | 1/5 | 3/5 | 1/5 | 2/5 | — | 2/5 |
| Inflammation, portal | — | — | — | — | — | — | 2/5 | — | 3/5 | — | 2/5 | — | — | — | 1/5 | — |
| Increased mitoses | — | — | — | — | — | — | — | — | 1/5 | — | — | — | — | — | — | 1/5 |
| Hepatocyte hypertrophy: Centrilobular: | — | — | — | — | — | — | — | — | 1/5 | — | 1/5 | 5/5 | 2/5 | 4/5 | — | 1/5 |
| Panlobular w/eosionphilia: | — | — | — | — | — | — | — | — | — | — | — | — | 1/5 | — | — | — |
| Periportal w/vacuolation: | — | — | — | — | — | — | — | — | — | — | — | — | — | — | 2/5 | — |
| Focus of Alteration, eosinophilic | — | — | — | — | — | — | — | — | — | — | 1/5 | — | — | — | — | — |

TABLE 21-continued

Summary Incidences of All Microscopic Observations

| Organ:<br>Microscopic Observation | Group 1<br>0 mg/kg<br>Incidence<br>Per organ<br>Examined | | Group 2<br>50 mg/kg<br>Incidence<br>Per organ<br>Examined | | Group 3<br>100 mg/kg<br>Incidence<br>Per organ<br>Examined | | Group 4<br>150 mg/kg<br>Incidence<br>Per organ<br>Examined | | Group 5<br>200 mg/kg<br>Incidence<br>Per organ<br>Examined | | Group 6<br>250 mg/kg<br>Incidence<br>Per organ<br>Examined | | Group 7<br>300 mg/kg<br>Incidence<br>Per organ<br>Examined | | Group 8<br>350 mg/kg<br>Incidence<br>Per organ<br>Examined | |
|---|---|---|---|---|---|---|---|---|---|---|---|---|---|---|---|---|
| | F | M | F | M | F | M | F | M | F | M | F | M | F | M | F | M |
| Ito cell hypertrophy | — | — | — | — | — | — | — | — | — | 1/5 | — | — | — | — | — | — |
| Necrosis, focal | — | — | — | — | — | — | — | — | — | — | — | — | — | — | — | — |
| Kidney: | | | | | | | | | | | | | | | | |
| Murine progressive glomerulonephropathy | — | — | 1/5 | — | — | — | — | — | — | — | — | — | — | — | 1/5 | — |
| Inflammation, focal | — | — | — | — | 2/5 | — | — | 1/5 | 2/5 | — | — | — | — | — | — | 1/5 |
| Congestion | — | — | — | — | — | — | — | — | — | — | — | — | 1/5 | — | — | 1/5 |
| Thymus: | | | | | | | | | | | | | | | | |
| Apoptosis, increased | — | — | — | — | — | — | — | — | — | — | — | — | — | — | 5/5 | 2/5 |
| Spleen: | | | | | | | | | | | | | | | | |
| Extramedullary hematopoiesis, increased | 1/5 | — | — | — | — | — | — | — | — | — | — | — | — | — | — | 1/5 |
| Congestion | — | — | — | — | — | — | — | — | — | — | — | — | — | — | 5/5 | 2/5 |
| Mandibular L. N.: | | | | | | | | | | | | | | | | |
| Apoptosis, lymphocyte | — | — | — | — | — | — | — | — | — | — | — | — | — | — | 1/5 | — |
| Testes: | | | | | | | | | | | | | | | | |
| Seminiferous tubular degeneration | — | — | — | — | — | — | — | 1/5 | — | 1/5 | — | 2/5 | — | 2/5 | — | 5/5 |
| Epididymus: | | | | | | | | | | | | | | | | |
| Oligospermia | — | — | — | — | — | — | — | 1/5 | — | 1/5 | — | 2/5 | — | — | — | 5/5 |
| Bone Marrow: | | | | | | | | | | | | | | | | |
| Myeloid hyperplasia | — | — | — | — | — | — | — | — | — | — | — | — | — | — | — | 1/5 |
| Tail: | | | | | | | | | | | | | | | | |
| Acute necrosis with vasculitis, thrombosis, and hemorrhage | — | — | — | — | — | — | 1/5 | 4/5 | — | — | 2/5 | 1/5 | 1/5 | — | 1/5 | |
| Ulcerative dermatitis | — | — | — | — | — | — | 1/5 | 2/5 | — | — | 1/5 | — | 1/5 | — | — | |

Example 10

HPLC Analytical Method Development and Validation

HPLC will be used in the methods development and validation for the use of organic arsenicals. The HPLC methods will include: standard curve and linearity, reproducibility (10 injections minimum), sensitivity (minimum quantifiable concentration; minimum detectable concentration), accuracy (such as using three independently prepared solutions of 0.025 mg/mL, 0.1 mg/mL, 1 mg/mL), intentional degradation from heat, basic solutions acidic solutions and $H_2O_2$, and peak definition for intact drug, bulk impurities and starting materials, and degradation products. Bulk raw drug will be analyzed in a reference standard lot through HPLC analysis of purity, loss on drying, optical rotation, melting point, and visual appearance.

Example 11

Dosage Forms Development

The dosage of organic arsenicals will be developed following the formulation solvent system developed by Pharmacology Laboratory. This includes determining the stability in potential aqueous vehicles and to filtration, selecting target concentration for further development, testing the osmolality and pH and adjusting if necessary, selecting package and closure configuration, determining the thermal stability (autoclaving), testing the visual appearance and particulate burden and determining the target pH values and acceptable range for target concentration.

Example 12

Clinical Trials

This example is concerned with the development of human treatment protocols using the arsenical compounds, MER1, SGLU and SAL-1, and compositions of the invention or the pharmaceutical formulations thereof. These compositions will be of use in the clinical treatment of various cancers including leukemias and other forms of solid cancers and tumors.

The various elements of conducting a clinical trial, including patient treatment and monitoring, will be known to those of skill in the art in light of the present disclosure. The following information is being presented as a general guideline for use in establishing clinical trials using the compositions of the present invention.

Candidates for the phase 1 clinical trial will be patients on which all conventional therapies have failed. Pharmaceutical formulations of MER1, SAL-1 or SGLU-1 will be administered to them intravenously on a tentative schedule of 5 days every 4 weeks. One of skill in the art will appreciate that one may administer the therapeutic formulation of the invention by any alternative route that is suitable depending on the nature of the lesion including administration by any method including local, regional, or systemic administration. Oral and topical applications are also contemplated. A composition of the present invention is typically administered orally or parenterally in dosage unit formulations containing standard, well known non-toxic physiologically acceptable carriers, adjuvants, and vehicles as desired. The term parenteral as used herein includes subcutaneous injections, intravenous, intramuscular, intra-arterial injection, or infusion techniques.

To monitor disease course and evaluate the anti-tumor responses, it is contemplated that the patients should be examined for appropriate tumor markers every month. To assess the effectiveness of the drug, the following parameters will be monitored: tumor size and/or bone marrow infiltration of the cancer cells. Tests that will be used to monitor the progress of the patients and the effectiveness of the treatments may include: physical exam, X-ray, blood work and other clinical laboratory methodologies. The doses given in the phase 1 study will be escalated as is done in standard phase 1 clinical phase trials, i.e. doses will be escalated until maximal tolerable ranges are reached.

Clinical responses may be defined by acceptable measure. For example, a complete response may be defined by complete disappearance of evidence of cancer cells for at least 2 months. Whereas a partial response may be defined by a 50% reduction of cancer cells for at least 2 months.

The clinical trials may be performed with the therapeutic agents of the invention alone or in combination with other anti-cancer drugs and other standard cancer therapies used in the art. The therapeutic compositions of the invention may be delivered to the patient before, after or concurrently with the other anti-cancer agents.

The typical course of treatment will vary depending upon the individual patient and disease being treated in ways known to those of skill in the art. For example, a patient with leukemia might be treated in four week cycles, although longer duration may be used if adverse effects are observed with the patient, and shorter terms of treatment may result if the patient does tolerate the treatment as hoped. Each cycle will consist of 5 individual doses, although this too may be varied depending on the clinical situation. Upon election by the clinician the regimen may be continued with 5 doses every three weeks or on a less frequent basis. Of course, these are only exemplary times for treatment, and the skilled practitioner will readily recognize that many other time-courses are possible.

Patients may, but need not, have received previous chemo-, radio- or gene therapeutic treatments. Optimally the patient will exhibit adequate bone marrow function (defined as peripheral absolute granulocyte count of >2,000/mm$^3$ and platelet count of 100,000/mm$^3$, adequate liver function (bilirubin 1.5 mg/dl) and adequate renal function (creatinine 1.5 mg/dl).

In one embodiment, administration simply entails injection of the therapeutic composition into the tumor. In another embodiment, a catheter is inserted into the site of the tumor and the cavity may be continuously perfused for a desired period of time.

Of course, the above-described treatment regimes may be altered in accordance with the knowledge gained from preclinical trials. Those of skill in the art will be able to take the information disclosed in this specification and optimize treatment regimes based on the clinical trials described in the specification.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

American Conference of Governmental Industrial Hygienists, Inc. (ACGIH). Arsenic and soluble compounds, including arsine. Documentation of the Threshold Limit Values and Biological Exposure Indices, sixth edition, 1991.

Bainbridge, W. S. in *The Cancer Problem*, Macmillian, New York, pp. 271–276, 1914.

Banks, C. H. et al., "Biomolecules bearing the S- or SeAsMe2 function: amino acid and steroid derivatives," *J. Medicinal Chem.* 22:572–575, 1979.

Beliles, R. P. "The Metals," In *Patty's Industrial Hygiene and Toxicology, fourth edition* G. D. Clayton and F. E. Clayton, eds. John Wiley & Sons, Inc.: New York. pp. 1913–1925, 1994.

Chen, G. C. et al., "6-thio- and -seleno-alpha-D-glucose esters of dimethylarsinous acid," *Carb. Res.* 50:53–62, 1976.

Chen, G. C. et al., "Synthesis of 1- and 6-S- and 1- and 6-Se-derivatives of 2-amino-2-deoxy-alpha/beta-D-glucopyranose" *J. Chemical Soc, Perkin Trans.* 1, 2287–2293, 1980.

Cuzick, J. et al., "Medicinal arsenic and internal malignancies," *Br. J. Cancer* 45:904–911, 1982.

Daniel, J. R. and Zingaro, R. A. "Dimethylarsinous acid esters of 1-thio- and -seleno-galactose. A new class of potential carcinostatic agents," *Phosphorus and Sulfur* 4:179–185, 1978.

EP1002537

Forkner, C. and McNair-Scott, T. F. "Arsenic as a therapeutic agent in chronic myeloid leukemia," *JAMA* 97:305, 1931.

Geissler, K. et al., "In vivo effects of arsenic trioxide in refractory acute myeloid leukemia other than acute promyelocytic leukemia," *Blood* 94:4230a, 1999.

Goyer, R. A. "Toxic effects of metals" In *Casarett and Doull's Toxicology: The Basic Science of Poisons*, 5$^{th}$ edition. C. D. Klassen, ed. McGraw-Hill: New York. pp. 691–698, 1996.

Grignani et al., "The acute promyelocytic leukemia-specific PML-RAR alpha fusion protein inhibits differentiation and promotes survival of myeloid precursor cells," *Cell*, 74:423–431, 1993.

Hughes, M. F.; Kenyon, E. M. "Dose-dependent effects on the disposition of monomethylarsonic acid and dimethylarsinic acid in the mouse after intravenous administration" *J. Toxicol. Environ. Health* A 23:53(2) 95–112, 1998.

IARC. Some metals and metallic compounds. IARC Monographs on the Evaluation of the Carcinogenic Risk of Chemicals to Man. Volume 23:39–141, 1980.

Investigational Drug Brochure: Informational Material for Physicians: Melarsoprol (MeL B) (Arsobal). Centers for Disease Control, Atlanta, Ga., 1987.

Investigator's Brochure: Arsenic Trioxide, PolaRx Biopharmaceuticals Inc., New York, N.Y., 1998.

Knock, F. E. et al., "The use of selected sulfhydryl inhibitors in a preferential drug attack on cancer," *Surg. Gynecol Obstet.* 133:458–466, 1971.

Konig, A. et al., "Comparative activity of melarsoprol and arsenic trioxide in chronic B-cell leukemia lines," *Blood* 90:562–570, 1997.

Material Safety Data Sheet: Dimethylarsinic acid, Strem Chemicals Inc., Newburyport, Mass., 1998.

Rivi, R. et al., "Organic arsenical melarsoprol shows growth suppressive activity via programmed cell death on myeloid and lymphoid leukemia derived cell lines," *Blood* (Suppl.) 88:68a, 1996.

Rosenthal, M. V. and Zingaro, R. A. "The synthesis and characterization of thio sugar esters of diorganylarsinous acids," *Phosphorus and Sulfur* 9:107–116, 1980.

Rousselot, P. et al., "Use of arsenic trioxide ($As_2O_3$) in the treatment of chronic myelogenous leukemia: In vitro and in vivo studies," *Blood* 94:4457a, 1999.

Soignet, S. L. et al., "Clinical study of an organic arsenic melarsoprol, in patients with advanced leukemia," *Cancer Chemother. Pharmacol.* 44:471–421, 1999.

Soignet, S. L. et al., "Dose-ranging and clinical pharmacologic study of arsenic trioxide in patients with advanced hematologic cancers," *Blood* 94:1247a, 1999.

Tarnowski, G. S. et al., "Chemotherapy studies in an animal tumor spectrum: II. Sensitivity of tumors to fourteen antitumor chemicals," *Cancer Res.* 26:181–206, 1966.

Wiernik, P. H. et al., "Phase II trial of arsenic trioxide ($As_2O_3$) in patients with relapsed/refractory acute myeloid leukemia, blast crisis of CML or myelodysplasia," Blood 94:2283a, 1999.

WO9924029

Zhang, P. et al., "Arsenic trioxide treated 72 cases of acute promyelocytic leukemia," *Chin. J. Hematol.* 17:58–62, 1996.

What is claimed is:

1. A method for treating cancer, comprising administering a therapeutically effective amount of a compound having a structure

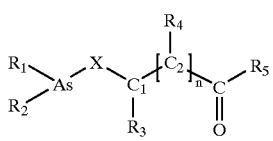

wherein $R_1$ and $R_2$ are independently alkyls with 1–10 carbon atoms;

X is S or Se;

$R_3$ is —H, —COOH, —$CH_2$—COOH, —$CH_2$—$CH_2$—COOH, —CH($CH_3$)—COOH, —CH($CH_2$—$CH_3$)—COOH, or —$CH_2$—$CH_2$—$CH_2$—COOH;

n is 0 or 1;

$R_4$ is —OH, —H, —$CH_3$, or a glutamine substituent; or or $R_3$ and $R_4$ form an unsubstituted or substituted aromatic ring with $C_1$ and $C_2$; and $R_5$ is —OH or a glycine substituent;

or a pharmaceutically acceptable salt thereof, and one or more other agents or therapies.

2. A method of claim 1, wherein $R_5$ is —OH.

3. A method of claim 1, wherein $R_3$ and $R_4$ form an unsubstituted or substituted aromatic ring with $C_1$ and $C_2$.

4. A method of claim 1, wherein X is S.

5. A method of claim 1, wherein $R_1$ and $R_2$ are both methyl.

6. A method of claim 1, wherein $R_5$ is a glycine substituent.

7. A method of claim 1, wherein $R_4$ is —OH, —H, or —$CH_3$.

8. A method of claim 1, wherein the compound is complexed with pyridine hydrochloride.

9. A method of claim 1, wherein the compound has a formula

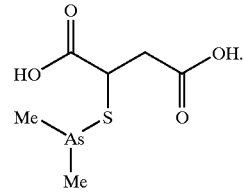

10. A method of claim 1, wherein the compound has a formula

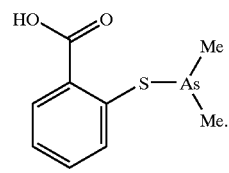

11. A method of claim 1, wherein the compound has a formula

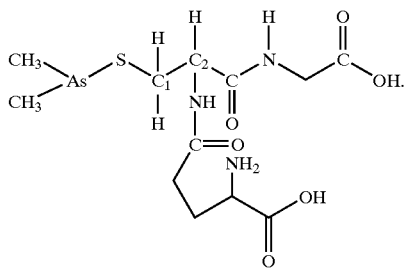

12. A method of claim 11, wherein the compound is provided as a formulation further comprising a pharmaceutical carrier, wherein the formulation has a pH of 5 to 7.

13. A method of claim 1, wherein the other agent or therapy is a chemotherapeutic agent or therapy.

14. A method of claim 13, wherein the other agent or therapy is a chemotherapeutic agent selected from cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, gemcitabien, navelbine, farnesyl-protein tansferase inhibitors, transplatinum, 5-fluorouracil, vincristin, vinblastin, and methotrexate, or any apalog or derivative variant thereof.

15. A method of claim 13, wherein the other agent or therapy is a radiation therapy selected from γ-rays, X-rays, and radioisotopes.

16. A method of claim 1, wherein the other agent or therapy is an immunotherapeutic agent or therapy.

17. A method of claim 16, wherein the other agent or therapy is an antibody.

18. A method of claim 17, wherein the antibody is conjugated to a drug or toxin.

19. A method of claim 18, wherein the drug or toxin is selected from a chemotherapeutic, radionucleotide, ricin A chain, cholera toxin, and pertussis toxin.

20. A method of claim 19, wherein the drug is a chemotherapeutic selected from cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, gemcitabien, navelbine, farnesyl-protein tansferase inhibitors, transplatinum, 5-fluorouracil, vincristin, vinblastin, and methotrexate, or any analog or derivative variant thereof.

21. A method of claim 17, wherein the antibody targets a tumor marker selected from carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B, and p155.

22. A method of claim 1, wherein the other agent or therapy is gene therapy.

23. A method of claim 1, wherein the other agent or therapy is surgery.

24. A method of claim 1, wherein the cancer is selected from brain, lung, liver, spleen, kidney, lymph node, small intestine, pancreas, blood cells, bone, colon, stomach, breast, endometrium, prostate, testicle, ovary, central nervous system, skin, head and neck, esophagus, and bone marrow cancer.

25. A method of claim 24 wherein the cancer is a hematological cancer.

26. A method of claim 25, wherein the cancer is selected from leukemia, lymphoma, multiple myeloma, myelodysplasia, myeloproliferative disease, and refractory anemia.

27. A method of claim 26, wherein the cancer is acute promyelocytic leukemia.

28. A method of claim 1, wherein the compound and the one or more other agents or therapies are administered simultaneously.

29. A method of claim 1, wherein the one or more other agents or therapies are administered within about 5 minutes to within about 48 hours prior to or after administration of the compound.

30. A method of claim 29, wherein the one or more other agents or therapies are administered within about 5 minutes to within about 1 hour prior to or after administration of the compound.

* * * * *

UNITED STATES PATENT AND TRADEMARK OFFICE
CERTIFICATE OF CORRECTION

PATENT NO.        : 6,995,188 B2
APPLICATION NO. : 11/035178
DATED             : February 7, 2006
INVENTOR(S)       : Zingaro et al.

It is certified that error appears in the above-identified patent and that said Letters Patent is hereby corrected as shown below:

In Claim 14, column 53, line 12, replace "apalog" with "analog."

Signed and Sealed this

Fourth Day of July, 2006

JON W. DUDAS
*Director of the United States Patent and Trademark Office*

UNITED STATES PATENT AND TRADEMARK OFFICE
CERTIFICATE OF CORRECTION

PATENT NO. : 6,995,188 B2  Page 1 of 1
APPLICATION NO. : 11/035178
DATED : February 7, 2006
INVENTOR(S) : Zingaro et al.

It is certified that error appears in the above-identified patent and that said Letters Patent is hereby corrected as shown below:

In column 4, line 61, replace "refractory anemia" with --refractory leukemia--.

In the Claims:

In claim 26, column 54, line 21, replace "refractory anemia" with --refractory leukemia--.

Signed and Sealed this

Tenth Day of July, 2007

JON W. DUDAS
*Director of the United States Patent and Trademark Office*

UNITED STATES PATENT AND TRADEMARK OFFICE
CERTIFICATE OF CORRECTION

| | |
|---|---|
| PATENT NO. | : 6,995,188 B2 |
| APPLICATION NO. | : 11/035178 |
| DATED | : February 7, 2006 |
| INVENTOR(S) | : Zingaro et al. |

It is certified that error appears in the above-identified patent and that said Letters Patent is hereby corrected as shown below:

Claim 15, column 53, line 14, please replace "claim 13" with --claim 1--.

Signed and Sealed this
Twenty-fourth Day of April, 2012

David J. Kappos
*Director of the United States Patent and Trademark Office*